US006613959B1

(12) United States Patent
Sheen et al.

(10) Patent No.: US 6,613,959 B1
(45) Date of Patent: Sep. 2, 2003

(54) TRANSGENIC PLANTS EXPRESSING A MAPKKK PROTEIN KINASE DOMAIN

(75) Inventors: Jen Sheen, Boston, MA (US); Yelena V. Kovtun, Winchester, MA (US); Wan-Ling Chiu, Richmond, VA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/371,338

(22) Filed: Aug. 10, 1999

Related U.S. Application Data

(60) Provisional application No. 60/095,938, filed on Aug. 10, 1998.

(51) Int. Cl.[7] .......................... C12N 15/09; C12N 15/29; C12N 15/82; A01H 5/00

(52) U.S. Cl. ...................... 800/278; 800/279; 800/287; 800/298; 800/289; 800/295; 800/306; 800/317; 435/69.1; 435/418; 435/419; 435/468; 435/320.1; 536/23.1; 536/23.2; 536/23.6; 536/24.1

(58) Field of Search ................................ 800/278, 279, 800/287, 289, 295, 298, 306, 317; 435/69.1, 418, 419, 468, 320.1; 536/23.1, 23.2, 23.6, 23.7, 24.1

(56) References Cited

U.S. PATENT DOCUMENTS

| | | | |
|---|---|---|---|
| 5,527,695 A | | 6/1996 | Hodges et al. |
| 5,648,599 A | * | 7/1997 | Tanksley et al. |
| 5,658,772 A | | 8/1997 | Odell et al. |
| 5,723,765 A | | 3/1998 | Oliver et al. |

OTHER PUBLICATIONS

Mizoguchi et al. Trends in Biotechnol. vol. 15, pp. 15–19, 1997.*
Jouannic et al., "Plant Map Kinase Kinase Structure, Classification and Evolution," *Gene* 233:1–11 (1999).
Martin et al., "Map–Based Cloning of a Protein Kinase Gene Conferring Disease Resistance in Tomato," *Science* 262:1432–1436 (1993).
Mizoguchi et al., "A Gene Encoding a Mitogen–Activated Protein Kinase Kinase Kinase is Induced Simultaneously with Genes for a Mitogen–Activated Protein Kinase and an S6 Ribosomal Protein Kinase by Touch, Cold, and Water Stress in *Arabidopsis thaliana,*" *Proc. Natl. Acad. Sci. USA* 93:765–769 (1996).
Sen Gupta et al., "Increased Resistance to Oxidative Stress in Transgenic Plants that Overexpress Chloroplastic Cu/Zn Superoxide Dismutase," *Proc. Natl. Acad. Sci. USA* 90:1629–1633 (1993).
Weigel et al., "A developmental Switch Sufficient for Flower Initiation in Diverse Plants," *Nature* 377:495–500 (1995).
Felix et al., "Rapid Changes of Protein Phosphorylation are Involved in Transduction of the Elicitor Signal in Plant Cells," *Proc. Natl. Acad. Sci. USA* 88:8831–8834 (1991).

Hughes et al., "Complementation of byr1 in Fission Yeast By Mammalian Map Kinase Kinase Requires Coexpression of Raf Kinase," *Nature* 364:349–352 (1993).
Ito et al., "NPK15, a Tobacco Protein–Serine/Threonine Kinase with a Single Hydrophobic Region Near the Amino–Terminus," *Mol. Gen. Genet.* 245:1–10 (1994).
Seo et al., "Tobacco Map Kinase: A Possible Mediator in Wound Signal Transduction Pathways," *Science* 270:1988–1992 (1995).
Song et al., "A Receptor Kinase–Like Protein Encoded by the Rice Disease Resistance Gene, Xa21," *Science* 270:1804–1806 (1995).
Watillon et al., "A Calcium/Calmodulin–Binding Serine/Threonine Protein Kinase Homologous to the Mammalian Type II Calcium/Calmodulin–Dependent Protein Kinase Is Expressed in Plant Cells," *Plant Physiology* 101:1381–1384 (1993).
Abel et al., "Transient Transformation of Arabidopsis Leaf Protoplasts: A Versatile Experimental System to Study Gene Expression," *The Plant Journal* 5:421–427 (1994).
Banno et al., "NPK1, a Tobacco Gene that Encodes a Protein with a Domain Homologous to Yeast BCK1, STE11, and Byr2 Protein Kinase," *Mol. Cell. Biol.* 13:4745–4752 (1993).
Banzet et al., "Accumulation of Small Heat Shock Proteins, Including Mitochondrial HSP22, Induced by Oxidative Stress and Adaptive Response in Tomato Cells," *The Plant Journal* 13:519–527 (1998).
Bennett and Tonks, "Regulation of Distinct Stages of Skeletal Muscle Differentiation by Mitogen–Activated Protein Kinases," *Science* 278:1288–1291 (1997).
Bohnert and Jensen, "Strategies for Engineering Water–Stress Tolerance in Plants," *TIBTECH* 14:89–97 (1996).
Bolwell and Wojtaszek, "Mechanisms for the Generation of Reactive Oxygen Species in Plant Defense—A Broad Perspective," *Physiological and Molecular Plant Pathology* 51:347–366 (1997).
Bray, "Plant Responses to Water Deficit," *Trends in Plant Science* 2:48–54 (1997).

(List continued on next page.)

*Primary Examiner*—Phuong T. Bui
(74) *Attorney, Agent, or Firm*—Clark & Elbing LLP

(57) ABSTRACT

The invention features a method for increasing stress resistance or tolerance in a plant, the method including the steps of: (a) introducing into plant cells a transgene including DNA encoding a kinase domain of a mitogen-activated protein kinase kinase kinase (MAPKKK) operably linked to a promoter functional in plant cells to yield transformed plant cells; and (b) regenerating a transgenic plant from the transformed cells, wherein the kinase domain of said MAPKKK is expressed in the cells of the transgenic plant, thereby increasing the level of stress resistance or tolerance in the transgenic plant. The invention further features plants including a recombinant transgene capable of expressing a kinase domain of a mitogen-activated protein kinase kinase kinase (MAPKKK) or a kinase domain thereof, wherein the transgene is expressed in said plant under the control of a promoter that is functional in a plant cell.

9 Claims, 26 Drawing Sheets

OTHER PUBLICATIONS

Chamnongpol et al., "Defense Activation and Enhanced Pathogen Tolerance Induced by $H_2O_2$ in Transgenic Tobacco," *Proc. Natl. Acad. Sci. USA* 95:5818–5823 (1998).

Cheikh and Jones, "Disruption of Maize Kernel Growth and Development by Heat Stress," *Plant Physiol.* 106:45–51 (1994).

Chen et al., "The Promoter of a $H_2O_2$–Inducible, Arabidopsis Glutathione S–Transferase Gene Contains Closely Linked OBF–and OBF1–Binding Sites," *The Plant Journal* 10:955–966 (1996).

Clark et al., "Association of the Arabidopsis CTR1 Raf–Like Kinase with the ETR1 and ERS Ethylene Receptors," *Proc. Natl. Acad. Sci. USA* 95:5401–5406 (1998).

Clarke, "Switching off Map Kinases," *Current Biology* 4:647–650 (1994).

Damm et al., "Efficient Transformation of *Arabidopsis Thaliana* Using Direct Gene Transfer to Protoplasts," *Mol. Gen. Genet.* 217:6–12 (1989).

Deak et al., "Fas–Induced Proteolytic Activation and Intracellular Redistribution of the Stress–Signaling Kinase MEKK1," *Proc. Natl. Acad. Sci. USA* 95:5595–5600 (1998).

Doi et al., "MSG5, a Novel Protein Phosphatase Promotes Adaptation to Pheromone Response in *S. cervisiae*," *The EMBO Journal* 13:61–70 (1994).

Garbers and Simmons, "Approaches to Understanding Auxin Action," *Trends in Cell Biology* 4:245–250 (1994).

Gray et al., "A Role for the Pkc1 Kinase Pathway of *Saccharomyces Cerevisiae* in Bud Emergence and Indentification of a Putative Upstream Regulator," *EMBO J.* 16:4924–4937 (1997).

Green and Fluhr, "UV–B Induced PR–1 Accumulation is Mediated by Active Oxygen Species," *The Plant Cell* 7:203–212 (1995).

Gupta et al., "Identification of a Dual–Specificity Protein Phosphatase that Inactivates a Map Kinase From Arabidopsis," *The Plant Journal* 16:581–589 (1998).

Gustin et al., "Map Kinase Pathways in the Yeast *Saccharomyces Cerevisiae*," *Microbiol. Mol. Biol. Rev.* 62:1264–1300 (1998).

Hagen et al., "Auxin–Induced Expression of the Soybean GH3 Promoter in Transgenic Tobacco Plants," *Plant Mol. Biol.* 17:567–579 (1991).

Hardtke et al., "The Arabidopsis Gene Monopteros Encodes a Transcription Factor Mediating Embryo Axis Formation and Vascular Development," *EMBO J.* 17:1405–1411 (1998).

Herskowitz, "Map Kinase Pathways in Yeast: For Mating and More," *Cell* 80:187–197 (1995).

Hirt, "Multiple Roles of Map Kinases in Plant Signal Transduction," *Trends in Plant Science* 2:11–15 (1997).

Holmberg and Bülow, "Improving Stress Tolerance in Plants by Gene Transfer," *Trends in Plant Science* 3:61–66 (1998).

Ichimura et al., "Isolation of ATMEKK1 (A Map Kinase Kinase)–Interacting Proteins and Analysis of a Map Kinase Cascade in Arabidopsis," *Biochem. Biophys. Res. Commun.* 253:532–543 (1998).

Inzé and Montagu, "Oxidative Stress in Plants," *Current Opinion in Biotechnology* 6:153–158 (1995).

Ishitani et al., "Genetic Analysis of Osmotic and Cold Stress Signal Transduction in Arabidopsis: Interactions and Convergence of Abscisic Acid–Dependent and Abscisic Acid–Independent Pathways," *The Plant Cell* 9:1935–1949 (1997).

Ishizaki–Nishizawa et al., "Low–Temperature Resistance of Higher Plants is Significantly Enhanced by a Nonspecific Cyanobacterial Desaturase," *Nat. Biotechnol.* 14:1003–1006 (1996).

Jaglo–Ottosen et al., "Arabidopsis CBF1 Overexpression Induces COR Genes and Enhances Freezing Tolerance," *Science* 280:104–106 (1998).

Jonak et al., "Map Kinases in Plant Signal Transduction," *Cell. Mol. Life Sci.* 55:204–213 (1999).

Karpinski et al., "Systemic Signaling and Acclimation in Response to Excess Excitation Energy in Arabidopsis," *Science* 284:654–657 (1999).

Kato et al., "Bmk1/Erk5 is Required for Cell Proliferation Induced by Epidermal Growth Factor," *Nature* 395:713–716 (1998).

Key, "Modulation of Gene Expression by Auxin," *Bioassays* 11:52–58 (1989).

Kleber et al., "CTR1, A Negative Regulator of the Ethylene Response Pathway in Arabidopsis, Encodes a Member of the Rat Family of Protein Kinases," *Cell* 72:427–441 (1993).

Kishor et al., "Overexpression of $\Delta^1$–Pyrroline–5–Carboxylate Synthetase Increases Proline Production and Confers Osmotolerance in Transgenic Plants," *Plant Physiol.* 108:1387–1394 (1995).

Kovtun et al., "Suppression of Auxin Signal Transduction by a MAPK Cascade in Higher Plants," *Nature* 395:716–720 (1998).

Kyriakis and Avruch, "Sounding the Alarm: Protein Kinase Cascades Activated by Stress and Inflammation," *The Journal of Biological Chemistry* 271:24313–24316 (1996).

Lamb and Dixon, "The Oxidative Burst in Plant Disease Resistance," *Annu. Rev. Plant Physiol. Plant Mol. Biol.* 48:251–275 (1997).

Landry et al., Regulation of Actin Dynamics by Stress–Activated Protein Kinase 2 (SAPK2)–Dependent Phosphorylation of Heat–Shock Protein of 27 kDa (Hsp27), *Biochem. Soc. Symp.* 64:79–89 (1999).

Lavoie et al., "Cyclin D1 Expression is Regulated Positively by the $p24/p44^{MAPK}$ and Negatively by the $p38/HOG^{MAPK}$ Pathway," *J. Biol. Chem.* 271:20608–20616 (1996).

Lee et al., "Derepression of the Activity of Genetically Engineered Heat Shock Factor Causes Constitutive Synthesis of Heat Shock Proteins Thermotolerance in Transgenic Arabidopsis," *The Plant Journal* 8:603–612 (1995).

Leung et al., "Arabidopsis ABA Response Gene ABI1: Features of a Calcium–Modulated Protein Phosphatase," *Science* 264:1448–1452 (1994).

Leyser, "Auxin Signalling: Protein Stability as a Versatile Control Target," *Curr. Biol.* 8:305–307 (1998).

Liu et al., "Two Transcription DREB1 and DREB2, with an EREBP/AP2 DNA Binding Domain Separate Two Cellular Signal Transduction Pathways in Drought–and–Low–Temperature–Responsive Gene Expression, Respectively, in Arabidopsis," *Plant Cell* 10:1391–1406 (1998).

Liu et al., "Soybean GH3 Promoter Contains Multiple Auxin–Inducible Elements," *Plant Cell* 6:645–657 (1994).

Machida et al., "Progress in Studies of Plant Homologs of Mitogen–Activated Protein (Map) Kinase and Potential Upstream Components in Kinase Cascades," *Critical Reviews in Plant Sciences* 16:481–496 (1997).

Marrs, "The Functions and Regulation of Glutathione S–Transferases in Plants," *Annu. Rev. Plant Physiol. Plant Mol. Biol.* 47:127–158 (1996).

Michalczuk et al., "Auxin Levels at Different Stages of Carrot Somatic Embryogenesis," *Phytochemistry* 31:1097–1103 (1992).

Misra–Press et al., "A Novel Mitogen–Activated Protein Kinase Phosphatase," *The Journal of Biological Chemistry* 270:14587–14596 (1995).

Mizoguchi et al., "Environmental Stress Response in Plants: The Role of Mitogen–Activated Protein Kinases," *Trends in Biotechnology* 15:15–19 (1997).

Molnar et al., "Cdc42Hs, but Not Rac1, Inhibits Serum–Stimulated Cell Cycle Progression at $G_1$/S Through a Mechanism Requiring p38/RK," *J. Biol. Chem.* 272:13229–13235 (1997).

Mordhorst et al., "Somatic Embryogenesis in *Arabidopsis thaliana* is Facilitated by Mutations in Genes Repressing Meristematic Cell Divisions," *Genetics* 149:549–563 (1998).

Morimoto, "Regulation of the Heat Shock Transcriptional Response: Cross Talk Between a Family of Heat Shock Factors, Molecular Chaperones, and Negative Regulators," *Genes Dev.* 12:3788–3796 (1998).

Morimoto et al., "Stress–Inducible Responses and Heat Shock Proteins: New Pharmacologic Targets for Cytoprotection," *Nat. Biotechnol.* 16:833–838 (1998).

Muda et al., "MKP–3, A Novel Cytosolic Protein–Tyrosine Phosphatase That Exemplifies a New Class of Mitogen–Activated Protein Kinase Phosphatase," *The Journal of Biological Chemistry* 271:4319–4326 (1996).

Muda et al., "Molecular Cloning and Functional Characterization of a Novel Mitogen–Activated Protein Kinase Phosphatase, MKP–4," *The Journal of Biological Chemistry* 272:5141–5151 (1997).

Nakashima et al., "The Expression Pattern of the Gene for NPK1 Protein Kinase Related to Mitogen–Activated Protein Kinase Kinase Kinase (MAPKKK) in a Tobacco Plant: Correlation with Cell Proliferation," *Plant Cell Physiol.* 39:690–700 (1998).

Nishihama et al., "Possible Involvement of Differential Splicing in Regulation of the Activity of Arabidopsis ANP–1 that is Related to Mitogen–Activated Protein Kianse Kinase Kinases (MAPKKKs)," *The Plant Journal* 12:39–48 (1997).

Noctor and Foyer, "Ascorbate and Glutathione: Keeping Active Oxygen Under Control," *Annu. Rev. Plant Physiol. Plant Mol. Biol.* 49:249–279 (1998).

Nuccio et al., "Metabolic Engineering of Plants for Osmotic Stress Resistance," *Current Opinion in Plant Biology* 2:128–134 (1999).

Pardo et al., "Stress Signaling Through $Ca^{2+}$/Calmodulin–Dependent Protein Phosphatase Calcineurin Mediates Salt Adaptation in Plants," *Proc. Natl. Acad. Sci. USA* 95:9681–9686 (1998).

Pei et al., "Role of Farnesyltransferase in ABA Regulation of Guard Cell Anion Channels and Plant Water Loss," *Science* 282:287–290 (1998).

Posas et al., "Activation of the Yeast SSK2 Map Kinase Kinase by the SSK1 Two–Component Response Regulator," *EMBO J.* 17:1385–1394 (1998).

Potts et al., "A Protein–Tyrosine/Serine Phosphatase Encoded by the Genome of the Cyanobacterium *Nostoc commune* UTEX 584," *The Journal of Biological Chemistry* 268:7632–7635 (1993).

Prändl et al., "HSF3, A New Heat Shock Factor from *Arabidopsis thaliana*, Derepresses the Heat Shock Response and Confers Thermotolerance When Overexpressed in Transgenic Plants," *Mol. Gen. Genet.* 258:269–278 (1998).

Prasad, "Mechanisms of Chilling–Induced Oxidative Stress Injury and Tolerance in Developing Maize Seedlings: Changes in Antioxidant System, Oxidation of Proteins and Lipids, and Protease Activities," *The Plant Journal* 10:1017–1026 (1996).

Reichheld et al., "Specific Checkpoints Regulate Plant Cell Cycle Progression in Response to Oxidative Stress," *The Plant Journal* 17:647–656 (1999).

Ribnicky et al., "The Effects of Exogenous Auxins on Endogenous Indole–3–Acetic Acid Metabolism," *Plant Physiol.* 112:549–558 (1996).

Roxas et al., "Overexpression of Glutathione S–Transferase/Glutathione Peroxidase Enhances the Growth of Transgenic Tobacco Seedlings During Stress," *Nature Biotechnology* 15:988–991 (1997).

Saitoh et al., "Mammalian Thioredoxin is a Direct Inhibitor of Apoptosis Signal–Regulating Kinase (Ask) 1," *EMBO J.* 17:2596–2606 (1998).

Schraudner et al., "Ozone–Induced Oxidative in the Ozone Biomonitor Plant, Tobacco Bel W3," *The Plant Journal* 16:235–245 (1998).

Sheen, "Mutational Analysis of Protein Phosphatase 2C Involved bi Abscisic Acid Signal Transduction in Higher Plants," *Proc. Natl. Acad. Sci. USA* 95:975–980 (1998).

Sheen, "Protein Phosphatase Activity is Required for Light–Inducible Gene Expression in Maize," *The EMBO Journal* 12:3497–3505 (1993).

Sitbon et al., "Expression of Auxin–Regulated Genes," *Physiological Plantarum* 100:443–455 (1997).

Smith and Walker, "Plant Protein Phosphatases," *Annu. Rev. Plant Physiol. Plant Mol. Biol.* 47:101–125 (1996).

Storozchenko et al., "The Heat Shock Element is a Functional Component of the Arabidopsis APX1 Gene Promoter[1]," *Plant Physiol.* 118:1005–1014 (1998).

Siguira et al., "pmp1+, a Suppressor of Calcineurin Deficiency, Encodes a Novel Map Kinase Phosphatase in Fission Yeast," *The EMBO Journal* 17:140–148 (1998).

Sun and Tonks, "The Coordinated Action of Protein Tyrosine Phosphatases and Kinases in Cell Signaling," *TIBS* 19:480–485 (1994).

Sun et al., "MKP–1 (3CH134), an Immediate Early Gene Product, is a Dual Specificity Phosphatase That Dephosphorylates Map KINASE In Vivi," *Cell* 75:487–493 (1993).

Sun et al., "Inhibition of Ras–Induced DNA Synthesis by Expression of the Phosphatase MKP–1," *Science* 266:285–288 (1994).

Takahashi et al., "Characterization of Two Genes Encoding Small Heat–Shock Proteins in *Arabidopsis Thaliana*," *Mol. Gen. Genet.* 219:365–372 (1989).

Takenaka et al., Activation of the Protein Kinase p38 in the Spindle Assembly Checkpoint and Mitotic Arrest, *Science* 280:599–602 (1998).

Tarczynski et al., "Stress Protection of Transgenic Tobacco by Production of the Osmolyte Mannitol," *Science* 259:508–510 (1993).

Tonks and Neel, "From Form to Function: Signaling by Protein Tyrosine Phosphatases," *Cell* 87:365–368 (1996).

Tuomainen et al., "Ozone Induction of Ethylene Emission in Tomato Plants: Regulation by Differential Accumulation of Transcripts for the Biosynthetic Enzymes," *The Plant Journal* 12:1151–1162 (1997).

Ulmasov et al., "The ocs Element in the Soybean GH2/4 Promoter is Activated by Both Active and Inactive Auxin and Salicylic Acid Analogues," *Plant Mol. Biol.* 26:1055–1064 (1994).

Walbot, "Sources and Consequences of Phenotypic and Genotypic Plasticity in Flowering Plants," *Trends in Plant Science* 1:27–32 (1996).

Walker and Estelle, "Molecular Mechanisms of Auxin Action," *Current Opinion in Plant Biology* 1:434–439 (1996).

Ward et al., "Control of Map Kinase Activation by the Mitogen–Induced Threonine/Tyrosine Phosphatase PAC1," *Nature* 367:651–654 (1994).

Willekens et al., "Catalase is a Sink for $H_2O_2$ and is Indispensable for Stress Defence in $C_3$ Plants," *EMBO J.* 16:4806–4816 (1997).

Wishart and Dixon, "Gathering SYTX: Phosphatase–like Form Predicts Functions for Unique Protein–Interaction Domains," *TIBS* 23:301–306 (1998).

Xia et al., "JNKK1 Organizes a Map Kinase Module Through Specific and Sequential Interactions with Upstream and Downstream Components Mediated by Its Amino–Terminal Extension," *Genes Dev.* 12:3369–3381 (1998).

Xu et al., "Molecular Characterization of a Tyrosine–Specific Protein Phosphatase Encoded by a Stress–Responsive Gene in Arabidopsis," *Plant Cell* 10:849–857 (1998).

Xu et al., "MEKK1 Phosphorylates MEK1 and MEK2 but Does Not Cause Activation of Mitogen–Activated Protein Kinase," *Proc. Natl. Acad. Sci. USA* 92:6808–6812 (1995).

Yuasa et al., "Tumor Necrosis Factor Signaling to Stress–Activated Protein Kinase (SAPK)/Jun $NH_2$–Terminal Kinase (JNK) and p38," *J. Biol. Chem.* 273:22681–22692 (1998).

Zaitsevskaya–Carter et al., "Spm1, A Stress–Activated Map Kinase that Regulates Morphogenesis in *S.pombe*," *EMBO J.* 16:1318–1331 (1997).

Zhang et al., "Salicylic Acid Activates a 48–kD Map Kinase in Tobacco," *Plant Cell* 9:809–824 (1997).

Zhong et al., "Direct Sensing of Heat and Oxidation by Drosophila Heat Shock Transcription Factor," *Mol. Cell* 2:101–108 (1998).

\* cited by examiner

FIG. 1
a
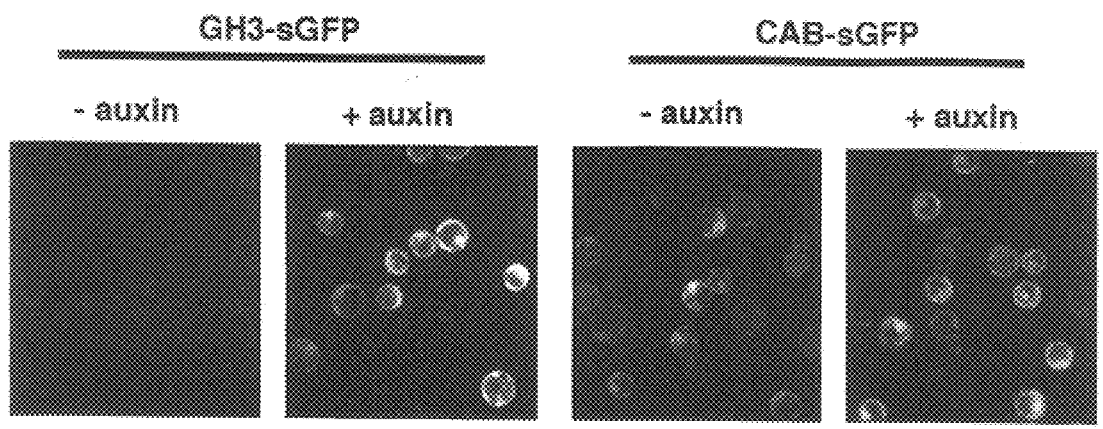
b
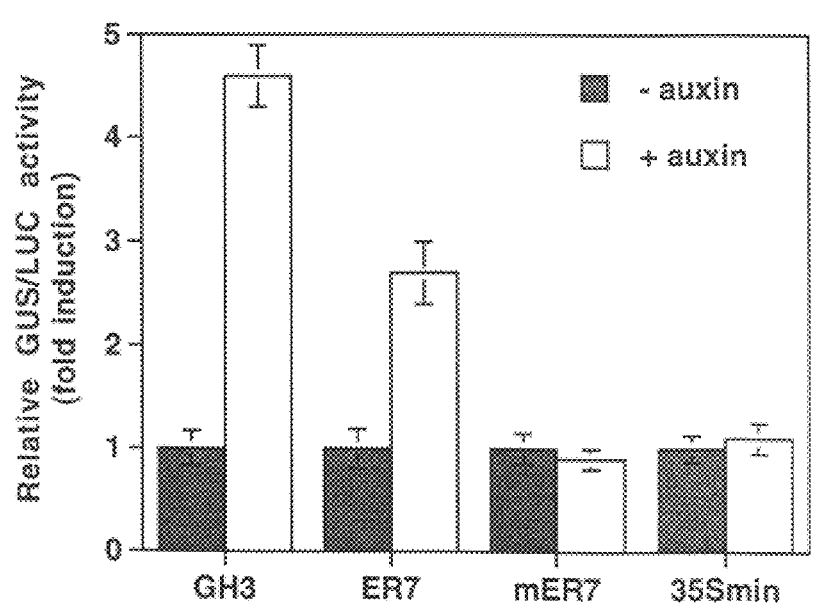

Fig. 2
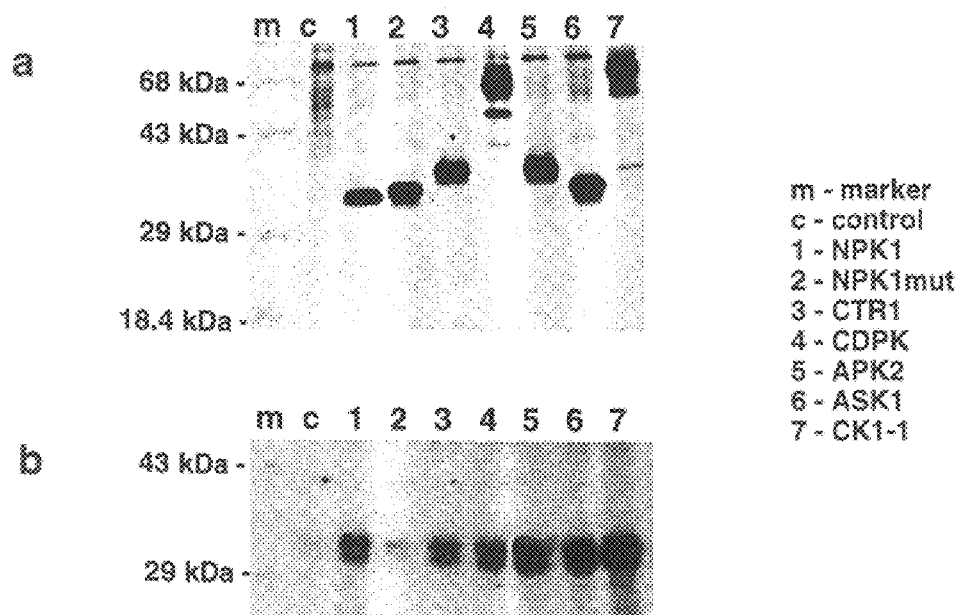
m - marker
c - control
1 - NPK1
2 - NPK1mut
3 - CTR1
4 - CDPK
5 - APK2
6 - ASK1
7 - CK1-1
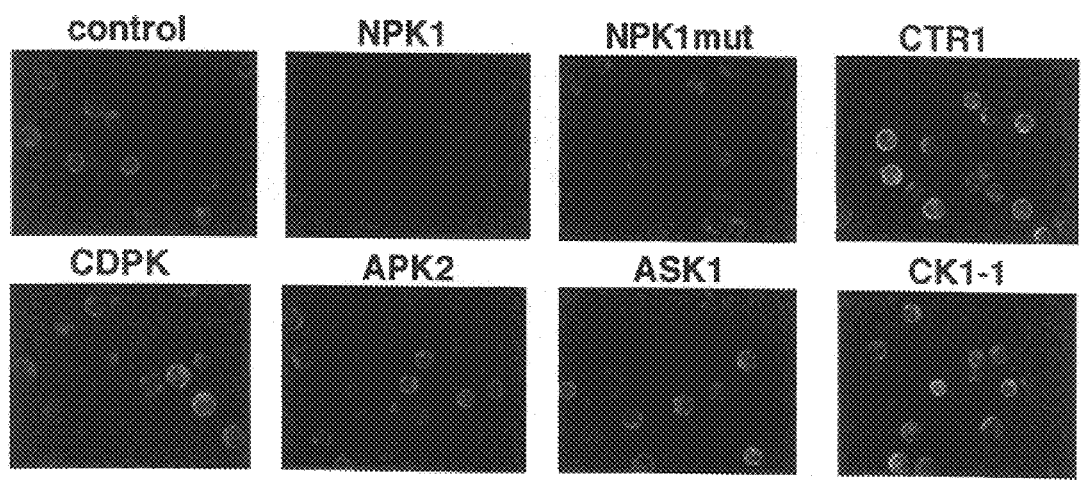

FIG. 2
d
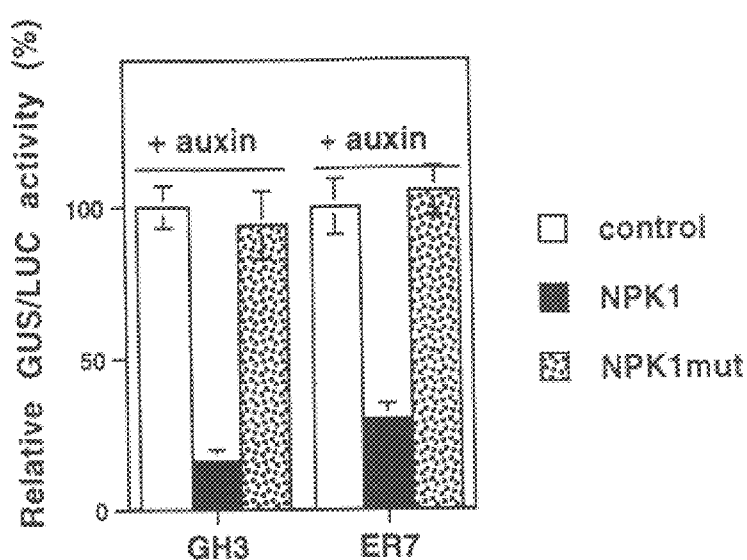
e
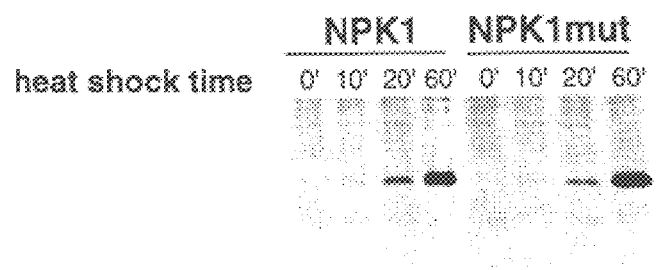
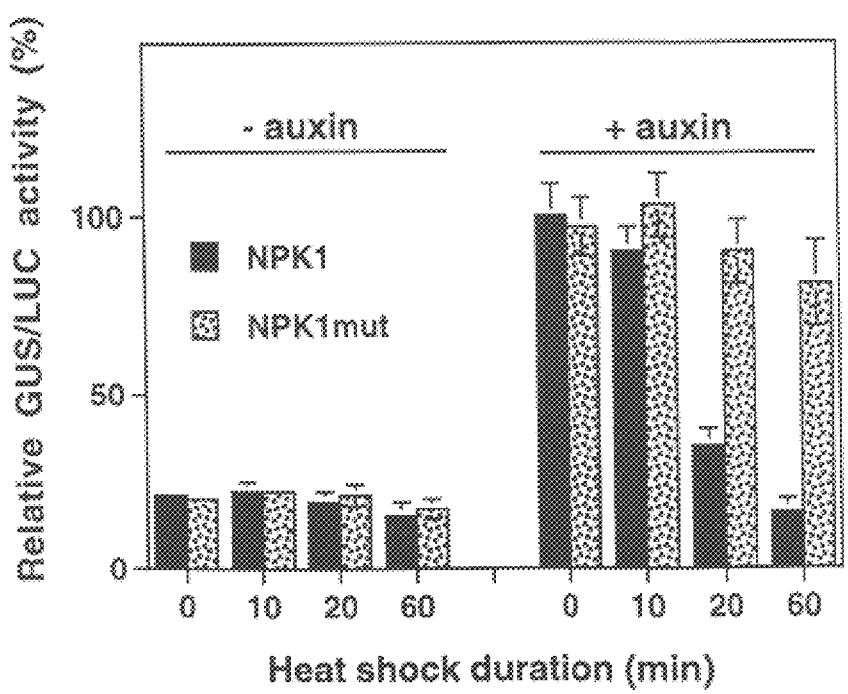

FIG. 3
a
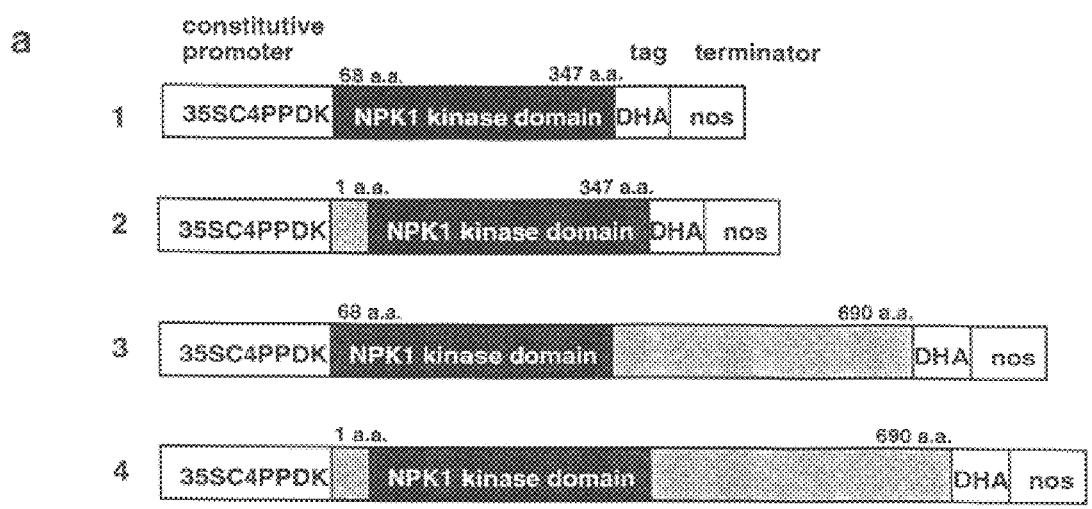
b
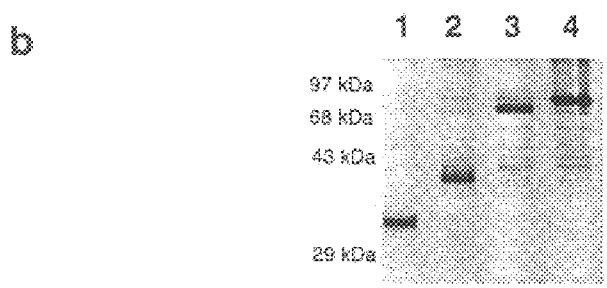
c
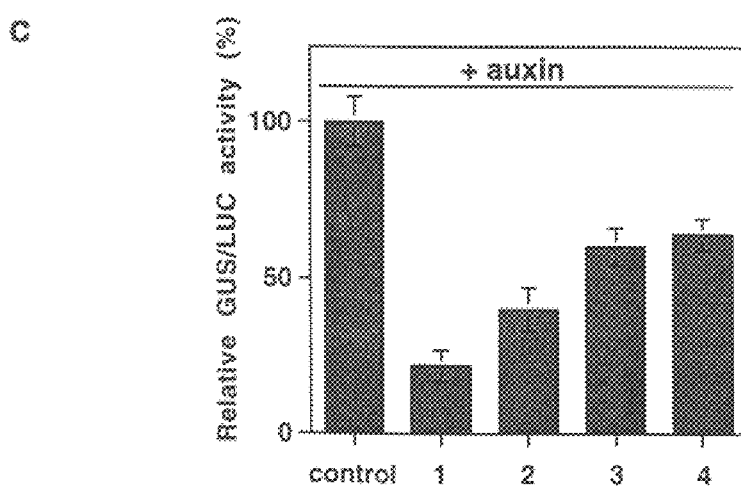

FIG. 4
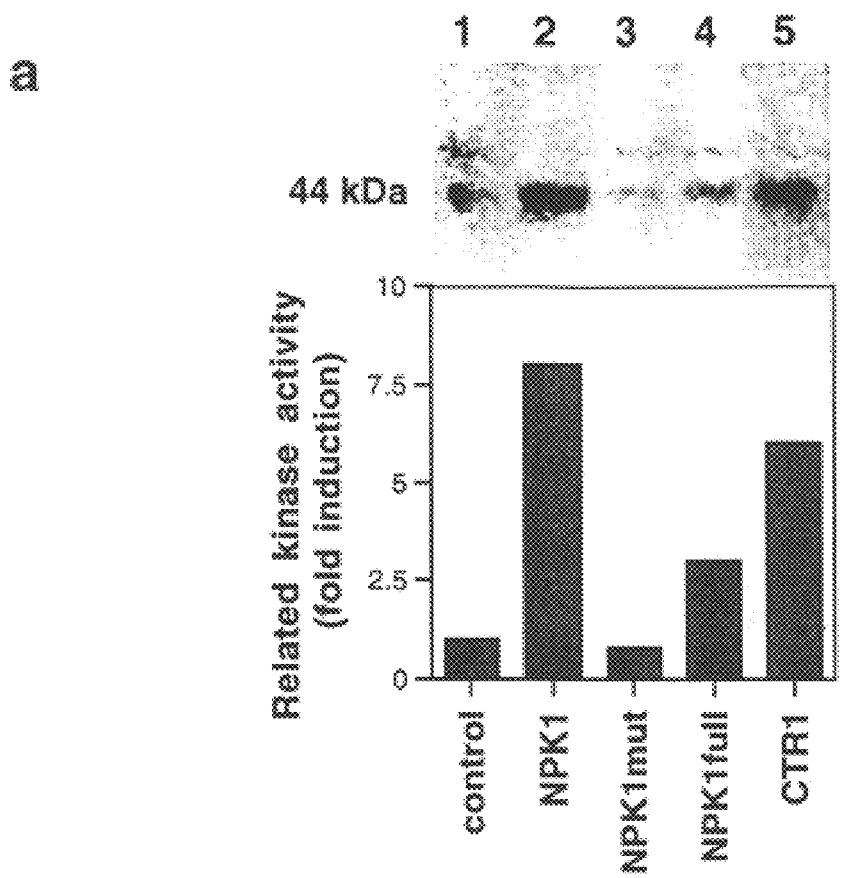
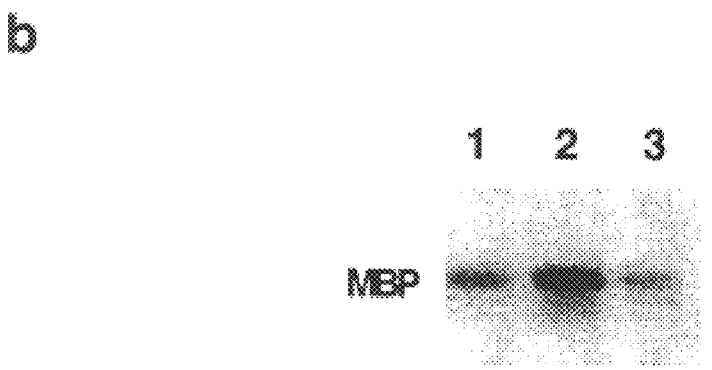

FIG. 4
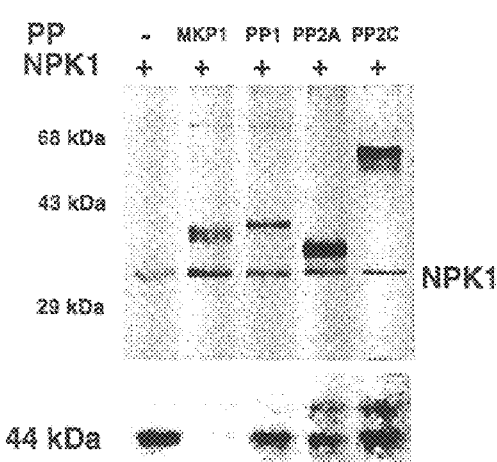
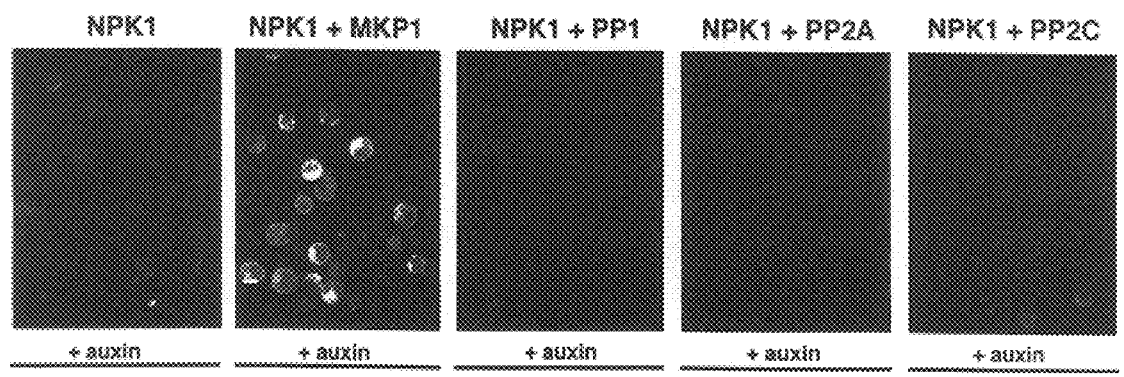

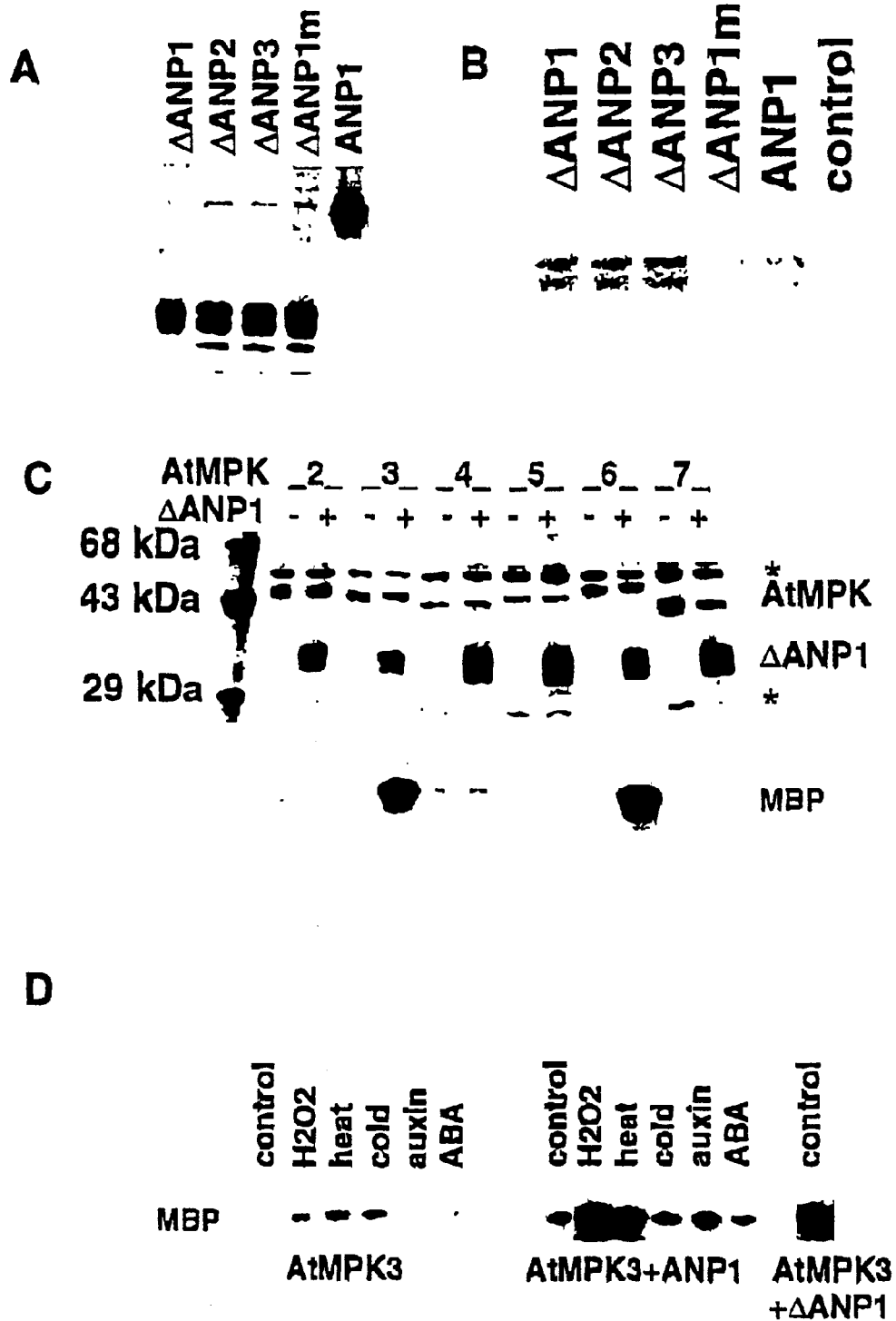

Fig. 7
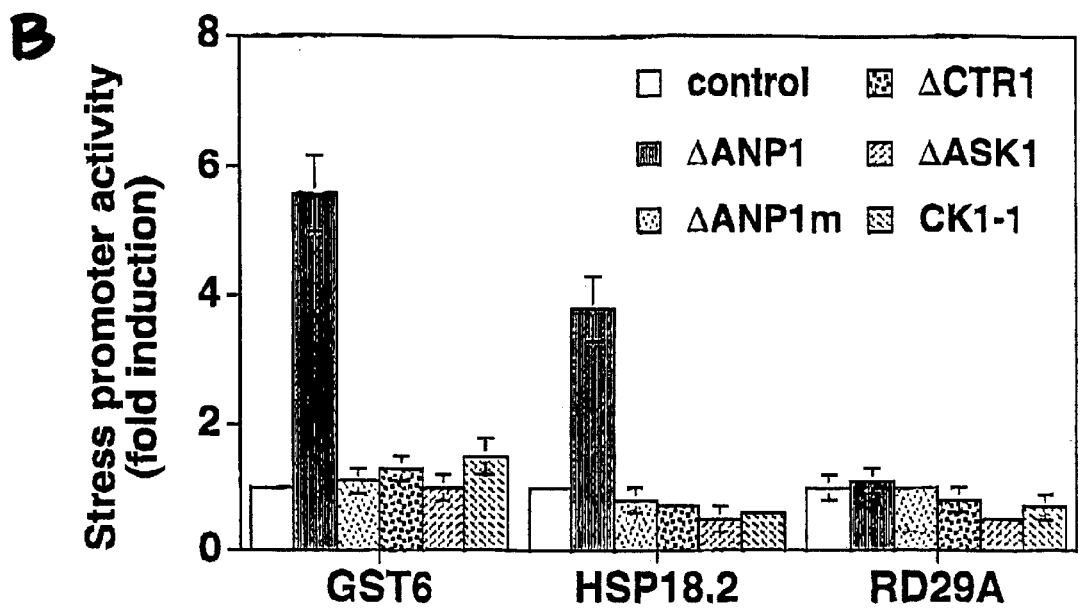
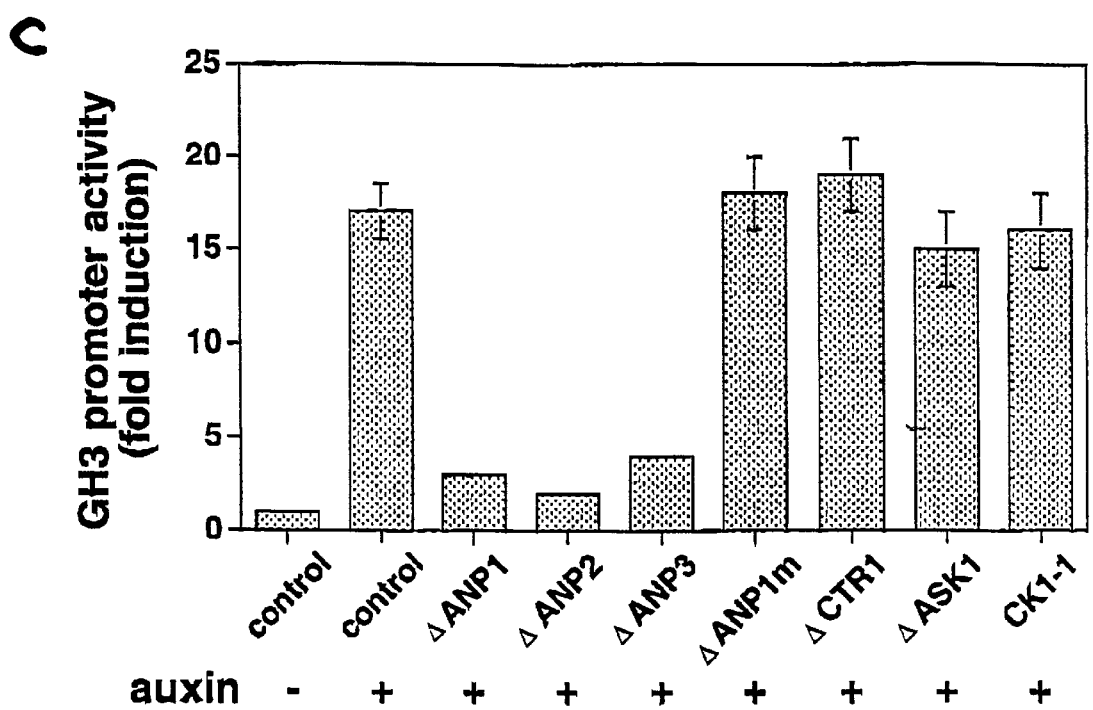

Fig. 8
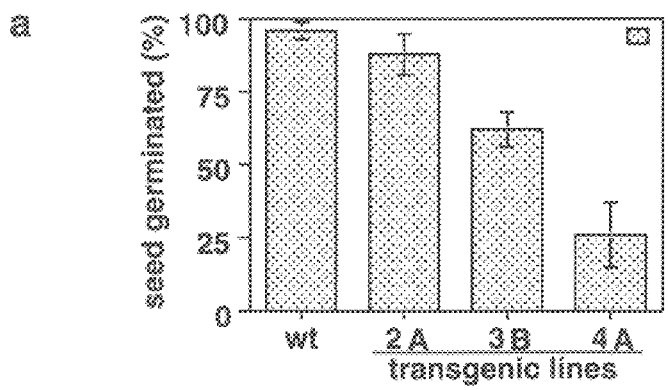
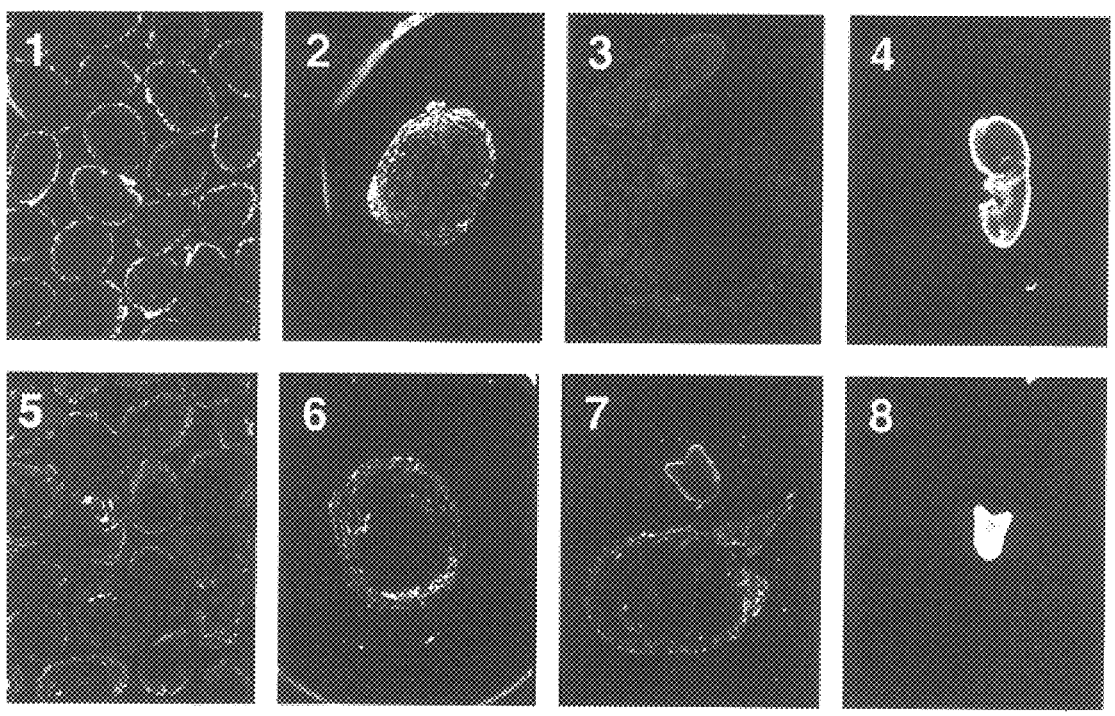

Fig. 8
c
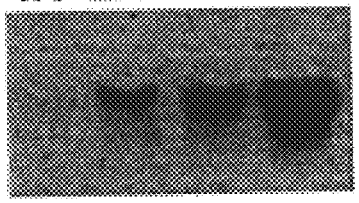
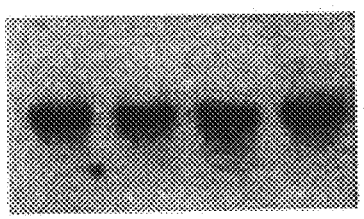
d
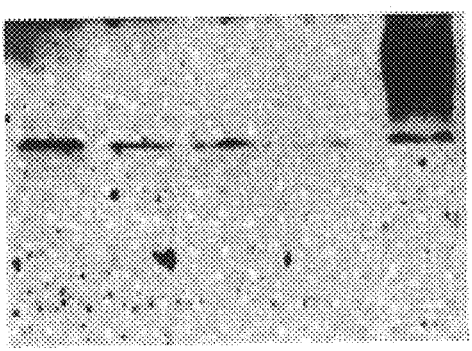

```
ANP1L  MQDFFGSVRRSLVFR SSDDDNQENQ-PPF  PGVLADKITS IRKSK FIKPSFS-PPP A  NTVD---------MA PPIS RKG LIGRGA   79
ANP2           RSLVFR ST DENQENHPPPF  PSLLADKIT C IRKS MVFAKSQSP-EN--N  STVQ---------IK PPIR RKG LIGRGA   69
ANP3   MQDILGSVRRSLVFR SSLAG-DDGTSGGG  LSGFVG INS IRS R IGLFSKPP- GL A  PRKE---------EAP SIR RKG LIG GA    78
NPK1   MQDFIGSVRRSLVFK  G DTGAAGVGSG  PGGFVE LG S IRKSS GIFS KAHV AL S  ISKAELPAKARKDDT PPIR RKG M GGGA    90

ANP1L  FGTVYMGMNLDSGELLAVKQVLIAAN ASK  EKTQAHIQELEEEV LLKNLSHPNIVRYLG  TVRE DT LNILLEFVPGGSISSLLEKFG PF  169
ANP2   FGTVYMGMNLDSGELLAVKQ LI  CASK  EKTQAHIQELEEEV LLKNLSHPNIVRYLG  TVRE DET LNILLEFVPGGSISSLLEKFGAF   159
ANP3   FGRVYMGMNLDSGELLAI KQVLIA SSASK  EKTQ HI ELEEEV LLKNLSHPNIVRYLG  TVRE SDSLNIL EFVPGGSISSLLEKFGSF   168
NPK1   FGRVYMGMN DSGELLA KE S AM CASR  ER QAH VRELEEEV LLKNLSHPNIVRYLG  TA EAGSLNILLEFVPGGSISSLL KFGSF   180

ANP1L  PESVVR T QLLLGLEYLHNHA IMHRDIK  GANILVDNKGCIKLADFGASK VAELATMT  GAKSMKGTPYW APEVILQTGHSFSADIWS   259
ANP2   PESVVR T N LLLGLEYLHNHA IMHRDIK  GANILVDN  GCIKLADFGASK VAELAT IS  GAKSMKGTPYW APEVILQTGHSFSADIWS   249
ANP3   PE VI IM T QLLLGLEYLHN G IMHRDIK  GANILVDNKGCI LADFGASK VVELATVN  GAKSMKGTPYW APEVILQTGHSFSADIWS   258
NPK1   PESVIR M T QLLLGLEYLHKNG IMHRDIK  GANILVDNKGCIKLADFGASK VVELATMT  GAKSMKGTPYW APEVILQTGHSFSADIWS   270

ANP1L  VGCTVIEM TGK APWSQQYKEVAAIF IGT  TKSHPPIPDT SSDAKDFLLKCLQ VPNLR  PT ASELLKHPFV GKHK SASTDLGSVLN    349
ANP2   VGCTVIEM V TGK APWSQQYKE IAAIFHIGT  TKSHPPIPDN SSDANDFLLKCLQ EPNLR  PTASELLKHPFVTGK Q PSASKDLTSFMD     339
ANP3   VGCTVIEM ATGK PPWSE QY  AAVL HIGR  TK AHPIPE LSPEA KDFLM KCLHKEPSLR  LSA ELL HPFVTGKR E PYPAYRN SLTEC    348
NPK1   VGCT IIEM ATGK PPWSQQY  EVAAL FHIGT  TKSHPPIPE H LSAE SKDFLLKCLQ EPHLR  HSAS LL QHPFVTAEHQ ARPFLRSSFMG    360

ANP1S                   MMRIS 376
ANP1L  LSTPLPLQINNTK STPDSTCDDVGDMCNFG  SLNYSL VDPVKSI QNKNL---WQQNDNGG D  E DMCL ID DEN LTFDGEMSST EKDCHLK  436
ANP2   SCSPLPSELTNIT SYQTSTSDDVGDICNLG  SLTCT AFPEKSI QNNSLCLKSNNGYDDD D  DNDMCL ID DEN LTYNGETGPS DNNTDAK  429
ANP3   GNPITTQGMNVRS SINSLIRRSTCSGLKDV  CELGS RSSIIYP KSNN---SGFGWRDG D  SDD CQTD MDDLCNIESVRNNV SQSTDLN  435
NPK1   PENMAAQRMDVRT I-IPDMRASCNGLKDV   CGVSAVRCSTVYPE SLG--KESLWKLGNS   DDDM QM NDDF MFGASVKCSSDLHSPANY  447
                                                                               A
ANP1L   SCDDISDMSIALKS KFDESP GNGE-----   ----------------K STMSMECDQP S  YSEDD ELTESKIKAFLDEKA DLKKLQTP   504
ANP2   KSCDT SEISDILK CKFDE NSGNGE-----   ----------------T TKVSMEVDHP S  YSEDE NELTESKIKAFLD KA LKKLQTP   497
ANP3   KSFNP CDSTDNWS CKFDESP KVMKSKSNL    LSYQASQLQTG---VPCD ETSLTFAGGS S  VAEDD YKG EL KIKS FLDEKA DLK LQTP   522
NPK1   KSFNP CEPDNDWP CKFDESP ELTKSQANL   HYDQATIKPTNNPIMSYK DLAFTFPSGQ S  AAEDDD ELTESKI RAFLDEKA DLKKLQTP   537
                         B                                                        C
ANP1L  LYEEFYN SLITFS SCME NLSNSKR DTA  RGFLK LPPKSRSP SRGPLGGS PSRATDATS  ---C SK P GSGGS REL INNGGDEASQDGV  591
ANP2   LYEEFYN GMITCS P ICME SNINNNKR EAP  RGFLK LPPKSRSP SQGHIGRS PSRATD AC  ---C SK P ESGNSSGAPKNSNASAGAE---  581
ANP3   L EEF N AM---N GIPQGALGDTNIYNL   ----NLP SI KTP  L-----PSRRLS IS  D--AMP SPLKSSK RTL NTSRVMQSGTE---   595
NPK1   LYE FYN SL---NVSSTP SPVGTGNK NVP  -SNINL PPKSRSP KRM-----LSRRLSTAI  EGAC AP S VTHSKR ISN IGGLNGEAIQEAQ  618
                                                     D
ANP1L  SARVTDWRGLVVDTKQELSQCVAL SEIEKK  WKEELD QELERKR EIM RQAGL GSS PRDRG  MSR Q EKSRFASPGK                  666
ANP2   -------------QESNSQSVAL SEIERK   WKEELD QELERKR EI  ROAG GSS PRDRS  LSR HR EKSRFASPGK                  642
ANP3   PTQVNESTKKGVNNSR------CF SEIRRK   W EELY ELER HR  NL HA A GKTPLSG  HKG                             651
NPK1   LPRHNEWKDLLGSQREAVNS--SF SERQRR   WKEELD EL RKR EIM ROAVNL S EKDPI  LNR CR SKSRFASPGK                  690
                                           E
```

ANP1
Amino Acid Sequence

```
GSVRRSLVFRPSSDDDNQENQPPFPGVLADKITSCIRKSKIFIK
PSFSPPPPANTVDMAPPISWRKGQLIGRGAFGTVYMGMNLDSGELLAVKQVLIAANFA
SKEKTQAHIQELEEEVKLLKNLSHPNIVRYLGTVREDDTLNILLEFVPGGSISSLLEK
FGPFPESVVRTYTRQLLLGLEYLHNHAIMHRDIKGANILVDNKGCIKLADFGASKQVA
ELATMTGAKSMKGTPYWMAPEVILQTGHSFSADIWSVGCTVIEMVTGKAPWSQQYKEV
AAIFFIGTTKSHPPIPDTLSSDAKDFLLKCLQEVPNLRPTASELLKHPFVMGKHKESA
STDLGSVLNNLSTPLPLQINNTKSTPDSTCDDVGDMCNFGSLNYSLVDPVKSIQNKNL
WQQNDNGGDEDDMCLIDDENFLTFDGEMSSTLEKDCHLKKSCDDISDMSIALKSKFDE
SPGNGEKESTMSMECDQPSYSEDDDELTESKIKAFLDEKAADLKKLQTPLYEEFYNSL
ITFSPSCMESNLSNSKREDTARGFLKLPPKSRSPSRGPLGGSPSRATDATSCSKSPGS
GGSRELNINNGGDEASQDGVSARVTDWRGLVVDTKQELSQCVALSEIEKKWKEELDQE
LERKRQEIMRQAGLGSSPRDRGMSRQREKSRFASPGK
```

ANP1
Nucleotide Sequence

```
   1 cggctccgtt cgtcgatcgc ttgttttccg tccttcttcc gacgacgata accaggagaa
  61 ccagcctccg tttcccggtg ttctcgccga taagatcacc tcttgcatcc gcaaatcgaa
 121 gatttttatc aaaccctcct tctcgcctcc tcctcctgct aacactgtag acatggcacc
 181 tccgatttcg tggaggaaag gtcagttaat tggtcgcggc gcgtttggta cggtgtacat
 241 gggtatgaat cttgactccg ggagcttct cgccgtcaaa caggttctga ttgcagccaa
 301 ttttgcttcc aaggaaaaga ctcaggctca tattcaggag cttgaagaag aagttaagct
 361 tcttaaaaat ctctcccatc ctaatatagt tagatatttg ggtacagtga gggaagatga
 421 taccctgaat atccttctcg agtttgttcc cggtggatcg atatcatcgc tcttggagaa
 481 atttggacct tttcctgaat cagttgtccg gacatacaca aggcaactgc ttttagggtt
 541 ggagtacctg cacaatcatg caattatgca cagagacatt aagggggcta atatccttgt
 601 ggataataaa ggatgcatta agcttgctga ttttggtgca tccaaacaag tagctgagtt
 661 ggctacgatg actggtgcaa aatctatgaa agggacacca tattggatgg ctccggaagt
 721 tatccttcaa actggacata gcttctctgc tgacatatgg agcgtcggct gtacagttat
 781 tgaaatggtg actgggaagg ctccttggag tcagcagtat aaagaggttg ctgctatctt
 841 cttcatagga acaacaaaat cacatcctcc aatacctgat actctctcct ctgatgcaaa
 901 agattttctg ctcaagtgtc tgcaggaggt accaaatctg cggccaaccg catctgagct
 961 actaaagcat ccttttgtta tggggaaaca caaggagtct gcttctactg atcttggttc
1021 tgtcctgaac aatcttagca ctccactacc gttacagata ataacacca agagcactcc
1081 agattctact tgcgacgatg taggtgacat gtgtaacttt ggcagtttga attattcact
1141 tgtagatcct gtgaaatcaa tccaaacaa aaatttatgg caacaaaatg ataatggagg
1201 tgatgaagac gatatgtgtt tgatagatga tgagaatttc ttgacatttg acggagaaat
1261 gagttctacc cttgaaaaag attgtcatct gaagaagagc tgtgatgaca taagtgatat
1321 gtccattgct ttgaagtcca aatttgacga agtcctggt aatggagaga agagtctac
1381 aatgagcatg gaatgtgacc aaccttcata ctcagaggat gatgatgagc tgaccgagtc
1441 aaaaattaaa gctttcttag atgagaaggc tgcagatcta aagaagttac agactcctct
1501 ctatgaagaa ttctacaata gttgatcac attctctccc agttgtatgg agagtaattt
1561 aagtaacagt aaaagagagg acactgctcg tggtttcctg aaactgcctc caaaaagcag
```

FIGURE 12

```
1621 gtcaccgagt cggggccctc ttggtggttc accttcaaga gcaacagacg caactagttg
1681 ttccaagagc ccaggaagtg gaggtagtcg tgaattgaat attaacaatg gaggtgatga
1741 agcttcacag gatggtgtat cagcacgggt cacagactgg aggggcctcg ttgttgacac
1801 taagcaggaa ttaagccagt gtgttgcttt gtcagagata gagaagaagt ggaaggaaga
1861 gcttgatcaa gaactggaaa gaaagcgaca agaaatcatg cgccaagcag ggttgggatc
1921 atccccaaga gacagaggca tgagccgaca gagagagaag tcgaggtttg catcaccagg
1981 aaaatgactt gcacaaaaag tctccggctt tttgattttt gattgctcaa ctagtatata
2041 tatctgtaac tcttatctcg ctgtgatgaa aagtagacac gaggtttggt ctgaatatat
2101 gattctgaac tggttgttga aggtattaga tgtgtgtaat gtgagtgtcg ggtgc
```

FIGURE 13

ANP2
Amino Acid Sequence

RSLVFRSTTDDENQENHPPPFPSLLADKITSCIRKSMVFAKSQS
PPNNSTVQIKPPIRWRKGQLIGRGAFGTVYMGMNLDSGELLAVKQALITSNCASKEKT
QAHIQELEEEVKLLKNLSHPNIVRYLGTVREDETLNILLEFVPGGSISSLLEKFGAFP
ESVVRTYTNQLLLGLEYLHNHAIMHRDIKGANILVDNQGCIKLADFGASKQVAELATI
SGAKSMKGTPYWMAPEVILQTGHSFSADIWSVGCTVIEMVTGKAPWSQQYKEIAAIFH
IGTTKSHPPIPDNISSDANDFLLKCLQQEPNLRPTASELLKHPFVTGKQKESASKDLT
SFMDNSCSPLPSELTNITSYQTSTSDDVGDICNLGSLTCTLAFPEKSIQNNSLCLKSN
NGYDDDDDNDMCLIDDENFLTYNGETGPSLDNNTDAKKSCDTMSEISDILKCKFDENS
GNGETETKVSMEVDHPSYSEDENELTESKIKAFLDDKAAELKKLQTPLYEEFYNGMIT
CSPICMESNINNNKREEAPRGFLKLPPKSRSPSQGHIGRSPSRATDAACCSKSPESGN
SSGAPKNSNASAGAEQESNSQSVALSEIERKWKEELDQELERKRREITRQAGMGSSPR
DRSLSRHREKSRFASPGK

ANP2
Nucleotide Sequence

```
   1 cgctcacttg tcttccgttc taccaccgac gatgagaatc aagagaatca tcctcctccg
  61 tttccttctc tcctcgccga taaaatcact tcctgtatcc gcaaatcaat ggttttcgcc
 121 aaatcccagt cacctccgaa taactccacc gtacaaatca aacctccgat tcggtggcgg
 181 aaaggtcagt taattggccg tggcgctttt ggtactgtgt atatgggtat gaatctcgat
 241 tccggtgagc ttctcgccgt taaacaggct ctgattacat ctaattgtgc atccaaggaa
 301 aaaactcagg ctcatattca ggagcttgaa gaggaagtga agctactcaa gaatctctct
 361 catccaaata tagttagata tttgggtacg gtgagggaag atgaaacttt gaatatcttg
 421 cttgaatttg ttcctggtgg atctatatct tcactcttgg agaaatttgg agcctttcct
 481 gaatctgttg ttcggacata cacgaaccaa ctgcttttgg gattggagta ccttcataat
 541 catgccatta tgcaccgtga cattaagggt gctaatatcc ttgtggataa tcaaggatgc
 601 attaaacttg ctgattttgg tgcgtccaaa caggtagcgg agttggctac tatttcgggt
 661 gccaaatcta tgaaaggaac tccctattgg atggctccag aagttattct tcaaaccggg
 721 catagctttt ctgctgatat ttggagtgta ggatgcacag tgattgaaat ggtgactgga
 781 aaagctcctt ggagccagca atataaagag attgctgcta ttttccacat tggaacgacg
 841 aaatcgcatc ctccaatccc tgacaatatc tcctctgacg caaatgattt tttgctcaag
 901 tgtctgcagc aggaaccaaa tctgcggcca accgcttctg agctgctaaa gcatccattt
 961 gttacgggca aacagaagga atctgcgtct aaagatctta cttcatttat ggacaattca
1021 tgcagtcctt taccatcaga gttgactaac attacgagct atcaaacatc tacgagtgac
1081 gatgtaggag acatctgtaa cttgggtagt ctgacttgta cacttgcttt ccctgagaaa
1141 tcaatccaaa ataacagttt gtgtctgaaa agtaataacg ggtatgatga cgatgatgat
1201 aatgatatgt gtttgattga cgatgagaat ttcttgacat ataatggaga gactggccct
1261 agtcttgaca ataatactga tgccaagaag agctgtgata ccatgagtga gatctctgat
1321 attttgaagt gcaaatttga cgaaaattct ggaacggag aaacagagac gaaagttagt
1381 atggaagttg accatccatc atactcggag gatgaaaatg agctgactga gtcgaaaatc
1441 aaagctttct tagatgacaa ggctgcagag ttaaagaagt tacagacgcc tctgtacgaa
1501 gaattctaca acggtatgat cacatgctcc cccatctgca tggagagtaa catcaataac
1561 aataaacgag aggaggcacc tcgtggtttc ttgaaactgc ctccaaaaag tcggtctccg
```

FIGURE 13

```
1621 agtcagggcc atattggtcg atcaccttct agagcaacag atgcagcctg ttgttccaag
1681 agtccagaaa gtggtaatag ctctggtgcc ccgaagaata gcaatgcaag tgctggtgct
1741 gaacaagaat caaacagtca aagtgtcgcg ctgtcggaga tagagaggaa gtggaaggaa
1801 gagcttgatc aagaacttga agaaagcga agagagatta cacggcaagc agggatggga
1861 tcatccccga gagatagaag cttgagccga catagagaga agtcaagatt tgcatctcca
1921 ggcaaatgat ctgtacaaaa gaaaagcagc caattttgca cttttgtctg taaggcttgt
1981 attgcttttg atctttcgat ttgctcatct agtatatatg atatagacat aaaattgtgc
2041 caacttaaag tttgaatata tatagatagc taaactattt gcttaagtag ggtgtgatgt
2101 gagaatgttg gtgcatattg agtgttaagc caaccacaga acaaatattt tcgagaaatt
2161 atcgaaagct ttgtttactt tcggtccggt ccg
```

FIGURE 14

ANP3
Amino Acid Sequence

MQDILGSVRRSLVFRSSLAGDDGTSGGGLSGFVGKINSSIRSSR
IGLFSKPPPGLPAPRKEEAPSIRWRKGELIGCGAFGRVYMGMNLDSGELLAIKQVLIA
PSSASKEKTQGHIRELEEEVQLLKNLSHPNIVRYLGTVRESDSLNILMEFVPGGSISS
LLEKFGSFPEPVIIMYTKQLLLGLEYLHNNGIMHRDIKGANILVDNKGCIRLADFGAS
KKVVELATVNGAKSMKGTPYWMAPEVILQTGHSFSADIWSVGCTVIEMATGKPPWSEQ
YQQFAAVLHIGRTKAHPPIPEDLSPEAKDFLMKCLHKEPSLRLSATELLQHPFVTGKR
QEPYPAYRNSLTECGNPITTQGMNVRSSINSLIRRSTCSGLKDVCELGSLRSSIIYPQ
KSNNSGFGWRDGDSDDLCQTDMDDLCNIESVRNNVLSQSTDLNKSFNPMCDSTDNWSC
KFDESPKVMKSKSNLLSYQASQLQTGVPCDEETSLTFAGGSSVAEDDYKGTELKIKSF
LDEKAQDLKRLQTPLLEEFHNAMNPGIPQGALGDTNIYNLPNLPSISKTPKRLPSRRL
SAISDAMPSPLKSSKRTLNTSRVMQSGTEPTQVNESTKKGVNNSRCFSEIRRKWEEEL
YEELERHRENLRHAGAGGKTPLSGHKG

ANP3
Nucleotide Sequence

```
    1 tcttcactga tctctctaca cattcaccgt cggcttctca aatgcaggat attctcggat
   61 cggttcgccg atccttggtt ttccggtcgt ctttggccgg agacgatggt actagcggcg
  121 gaggtcttag cggattcgtc gggaagatta actctagtat ccgtagctct cgaattgggc
  181 tcttttctaa gccgcctcca gggcttcctg ctcctagaaa agaagaagcg ccgtcgattc
  241 ggtggaggaa aggggaatta atcggttgcg gtgcttttgg aagagtttac atgggaatga
  301 acctcgattc cggcgagctt cttgcaatta acaggttttt aatcgctcca agcagtgctt
  361 caaaggagaa gactcagggt cacatccgag agcttgagga agaagtacaa cttcttaaga
  421 atctttcaca tccgaacatc gttagatact gggtactgt aagagagagt gattcgttga
  481 atattttgat ggagtttgtt cctgtggat caatatcatc tttgttggag aagtttggat
  541 cttttcctga gcctgtgatt attatgtaca caaagcaact tctgcttggg ctggaatatc
  601 ttcacaacaa tgggatcatg catcgagata ttaaggggc aaatattttg gtcgataaca
  661 aaggttgcat cagactcgca gattttggtg cttccaagaa agttgtagag ctagctactg
  721 taaatggtgc caaatctatg aaggggacgc cttattggat ggctcctgaa gtcattctcc
  781 agactggtca tagcttctct gctgatatat ggagtgttgg gtgcactgtg attgagatgg
  841 ctacggggaa gcctccctgg agcgagcagt atcagcagtt tgctgctgtc cttcatattg
  901 gtagaacaaa agctcatcct ccaattccag aagacctctc accagaggct aaagactttc
  961 taatgaaatg cttacacaaa gaaccaagct tgagactctc tgcaaccgaa ttgcttcagc
 1021 acccgtttgt cactggaaag cgccaggaac cttatccagc ttaccgtaat tctcttacgg
 1081 aatgtggaaa cccaataact actcaaggaa tgaatgttcg gagttcaata aattcgttga
 1141 tcaggaggtc gacatgttca ggcttgaagg atgtctgtga actgggaagc ttgaggagtt
 1201 ccattatata cccacagaag tcaaataact caggatttgg ttggcgagat ggagactctg
 1261 atgacctttg tcagaccgat atggatgatc tctgcaacat tgaatcagtc agaaacaatg
 1321 ttttgtcaca gtccaccgat ttaaacaaga gttttaatcc catgtgtgat tccacggata
 1381 actggtcttg caagtttgat gaaagcccaa agtgatgaa agcaaatct aacctgcttt
 1441 cttaccaagc ttctcaactc caaactggag ttccatgtga tgaggaaacc agcttaacat
 1501 ttgctggtgg ctcttccgtt gcagaggatg attataaagg cacagagttg aaaataaaat
 1561 cattttggga tgagaaggct caggatttga aaaggttgca gacccctctg cttgaagaat
 1621 tccacaatgc tatgaatcca ggaataccc aaggtgcact ggagacacc aatatctaca
```

FIGURE 14

```
1681 atttaccaaa cttaccaagt ataagcaaga cacctaaacg acttccgagt agacgactct
1741 cagcaatcag tgatgctatg cccagcccac tcaaaagctc caaacgtaca ctgaacacaa
1801 gcagagtgat gcagtcagga actgaaccaa ctcaagtcaa cgagtcgacc aagaagggag
1861 taaataatag ccgttgtttc tcagagatac gtcggaagtg ggaagaagaa ctctatgaag
1921 agcttgagag gcatcgagag aatctgcgac acgctggtgc aggagggaag actccattat
1981 caggccacaa aggatagtga acggctaaag agaaactgta tgtttctttc ttatgtttca
2041 aaattacttc ttcgtatttt tttttgttgg tggggtaatt tcatgagcta gtatgatata
2101 tgtagatagt tcttcaacgg ttacatagta ttattattta ttattaattt aattgcc
```

FIGURE 15

NPK1
Amino Acid Sequence

MQDFIGSVRRSLVFKQSGDFDTGAAGVGSGFGGFVEKLGSSIRK
SSIGIFSKAHVPALPSISKAELPAKARKDDTPPIRWRKGEMIGCGAFGRVYMGMNVDS
GELLAIKEVSIAMNGASRERAQAHVRELEEEVNLLKNLSHPNIVRYLGTAREAGSLNI
LLEFVPGGSISSLLGKFGSFPESVIRMYTKQLLLGLEYLHKNGIMHRDIKGANILVDN
KGCIKLADFGASKKVVELATMTGAKSMKGTPYWMAPEVILQTGHSFSADIWSVGCTII
EMATGKPPWSQQYQEVAALFHIGTTKSHPPIPEHLSAESKDFLLKCLQKEPHLRHSAS
NLLQHPFVTAEHQEARPFLRSSFMGNPENMAAQRMDVRTSIIPDMRASCNGLKDVCGV
SAVRCSTVYPENSLGKESLWKLGNSDDDMCQMDNDDFMFGASVKCSSDLHSPANYKSF
NPMCEPDNDWPCKFDESPELTKSQANLHYDQATIKPTNNPIMSYKEDLAFTFPSGQSA
AEDDDELTESKIRAFLDEKAMDLKKLQTPLYEGFYNSLNVSSTPSPVGTGNKENVPSN
INLPPKSRSPKRMLSRRLSTAIEGACAPSPVTHSKRISNIGGLNGEAIQEAQLPRHNE
WKDLLGSQREAVNSSFSERQRRWKEELDEELQRKREIMRQAVNLSPPKDPILNRCRSK
SRFASPGR

NPK1
Nucleotide Sequence

```
   1 ctgaacccta acgcacacaa cttcactctt tgctcctcca aatctctctc caatgcagga
  61 tttcatcggc tccgttcgcc gatctctggt tttcaagcag tccggagact tcgataccgg
 121 cgctgccggt gtcggcagcg gattcggagg cttcgttgag aaactaggtt cgagcattcg
 181 caaatcgagt attggaatct tctcgaaagc tcatgttcct gctcttccgt ctatttctaa
 241 agctgagctg cccgcgaagg ctcggaaaga tgacactccg ccaatccggt ggaggaaagg
 301 tgaaatgatt ggatgtggtg cttttggtag ggtttatatg gggatgaatg ttgattctgg
 361 agagttactc gctataaagg aggtttcgat tgcgatgaat ggtgcttcga gagagcgagc
 421 acaagctcat gttagagagc ttgaggaaga agtgaatcta ttgaagaatc tctcccatcc
 481 caacatagtg agatatttgg gaactgcaag agaggcagga tcattaaata tattgttgga
 541 atttgttcct ggtggctcaa tctcgtcact tttgggaaaa tttggatcct tccctgaatc
 601 tgttataaga atgtacacca agcaattgtt attagggttg aatacttgc ataagaatgg
 661 gattatgcac agagatatta aggagcaaa catacttgtt gacaataaag gttgcattaa
 721 acttgctgat ttcggtgcat ccaagaaggt tgttgaattg gctactatga ctggtgccaa
 781 gtcaatgaag ggtactccat actggatggc tcccgaagtc attctgcaga ctggccatag
 841 cttctctgct gacatatgga gtgtcggatg cactattatc gaaatggcta caggaaaacc
 901 tccttggagc cagcagtatc aggaggttgc tgctctcttc catataggga caaccaaatc
 961 ccatccccc atcccagagc atctttctgc tgaatcaaag gacttcctat taaaatgttt
1021 gcagaaggaa ccgcacctga ggcattctgc atcaaatttg cttcagcatc catttgttac
1081 agcagaacat caggaagctc gccttttct tcgctcatcc tttatgggaa accccgaaaa
1141 catggcggcg caaaggatgg atgttaggac ctcaatcatt cctgatatga gcttcctg
1201 caatggtttg aaagatgttt gtggtgttag cgctgtgagg tgctccactg tatatcccga
1261 gaattcctta gggaaagagt cactctggaa actaggaaac tctgatgatg acatgtgcca
1321 gatggataat gatgattta tgtttggtgc atctgtgaaa tgcagttcag atttgcattc
1381 tcctgctaat tataagagtt ttaatcctat gtgtgaacct gataacgatt ggccatgcaa
```

FIGURE 15

```
1441 atttgatgaa agtcccgagt tgacgaaaag tcaagcaaac ctgcattatg atcaagcaac
1501 tattaagccc actaataacc ccatcatgtc atacaaggag gatcttgctt tcacatttcc
1561 aagtgggcaa tctgcagccg aggatgatga tgaattgaca gagtctaaaa ttagggcatt
1621 ccttgatgaa aaggcaatgg acttgaagaa gctgcaaaca ccactatatg aaggattcta
1681 caattccttg aatgtttcca gcacaccgag tcccgttggc actgggaaca aggaaaatgt
1741 tccaagtaac ataaacttac caccaaaaag caggtcacca aaacgtatgc ttagcagaag
1801 gctctctact gccattgaag gtgcttgtgc tcccagccca gtgactcatt ccaagcgaat
1861 atcaaatatt ggtggcctaa atggtgaagc tattcaggaa gctcagttgc cgaggcataa
1921 tgaatggaaa gatcttcttg gttctcaacg tgaagcagtt aattcaagct ctctctgagag
1981 gcaaagaagg tggaagaag agcttgatga agagttgcaa aggaaacgag agattatgcg
2041 tcaggcagtc aacttatcac caccaaagga tccaattcta aatcgatgta gaagtaaatc
2101 aaggtttgca tctcctggaa gataaatgta tgtacttgtg tccctaaact aaagtcagtt
2161 tgaagaatat aattaatgat cctgcaaccc agaacagag agttagatgt cttgagcagg
2221 tatacgaacg tgaggttttc ttgacccgtt actacaggaa tatcagcgct tgtcagatag
2281 agtgagctgt tactacagga atatctgtca acctgttaat catattataa aatgccaata
2341 atttgcgttg tattcgtttt gatcattctc ctgagagcat tgtaagaaaa atgcaggcct
2401 ttttataacc tatataagtg ctctctcatg gtagttgcca atattaaaac gcagagaaaa
2461 gtcgagttct catctgctga attgtttgta aaatgtgata tattaatgta tttaccgtct
2521 tacaacc
```

FIGURE 16

Kinase Domains (Amino Acid Sequence)

ANP1

PPISWRKGQLIGRGAFGTVYMGMNLDSGELLAVKQVLIAANFASKEKTQAHIQELEEEVKLLKNLSHPNIVRYLGTVR
EDDTLNILLEFVPGGSISSLLEKFGPFPESVVRTYTRQLLLGLEYLHNHAIMHRDIKGANILVDNKGCIKLADFGASK
QVAELATMTGAKSMKGTPYWMAPEVILQTGHSFSADIWSVGCTVIEMVTGKAPWSQQYKEVAAIFFIGTTKSHPPIPD
TLSSDAKDFLLKCLQEVPNLRPTASELLKHPFVM

ANP2

PPIRWRKGQLIGRGAFGTVYMGMNLDSGELLAVKQALITSNCASKEKTQAHIQELEEEVKLLKNLSHPNIVRYLGTVR
EDETLNILLEFVPGGSISSLLEKFGAFPESVVRTYTNQLLLGLEYLHNHAIMHRDIKGANILVDNQGCIKLADFGASK
QVAELATISGAKSMKGTPYWMAPEVILQTGHSFSADIWSVGCTVIEMVTGKAPWSQQYKEIAAIFHIGTTKSHPPIPD
NISSDANDFLLKCLQQEPNLRPTASELLKHPFVT

ANP3

PSIRWRKGELIGCGAFGRVYMGMNLDSGELLAIKQVLIAPSSASKEKTQGHIRELEEEVQLLKNLSHPNIVRYLGTVR
ESDSLNILMEFVPGGSISSLLEKFGSFPEPVIIMYTKQLLLGLEYLHNNGIMHRDIKGANILVDNKGCIRLADFGASK
KVVELATVNGAKSMKGTPYWMAPEVILQTGHSFSADIWSVGCTVIEMATGKPPWSEQYQQFAAVLHIGRTKAHPPIPE
DLSPEAKDFLMKCLHKEPSLRLSATELLQHPFVT

NPK1

PPIRWRKGEMIGCGAFGRVYMGMNVDSGELLAIKEVSIAMNGASRERAQAHVRELEEEVNLLKNLSHPNIVRYLGTAR
EAGSLNILLEFVPGGSISSLLGKFGSFPESVIRMYTKQLLLGLEYLHKNGIMHRDIKGANILVDNKGCIKLADFGASK
KVVELATMTGAKSMKGTPYWMAPEVILQTGHSFSADIWSVGCTIIEMATGKPPWSQQYQEVAALFHIGTTKSHPPIPE
HLSAESKDFLLKCLQKEPHLRHSASNLLQHPFVT

Kinase Domains (Nucleotide Sequence)

ANP1

```
     cc
 181 tccgatttcg tggaggaaag gtcagttaat tggtcgcggc gcgtttggta cggtgtacat
 241 gggtatgaat cttgactccg gggagcttct cgccgtcaaa caggttctga ttgcagccaa
 301 ttttgcttcc aaggaaaaga ctcaggctca tattcaggag cttgaagaag aagttaagct
 361 tcttaaaaat ctctcccatc ctaatatagt tagatatttg ggtacagtga gggaagatga
 421 taccctgaat atccttctcg agtttgttcc cggtggatcg atatcatcgc tcttggagaa
 481 atttggacct tttcctgaat cagttgtccg gacatacaca aggcaactgc ttttagggtt
 541 ggagtacctg cacaatcatg caattatgca cagagacatt aaggggcta atatccttgt
 601 ggataataaa ggatgcatta agcttgctga ttttggtgca tccaaacaag tagctgagtt
 661 ggctacgatg actggtgcaa aatctatgaa agggacacca tattggatgg ctccggaagt
 721 tatccttcaa actggacata gcttctctgc tgacatatgg agcgtcggct gtacagttat
 781 tgaaatggtg actgggaagg ctccttggag tcagcagtat aaagaggttg ctgctatctt
 841 cttcatagga acaacaaaat cacatcctcc aatacctgat actctctcct ctgatgcaaa
 901 agatttcctg ctcaagtgtc tgcaggaggt accaaatctg cggccaaccg catctgagct
```

FIGURE 16

ANP2
```
    961 actaaagcat ccttttgtta tg
```

```
        cctccgat tcggtggcgg
    181 aaaggtcagt taattggccg tggcgctttt ggtactgtgt atatgggtat gaatctcgat
    241 tccggtgagc ttctcgccgt taaacaggct ctgattacat ctaattgtgc atccaaggaa
    301 aaaactcagg ctcatattca ggagcttgaa gaggaagtga agctactcaa gaatctctct
    361 catccaaata tagttagata tttgggtacg gtgagggaag atgaaacttt gaatatcttg
    421 cttgaatttg ttcctggtgg atctatatct tcactcttgg agaaatttgg agcctttcct
    481 gaatctgttg ttcggacata cacgaaccaa ctgcttttgg gattggagta ccttcataat
    541 catgccatta tgcaccgtga cattaagggt gctaatatcc ttgtggataa tcaaggatgc
    601 attaaacttg ctgattttgg tgcgtccaaa caggtagcgg agttggctac tatttcgggt
    661 gccaaatcta tgaaggaac tccctattgg atggctccag aagttattct tcaaaccggg
    721 catagctttt ctgctgatat ttggagtgta ggatgcacag tgattgaaat ggtgactgga
    781 aaagctcctt ggagccagca atataaagag attgctgcta ttttccacat tggaacgacg
    841 aaatcgcatc ctccaatccc tgacaatatc tcctctgacg caaatgattt tttgctcaag
    901 tgtctgcagc aggaaccaaa tctgcggcca accgcttctg agctgctaaa gcatccattt
    961 gttacg
```

ANP3
```
        ccgtcgattc
    241 ggtggaggaa aggggaatta atcggttgcg gtgcttttgg aagagtttac atgggaatga
    301 acctcgattc cggcgagctt cttgcaatta aacaggtttt aatcgctcca agcagtgctt
    361 caaaggagaa gactcagggt cacatccgag agcttgagga agaagtacaa cttcttaaga
    421 atctttcaca tccgaacatc gttagatact tgggtactgt aagagagagt gattcgttga
    481 atattttgat ggagtttgtt cctggtggat caatatcatc tttgttggag aagtttggat
    541 cttttcctga gcctgtgatt attatgtaca caaagcaact tctgcttggg ctggaatatc
    601 ttcacaacaa tgggatcatg catcgagata ttaagggggc aaatattttg gtcgataaca
    661 aaggttgcat cagactcgca gattttggtg cttccaagaa agttgtagag ctagctactg
    721 taaatggtgc caaatctatg aagggacgc cttattggat ggctcctgaa gtcattctcc
    781 agactggtca tagcttctct gctgatatat ggagtgttgg gtgcactgtg attgagatgg
    841 ctacggggaa gcctccctgg agcgagcagt atcagcagtt tgctgctgtc cttcatattg
    901 gtagaacaaa agctcatcct ccaattccag aagacctctc accagaggct aaagactttc
    961 taatgaaatg cttacacaaa gaaccaagct tgagactctc tgcaaccgaa ttgcttcagc
   1021 acccgtttgt cact
```

NPK1
```
        ccg ccaatccggt ggaggaaagg
    301 tgaaatgatt ggatgtggtg cttttggtag ggtttatatg gggatgaatg ttgattctgg
    361 agagttactc gctataaagg aggtttcgat tgcgatgaat ggtgcttcga gagcgagc
    421 acaagctcat gttagagagc ttgaggaaga agtgaatcta ttgaagaatc tctcccatcc
    481 caacatagtg agatatttgg gaactgcaag agaggcagga tcattaaata tattgttgga
    541 atttgttcct ggtggctcaa tctcgtcact tttgggaaaa tttggatcct ccctgaatc
    601 tgttataaga atgtacacca agcaattgtt attagggttg gaatacttgc ataagaatgg
    661 gattatgcac agagatatta agggagcaaa catacttgtt gacaataaag gttgcattaa
    721 acttgctgat tcggtgcat ccaagaaggt tgttgaattg ctactatga ctggtgccaa
    781 gtcaatgaag ggtactccat actggatggc tcccgaagtc attctgcaga ctggccatag
```

FIGURE 16

```
 841 cttctctgct gacatatgga gtgtcggatg cactattatc gaaatggcta caggaaaacc
 901 tccttggagc cagcagtatc aggaggttgc tgctctcttc catataggga caaccaaatc
 961 ccatccccc atcccagagc atctttctgc tgaatcaaag gacttcctat taaaatgttt
1021 gcagaaggaa ccgcacctga ggcattctgc atcaaatttg cttcagcatc catttgttac
1081 a
```

TRANSGENIC PLANTS EXPRESSING A MAPKKK PROTEIN KINASE DOMAIN

This application claims benefit of U.S. provisional application Ser. No. 60/095,938 filed on Aug. 10, 1998.

BACKGROUND OF THE INVENTION

This invention relates to the manipulation of plant gene expression and the production of transgenic plants.

Auxin is an essential plant hormone that regulates diverse processes, such as cell division and elongation, root and leaf development, apical dominance, tropism, and reproduction (Davies, P. J., In: Plant hormones, ed., Davies, P. J., pp. 1–12, Kluwer, Dordrecht, Netherlands, 1995). The auxin response is regulated by a complex signaling network, and reflects a balance between auxin and other synergistical or antagonistical signaling pathways in plant cells (Bellincampi et al., *Plant Cell* 8: 477–487, 1996; Coenen et al., *Trends Plant Sci.* 2: 351–356, 1997). A primary event of auxin action is the activation of many early response genes. Extensive studies of the early response gene promoters have identified several auxin responsive cis-elements and trans-acting factors (Abel et al., *Plant Physiol.* 111: 9–17, 1996; Ulmasov et al., *Science* 276: 1865–1868, 1997). Although genetic approaches have significantly advanced our understanding of auxin action (Walden et al., *Trends Plant Sci.* 1: 335–339, 1996; Leyser, *Curr. Biol.* 8: R305–R307, 1998; Guilfoyle, *Trends Plant Sci.* 3: 205–207, 1998), the molecular mechanisms underlying signal transduction pathways that control auxin responsive transcription remain largely unknown.

In yeast, worms, insects, and mammals, the primary responses to hormone, growth, and stress signals are mediated by a conserved signaling cascade consisting of three protein kinases, the mitogen-activated protein kinase (MAPK), mitogen-activated protein kinase kinase (MAPKK), and mitogen-activated protein kinase kinase kinase (MAPKKK). MAPKKK phosphorylates and activates MAPKK that, in turn, phosphorylates and activates MAPK. The activated MAPK can be translocated into the nucleus where it phosphorylates transcription factors that control gene expression (Herskowitz, *Cell* 80: 187–197, 1995; Kyriakis et al., *J. Biol. Chem.* 271: 24313–24316, 1996). Although many plant MAPK, MAPKK, and MAPKKK homologues have been identified based on sequence conservation and functional complementation in yeast, their precise physiological functions in plants are largely unknown (Hirt, *Trends Biol. Sci.* 2: 11–15, 1997). It also remains unclear whether and how these homologues constitute specific MAPK kinase cascades (Mizoguchi et al., *Trends Biotech.* 15: 15–19, 1997).

Plants are constantly exposed to environmental stimuli that influence their growth and development. Adverse environmental conditions, including heat, salinity, freezing, and drought, greatly compromise plant productivity and reduce crop yield. Genetic approaches have been taken to enhance plant tolerance to stresses through alteration of osmolytes, osmoprotectants, membrane fatty acids, channels, transcription factors, and enzymes that scavenge active oxygen species by transferring or mutating individual stress target genes. A need in the art therefore exists for developing molecular strategies that enable plants to have resistance or tolerance to adverse environmental conditions.

SUMMARY OF THE INVENTION

The invention is based on applicants' discovery that a mitogen-activated protein kinase kinase kinase (MAPKKK) polypeptide, such as NPK1 of tobacco and the ANPs of Arabidopsis, is involved in signaling the activation of stress protective gene transcription, repression of early auxin response gene transcription, and the alteration of seed development. Accordingly, the invention involves methods of genetically engineering plants to produce altered, agronomic, physiological, or developmental changes in plants by expressing a transgene including DNA encoding a kinase domain of a MAPKKK within the tissues of the plants. In particular, it has been found that it is possible to engineer plants that express a recombinant MAPKKK that are resistant to a broad spectrum of stresses (e.g., drought, increased salinity, heat shock, and freezing temperature), that have repressed early auxin gene expression, or that have altered seed development.

In one aspect, the invention therefore features a method for increasing stress resistance or tolerance in a plant. The method, in general, includes the steps of: (a) introducing into plant cells a transgene including DNA encoding a kinase domain of a MAPKKK operably linked to a promoter functional in plant cells to yield transformed plant cells; and (b) regenerating a transgenic plant from the transformed cells, wherein the kinase domain of the MAPKKK is expressed in the cells of the transgenic plant, thereby increasing the level of stress resistance or tolerance in the transgenic plant. In preferred embodiments, the expression of the DNA encoding the kinase domain activates the expression of a stress-inducible gene (e.g., a gene encoding a glutathione S-transferase, an asparagine synthetase, or a heat shock protein). In particular applications, the method is especially useful for providing to a plant resistance or tolerance to an environmental stress. Exemplary environmental stresses include, without limitation, those which occur upon exposure of the transgenic plant to limited or inadequate water availability (e.g., drought conditions), excess salt or osmotic conditions, excess temperature conditions (e.g., heat, cold, or frost), excess light, a pathogen, a chemical (e.g. a metal, herbicides, and pollutants), an oxidative stress, UV light, and wounding. In preferred embodiments, the plant is protected against multiple stress conditions.

In another aspect, the invention features a method for reducing the action of an auxin in a plant. The method includes the steps of: (a) introducing into plant cells a transgene including DNA encoding a kinase domain of a MAPKKK operably linked to a promoter functional in plant cells to yield transformed plant cells; and (b) regenerating a transgenic plant from the transformed cells, wherein the kinase domain of the MAPKKK is expressed in the cells of the transgenic plant, thereby reducing the action of the auxin in the transgenic plant. In preferred embodiments, the expression of the DNA encoding the kinase domain represses the expression of an early-auxin gene (e.g., those which are under the control of a promoter which is substantially identical to the GH3 promoter or a promoter which includes the ER7 element).

In still another aspect, the invention features a method for altering seed development. In particular, the method includes the steps of: (a) introducing into plant cells a transgene including DNA encoding a kinase domain of a MAPKKK operably linked to a promoter functional in plant cells to yield transformed plant cells; and (b) regenerating a transgenic plant from the transformed cells, wherein the kinase domain of the MAPKKK is expressed in the cells of the transgenic plant, thereby altering the development of a seed in the transgenic plant. In preferred embodiments, the expression of the DNA encoding the kinase domain enriches endosperm development, enriches embryo development, or attenuates seed development. In yet other preferred embodiments, the attenuation of the seed development results in a seedless plant (e.g., a seedless fruit or vegetable).

In yet another aspect, the invention features a method for increasing the yield or productivity of a transgenic plant. The method generally includes the steps of: (a) introducing into plant cells a transgene including DNA encoding a kinase domain of a MAPKKK operably linked to a promoter functional in plant cells to yield transformed plant cells; and (b) regenerating a transgenic plant from the transformed cells, wherein the kinase domain of the MAPKKK is expressed in the cells of the transgenic plant, thereby increasing the yield of the transgenic plant.

In related aspects of the invention, the invention features a plant (or plant cell, plant tissue, plant organ, or plant component) including a recombinant transgene capable of expressing a kinase domain of a MAPKKK, wherein the transgene is expressed in the transgenic plant under the control of a promoter that is functional in a plant cell. In preferred embodiments, the transgene includes a kinase domain which is obtained from a plant. In yet other preferred embodiments, the invention features a kinase domain which is obtained from a fungus (e.g., a yeast) or an animal (e.g., a mammal). In still other preferred embodiments, the transgene consists essentially of the kinase domain.

In related aspects, the invention features seeds and cells from a plant which include a recombinant transgene capable of expressing a kinase domain of a MAPKKK.

In still other related aspects, the invention features a vector (e.g., an expression vector) including a promoter functional in plant cells operably linked to a gene encoding a MAPKKK polypeptide and a cell (e.g., a plant cell or a prokaryotic cell such as Agrobacterium) that includes the vector. In preferred embodiments, the gene encodes a polypeptide that consists essentially of a kinase domain of a MAPKKK (e.g., a kinase domain from a plant MAPKKK such as NPK1 or an ANP) or a genetically engineered chimeric polypeptide that includes such a kinase domain.

In general, the kinase domain used in the methods or plants (e.g., transgenic plants or plants that are bred using a transgenic plant) of the invention is generally expressed by itself, as a MAPKKK polypeptide or kinase domain-containing fragment thereof, or as part of a genetically engineered chimeric polypeptide. Useful kinase domains include those that are capable of activating a gene involved in a stress response, repressing early auxin gene expression, or altering seed development. Exemplary kinase domains include, without limitation, those that are substantially identical to the kinase domains of NPK1 or an ANP (e.g., ANP1, ANP2, or ANP3) or AtMEKK1. Preferably, the methods and plants of the invention specifically utilize the kinase domain of NPK1 or ANP1. In other preferred embodiments, a full-length MAPKKK polypeptide or a kinase domain-containing fragment thereof that is substantially identical to any one of NPK1, ANP1, ANP2, or ANP3 is utilized.

The DNA encoding the kinase domain is, in general, constitutively expressed. However, if desired, the kinase domain is inducibly expressed, or such a domain is expressed in a cell-specific, tissue-specific, or organ-specific manner. Moreover, the kinase domain can also be expressed under cycling conditions (e.g., cell cycle or circadian conditions).

Exemplary plants which are useful in the methods of the invention, as well as for generating the transgenic plants (or plant cells, plant components, plant tissues, or plant organs) of the invention, include dicots and monocots, such as sugar cane, wheat, rice, maize, sugar beet, barley, manioc, crucifer, mustard, potato, soybean, sorghum, cassava, banana, grape, oats, tomato, millet, coconut, orange, rye, cabbage, apple, eggplant, watermelon, canola, cotton, carrot, garlic, onion, pepper, strawberry, yam, papaya, peanut, onion, legume, bean, pea, mango, and sunflower.

By "polypeptide" is meant any chain of amino acids, regardless of length or post-translational modification (for example, glycosylation or phosphorylation).

By "substantially identical" is meant a polypeptide or nucleic acid exhibiting at least 40%, preferably 50%, more preferably 80%, and most preferably 90%, or even 95% sequence identity to a reference sequence (for example, the amino acid sequences of the kinase domains or full-length MAPKKK polypeptides of NPK1, ANP1, ANP2, or ANP3 or to their respective nucleic acid sequences (FIGS. 11, 12, 13, 14, 15, and 16; SEQ ID NOS: 7–22). For polypeptides, the length of comparison sequences will generally be at least 16 amino acids, preferably at least 20 amino acids, more preferably at least 25 amino acids, and most preferably 35 amino acids or greater. For nucleic acids, the length of comparison sequences will generally be at least 50 nucleotides, preferably at least 60 nucleotides, more preferably at least 75 nucleotides, and most preferably 110 nucleotides or greater.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, FastA, or PILEUP/ PRETTYBOX programs). Such software matches identical or similar sequences by assigning degrees of homology to various substitutions, deletions, and/or other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By "obtained from" is meant isolated from or having the sequence of a naturally-occurring sequence (e.g., a cDNA, genomic DNA, synthetic DNA, or combination thereof).

By "recombinant" is meant a nucleic acid (e.g., DNA) that, is free of the genes which, in the naturally-occurring genome of the organism from which the nucleic acid of the invention is derived, flank the gene. The term therefore includes, for example, a gene or fragment thereof that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a nucleic acid which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a MAPKKK kinase domain (e.g., NPK1, ANP1, ANP2, or ANP3).

By "reporter gene" is meant a gene whose expression may be assayed; such genes include, without limitation, β-glucuronidase (GUS), luciferase (LUC), chloramphenicol transacetylase (CAT), green fluorescent protein (GFP), and β-galactosidase.

By "a promoter functional in a plant cell" is meant any minimal sequence sufficient to direct transcription in a plant cell. Included in the invention are promoter elements that are sufficient to render promoter-dependent gene expression controllable for cell-, tissue-, or organ-specific gene expression, or elements that are inducible by external signals or agents (for example, light-, pathogen-, wound-, stress-, or hormone-inducible elements or chemical inducers) or elements that are capable of cycling gene transcription; such elements may be located in the 5' or 3' regions of the native gene or engineered into a transgene construct.

By "operably linked" is meant that a gene and a regulatory sequence(s) are connected in such a way as to permit gene expression when the appropriate molecules (for example, transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein, includes, without limitation, algae, cyanobacteria, seeds, suspension cultures, embryos, meristematic regions, callus tissue, leaves, roots, shoots, gametophytes, sporophytes, pollen, and microspores.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a nucleic acid sequence (e.g., a recombinant DNA sequence) which is inserted by artifice into a cell and becomes part of the genome of the organism which develops from that cell. As used herein, the transgenic organisms are generally transgenic plants and the DNA (transgene) is inserted by artifice into the nuclear or plastidic genome.

By "increasing stress resistance or tolerance" is meant mediating a level of endurance, adaptability, or durability to a stress (e.g., a man-made stress, such as pollution, or an environmental stress, such as drought, salinity, and oxidative and temperature stresses) in a transgenic plant which is greater than that exhibited by a control plant (for example, a non-transgenic plant). Preferably, the level of stress resistance or tolerance in a transgenic plant (or transformed plant cell, plant component, plant tissue, or plant organ) of the invention is at least 5%, 10%, or 20% (and preferably 30% or 40%) greater than the tolerance to a stress exhibited in a non-transgenic control plant (or control plant cell, plant component, plant tissue, or plant organ). In other preferred embodiments, the level of stress resistance or tolerance to a stress is 50% greater, 60% greater, and more preferably even 75% or 90% greater than a control plant, with up to 100% above the level of tolerance as compared to a control plant being most preferred. The level of stress resistance or tolerance is measured by conventional methods used to determine plant growth and response to stress. For example, the level of stress tolerance to salinity may be determined by comparing physical features and characteristics (for example, plant height and weight, leaf area, plant water relations, ability to flower, ability to generate seeds, and yield/productivity) of transgenic plants and non-transgenic control plants.

The invention provides a number of important advances and advantages for the protection of plants against environmental stress, such as drought, salt, oxidative damage, and temperature. In addition, the invention provides a means for blocking auxin-inducible gene expression and its concomitant responses affecting plant growth and development. Furthermore, the invention is useful for altering seed development (e.g., for the production of seedless fruits or vegetables), as well as for manipulating endosperm or embryo development. Furthermore, the methods of the invention are advantageous because a kinase domain of MAPKKK is relatively unstable which allows for convenient transgene manipulation, thereby avoiding undesirable side effects Moreover, the invention facilitates an effective and economical means to improve agronomically important traits of plants for tolerating the effects of dehydration, salinity, cold, and heat. The invention provides for increased production efficiency, as well as for improvements in quality and yield of crop plants and ornamentals. Thus, the invention contributes to the production of high quality and high yield agricultural products; for example, fruits, ornamentals, vegetables, cereals, and field crops. Genetically-improved seeds and other plant products that are produced using plants expressing the genes and methods described herein also render farming possible in areas previously unsuitable for agricultural production. The invention further provides a means for mediating the expression of stress-related protective proteins (e.g., glutathione S-transferase, asparagine synthetase, or a heat shock protein) that enable a plant to tolerate the effects of environmental stress. For example, transgenic plants constitutively expressing a kinase domain of a MAPKKK are capable of turning on a plant's stress signal transduction pathway by activating the expression of multiple stress-related proteins, which, in turn, enhances the plant's tolerance to multiple stress conditions. Expression of these gene products therefore obviates the need to express individual stress-related genes as a means to promote plant defense mechanisms against adverse environmental conditions.

Other features and advantages of the invention will be apparent from the following description of the preferred embodiments thereof, and from the claims.

DETAILED DESCRIPTION

The drawings will first be described.

Drawings

FIG. 1A is a panel of photomicrographs showing auxin responses in maize protoplasts. The protoplasts were transfected with plasmid DNA carrying either the "GH3-sGFP" or "CAB5-sGFP" auxin-response reporter construct and incubated without or with auxin. Protoplasts expressing GFP were bright green under UV light. Untransfected and uninduced protoplasts showed only blue and pink autofluorescence.

FIG. 1B is a histogram showing that the GH3 promoter and the ER7 auxin responsive element are regulated in maize protoplasts. The protoplasts were transfected with plasmid DNA carrying GH3-GUS (designated "GH3"), ER7-GUS (designated "ER7"), mutated ER7-GUS (designated "mER7"), or a GUS construct under the transcriptional control of the CaMV 35S minimal (−72) promoter (designated "35Smin"). A construct carrying the maize CAB5 promoter (Ulmasov et al., Science 276: 1865–1868, 1997) fused to the luciferase gene (designated "CAB-LUC") was used as an internal control in each transfection. The protoplasts were incubated without or with auxin. In each treatment the GUS activity of the cell lysate was divided by the LUC activity, thereby normalizing the data for variation in experimental conditions (that is, number of cells, transformation efficiency, and cell viability).

Because of differences in the basal level of expression, GUS/LUC activity of the protoplasts transfected with each construct and incubated without auxin was set to 1. The results shown were the means of triplicate samples±SD. All experiments were repeated two to three times with similar results.

FIG. 2A is a photograph of an autoradiogram showing the expression of different protein kinases in maize protoplasts.

FIG. 2B is a photograph of an autoradiogram showing the phosphorylation activity of different protein kinases.

FIG. 2C is a photomicrograph showing that constitutively active NPK1 represses the auxin-inducible GH3 promoter. Maize protoplasts were co-transfected with the GH3-sGFP reporter and an effector construct carrying various protein kinases as indicated or vector DNA (control), and incubated with auxin to induce the GH3 promoter.

Figure 5:
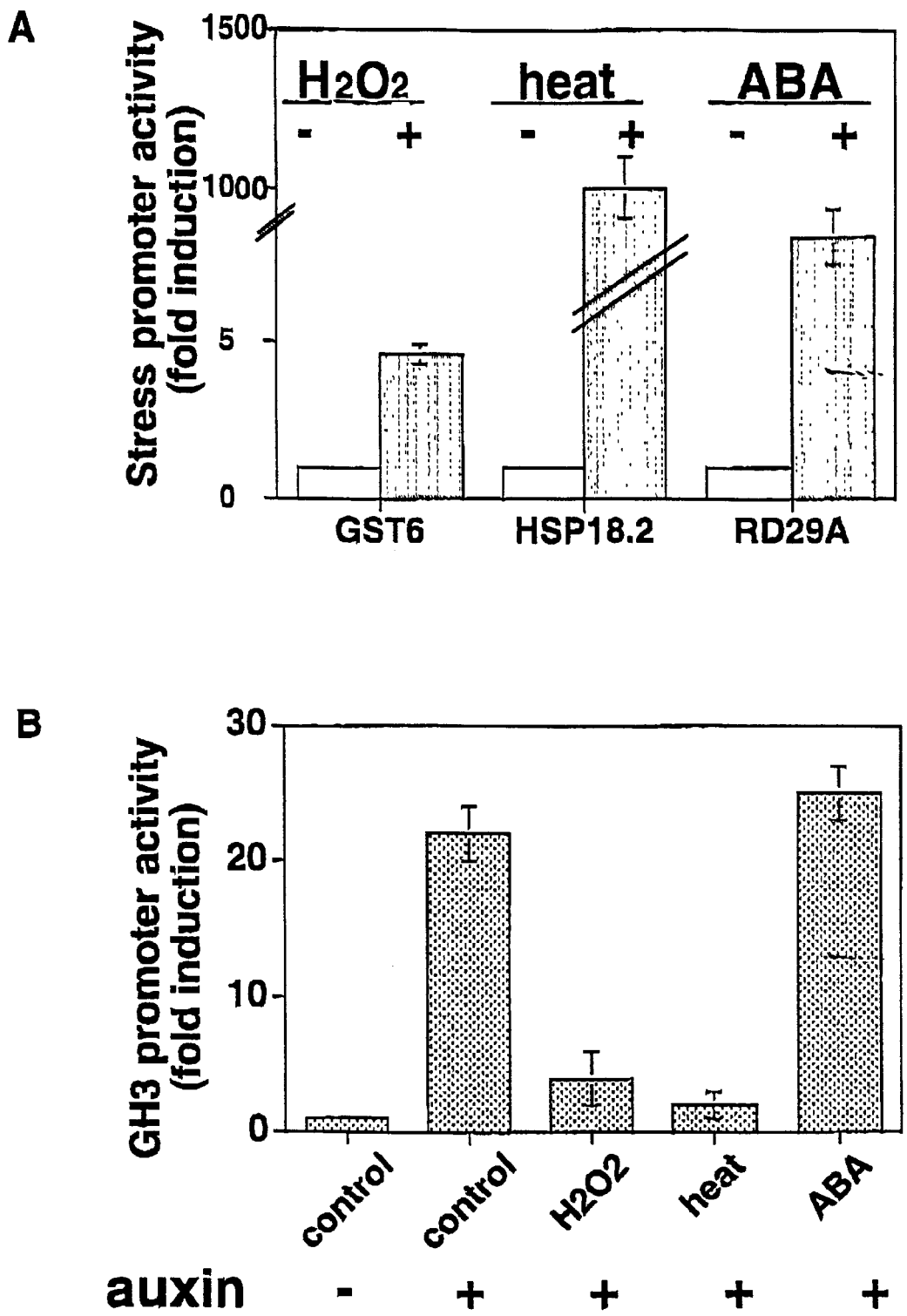

FIG. 2D is a histogram showing that constitutively active NPK1 represses auxin responsive promoters. Maize protoplasts were co-transfected with GH3-GUS (designated "GH3") or ER7-GUS (designated "ER7") reporter and an effector construct carrying the wild-type (designated "NPK1") or mutated (designated "NPK1mut") kinase domain of NPK1, or vector mutated DNA (designated "control"), and incubated with auxin. A CAB-LUC construct was used as an internal control in each transfection to normalize the GUS activity. The GUS/LUC activity of the control protoplasts induced by auxin was set to 100%. The results shown were the means of triplicate samples±SD.

FIG. 2E is a panel showing a photograph of the expression levels of NPK protein and the null mutation of NPK1 at various times during heat shock (upper panel) and a histogram showing the activation of the GH3 promoter in the presence or absence or auxin (lower panel). The wild-type (NPK1) or mutated (NPK1mut) kinase domain of NPK1 was fused to a DHA tag (Sheen, *Science* 274: 1900–1902, 1996) and inserted into a plant expression vector with a heat shock inducible promoter (designated "HSP") (Sheen et al., *Plant J*. 8: 777–784, 1995). Protoplasts were co-transfected with the GH3-GUS reporter and HSP-NPK1 or HSP-NPK1mut effector. CAB-LUC was used as an internal control in each co-transfection to normalize the GUS activity. The expression of the NPK1 or NPK1mut protein was induced at 40° C. for 10, 20, or 60 minutes. The protoplasts from each treatment were divided equally for protein labeling and immunoprecipitation, and for incubation without or with auxin to measure GUS/LUC activity. The GUS/LUC activity of the transfected protoplasts incubated with auxin without heat shock was set to 100%. The results shown were the means of triplicate samples±SD. All experiments were repeated three times with similar results.

FIG. 3A is a schematic diagram showing different NPK1 constructs. The constructs carry the coding region of (1) kinase domain only, (2) $NH_2$-terminus and kinase domain, (3) kinase domain and COOH-terminus, and (4) full-length NPK1 protein.

FIG. 3B is a photograph of an analysis showing the levels of protein expression of the NPK1 constructs (1, 2, 3, and 4) in maize protoplasts.

FIG. 3C is a histogram showing the effect of various NPK1s on the GH3 promoter activity. Maize protoplasts were co-transfected with the GH3-GUS reporter construct and one of the NPK1 constructs (1, 2, 3 or 4) shown in FIG. 3A or vector DNA (control). CAB-LUC was used as an internal control in each transfection to normalize the GUS activity. The GUS/LUC activity of the control protoplasts in the presence of auxin was set to 100%. The results shown were the means of triplicate samples±SD. All experiments were repeated three times with similar results.

FIG. 4A is a panel showing the results of a MAPK in-gel assay (upper panel) and a histogram showing kinase activity (lower panel) of maize protoplasts expressing different MAPKKKs. Protoplasts were transfected with (1) vector DNA for background control; (2) NPK1 kinase domain construct; (3) NPK1 kinase domain mutant construct; (4) full-length NPK1 construct; and (5) CTR1 kinase domain construct. The radioactivity of the 44 kDa putative MAPK band was quantified using a Phosphorimager and normalized to the signal from the background control.

FIG. 4B is a photograph of a gel electrophoretic analysis showing the activity of anti-MAPK immunoprecipitated proteins. Protoplasts were transfected with (1) vector DNA for background control; (2) NPK1 kinase domain construct; and (3) NPK1 kinase domain mutant construct.

FIG. 4C is a panel of gel electrophoretic analyses showing that MAPK phosphatase (MKP1) inactivates NPK1-induced MAPK. Protoplasts were co-transfected with NPK1 and various protein phosphatase (PP) constructs. The transfected protoplasts were divided to determine protein expression level (upper panel), and to perform the kinase in-gel assay (lower panel).

FIG. 4D is a panel of photomicrographs of maize protoplasts showing that MKP1 abolishes the NPK1 repression of the auxin-inducible transcription. Protoplasts were co-transfected with the GH3-sGFP reporter and NPK1, NPK1+MKP1, NPK1+PP1, NPK1+PP2A, or NPK1+PP2C, and incubated in a medium with auxin. All experiments were repeated two to three times with similar results.

FIG. 5A is a histogram showing the $H_2O_2$, heat shock, and ABA responses in designated Arabidopsis protoplasts. Protoplasts were transfected with GST6-LUC (designated "GST6"), HSP18.2-LUC (designated "HSP18.2"), or RD29A-LUC (designated "RD29A") reporter constructs. The transfected protoplasts were divided ($10^5$ per sample) and incubated at 23° C. without (−) or with (+) 200 μM of $H_2O_2$, 38° C. (heat), or 100 μM ABA for 3 hours. The CaMV35S-GUS reporter construct was used as an internal control in each transfection to normalize data for differences in transfection efficiency and cell viability. LUC/GUS was measured as an indicator of the promoter activities. The induction of the HSP18.2 promoter was about 1000 fold, due to extremely low basal expression level. Data are the results of triplicate samples and three independent experiments.

FIG. 5B is a histogram showing that $H_2O_2$ and heat shock suppress the auxin responsive GH3 promoter. Arabidopsis protoplasts were transfected with the GH3-GUS reporter construct, divided ($10^5$ protoplasts per sample), and incubated in the absence (−auxin) or presence of 1 μM NAA (+auxin) and 200 μM of $H_2O_2$, or 100 μM ABA at room temperature or at 38° C. (heat) for 3 hours. CaMV35S-LUC reporter construct was used as an internal control. GUS/LUC was measured as an indicator of GH3 promoter activity. Data are the results of triplicate samples and three independent experiments. Similar results were obtained when GH3-LUC reporter was used.

FIG. 6A is a photograph of an autoradiogram showing the expression of the ANP kinases. Arabidopsis protoplasts were transfected with an effector construct expressing one of the HA-tagged protein kinases: kinase domain of ANP1 (designated "ΔANP1"), kinase domain of ANP2 (designated "ΔANP2"), kinase domain of ANP3 (designated "ΔANP3"), kinase domain of ANP1 mutated in the ATP binding site (designated "ΔANP1m"), and full-length ANP1 (ANP1). The transfected protoplasts were incubated in the presence of [$^{35}$S]-methionine for 4 hours to allow expression and labeling of the effector proteins. The HA-tagged kinases were immunoprecipitated, separated by SDS-PAGE, and detected.

FIG. 6B is a photograph of an autoradiogram showing that ANPs activate two endogenous MAPKs in Arabidopsis. Arabidopsis protoplasts were transfected with the ANP constructs described in FIG. 6A or with a vector (control) and incubated for 4 hours to allow expression. Activity of endogenous MAPKs in the transfected cells was detected by an in-gel assay using myelin basic protein (MBP) as a substrate.

FIG. 6C is a photograph of an autoradiogram showing that ANP1 induced AtMPK3 and AtMPK6 in vivo. Arabidopsis protoplasts were transfected with constructs expressing one of the HA-tagged Arabidopsis MAPKs (designated "AtMPK2 to 7") alone, or co-transfected with another construct expressing HA-tagged ANP1 kinase domain (designated "ΔANP1"). The transfected cells were divided ($10^5$ each) to detect protein levels (upper panel) or to assay the MAPK activity after immunoprecipitation by using MBP as a substrate (lower panel). Stars indicate non-specific bands seen after immunoprecipitation.

FIG. 6D is a photograph of an autoradiogram showing that stresses activate AtMPK3 and ANP1. Arabidopsis protoplasts were transfected with AtMPK3 construct alone or co-transfected with full-length ANP1 (designated "AtMPK3+ΔANP1") or active ANP1 (designated "AtMPK3+ΔANP1"). Cells were incubated for 4 hours to allow protein expression. The protoplasts ($10^5$ each) were treated with 200 μM of $H_2O_2$, 38° C. (designated "heat"), 4° C. (designated "cold"), 1 μM NAA (designated "auxin"), or 100 μM ABA for 15 minutes The AtMPK3 was immunoprecipitated using an anti-HA antibody and assayed for activity by using MBP as a substrate. All data presented in the figure were repeated at least three times with similar results.

Figure 7A:
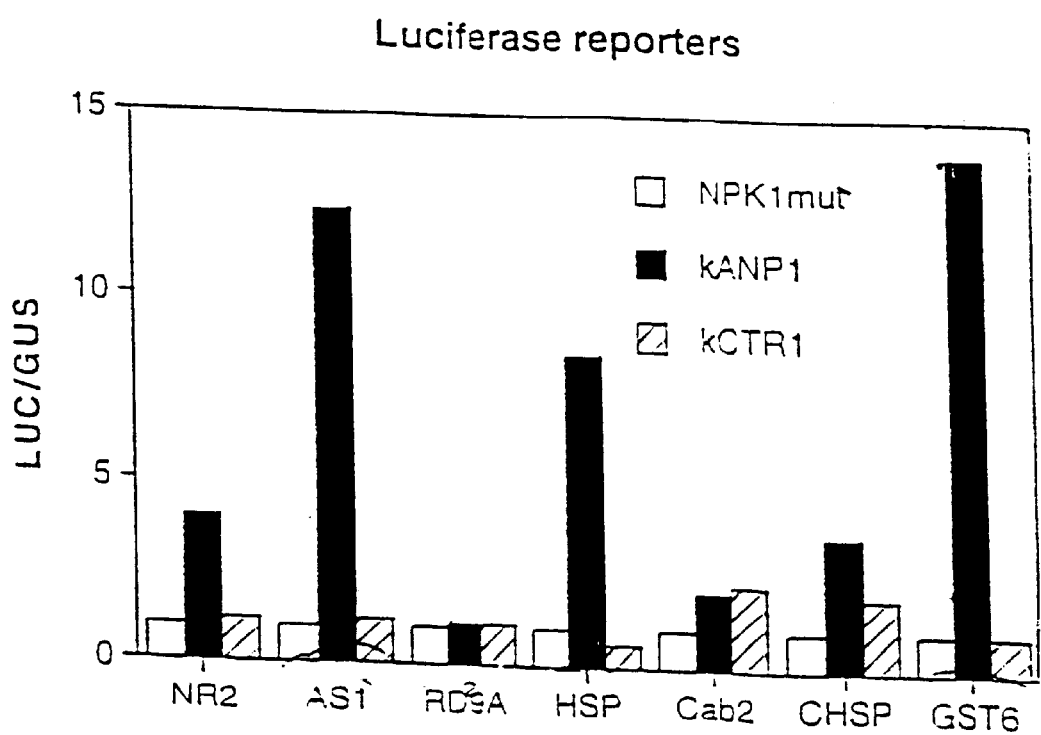

FIG. 7A is a histogram showing the response of different dicot promoters to the constitutive expression of the ANP1 kinase domain in Arabidopsis protoplasts. Protoplasts were co-transfected with either the NR2-LUC (designated "NR2"), AS1-LUC (designated "AS1"), RD29A-LUC (designated "RD29A"), HSP-LUC (designated "HSP"), CAB2-LUC (designated "Cab2"), CHSP-LUC (designated "CHSP"), or GST6-LUC (designated "GST6") reporter gene constructs and an effector construct carrying the wild-type (kANP1) kinase domain, mutated (NPK1mut) kinase domain of NPK1, or the kinase domain of CTR1 (designated "kCTR1"). A 35S NPKmut-GUS construct was used as an internal control in each transfection to normalize the LUC activity. The LUC/GUS activity of the NPK1mut was set to 1. The results shown were the means of triplicate samples±SD.

FIG. 7B is a histogram showing that ANP1 activates stress-inducible promoters. Arabidopsis protoplasts were co-transfected with one of the reporter constructs: GST6-LUC (designated "GST6"), HSP18.2-LUC (designated "HSP18.2"), or RD29A-LUC (designated "RD29A") and one of the effector constructs as described in FIG. 6A, kinase domain of CTR1 (desingated "ΔCTR1"), kinase domain of ASK1 (designated "ΔASK1"), full-length CK1-1 (designated "CK1-1"), or a vector ("control"). The CaMV35S-GUS reporter construct was used as an internal control. Transfected cells were incubated for 6 hours before LUC/GUS was measured as an indicator of the promoter activity. Data are the results of triplicate samples and three independent experiments.

FIG. 7C is a histogram showing that ANPs repress the auxin response. Arabidopsis protoplasts were co-transfected with the GH3-GUS reporter construct and one of the effector constructs as described in FIG. 6A, kinase domain of CTR1 (designated "ΔCTR1"), kinase domain of ASK1 (designated "ΔASK1"), full-length CK1-1 (designated "CK1-1"), or a vector (designated "control"). The CaMV35S-LUC reporter construct was used as an internal control. The transfected protoplasts were incubated for 3 hours to allow effector expression before the induction by 1 μM NAA for 3 hours. GUS/LUC was measured as an indicator of the GH3 promoter activity. Data are the results of triplicate samples and three independent experiments.

FIG. 8A is a histogram showing the seed germination frequencies of different transgenic lines of tobacco expressing NPK1. Wild-type (wt) and three independent transgenic lines (2A, 3B, 4A) were examined. The results shown are the means of triplicate samples, 100 seeds each,±SD.

FIG. 8B is a panel of photomicrographs showing the morphological analysis of wild-type and line 4A transgenic seeds. The wild type (upper panel, labeled 1, 2, 3, and 4) and 4A (lower panel, labeled 5, 6, 7, and 8) seeds were soaked for 24 hours in water. The seeds are shown as a population (1,5), typical single seed (2,6), dissected (3,7), and used for the embryo isolation (4,8). The wild type (3), but not the transgenic (7) seeds, showed abundant endosperm, noticeable after the dissection. At least 10 seeds from each population were analyzed in this study.

FIG. 8C is a photograph of an RNA blot analysis of the NPK1 transgene expression in wild-type and transgenic tobacco. RNA was isolated from two week-old seedlings. The NPK1 probe hybridized with the transgene RNA only. The endogenous NPK1 mRNA was not detected. Ubiqutin (designated "UBQ") expression was used as a control.

FIG. 8D is a photograph of a protein blot analysis of transgene expression. The same amount of proteins (50 mg per lane), extracted from two week-old seedlings, were fractionated in the 12% SDS-PAGE gel and blotted. HA antibody was used to detect HA-tagged transgene proteins. A tobacco transgenic line overexpressing a HA-tagged MEK protein (MEK) was used as a positive control.

Figure 9:
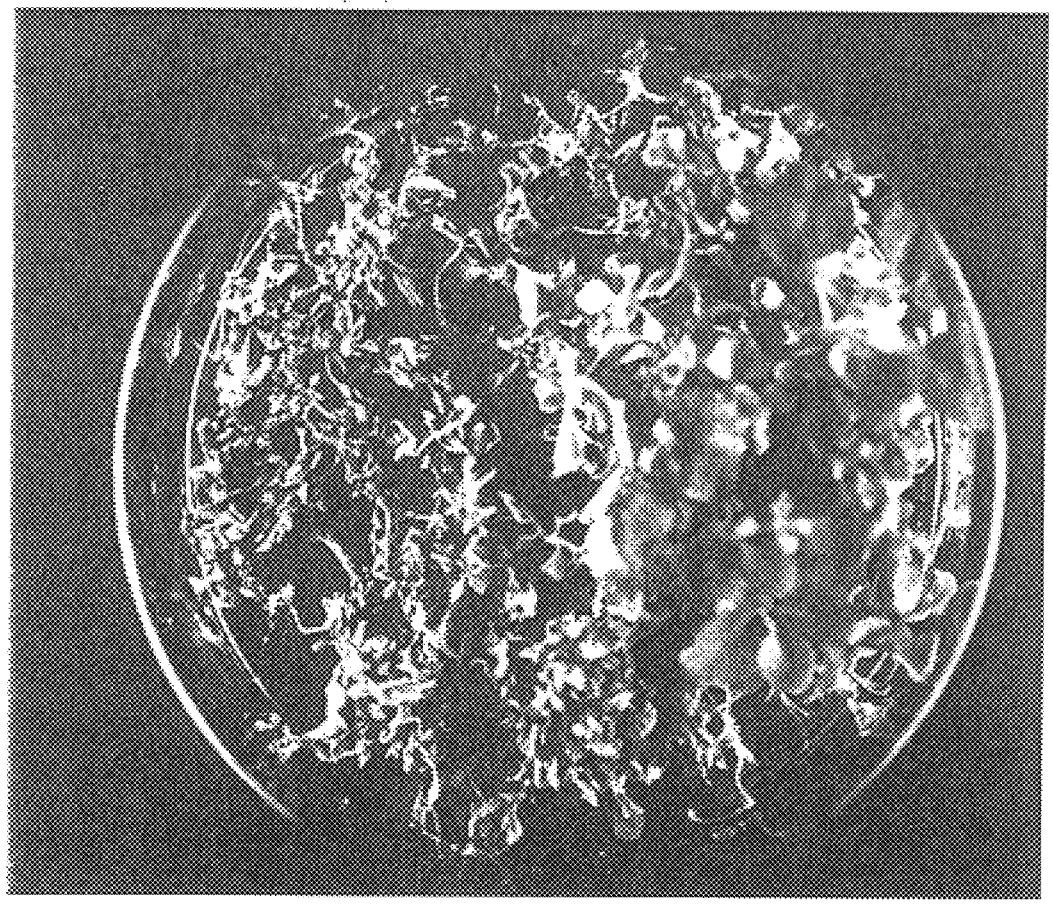

FIG. 9 is a photograph showing the drought resistance of transgenic tobacco plants expressing the NPK1 transgene. Wild type tobacco seedlings are shown on the left; seedlings of transgenic tobacco, line NPK1-A4, are shown on the right.

Figure 10:
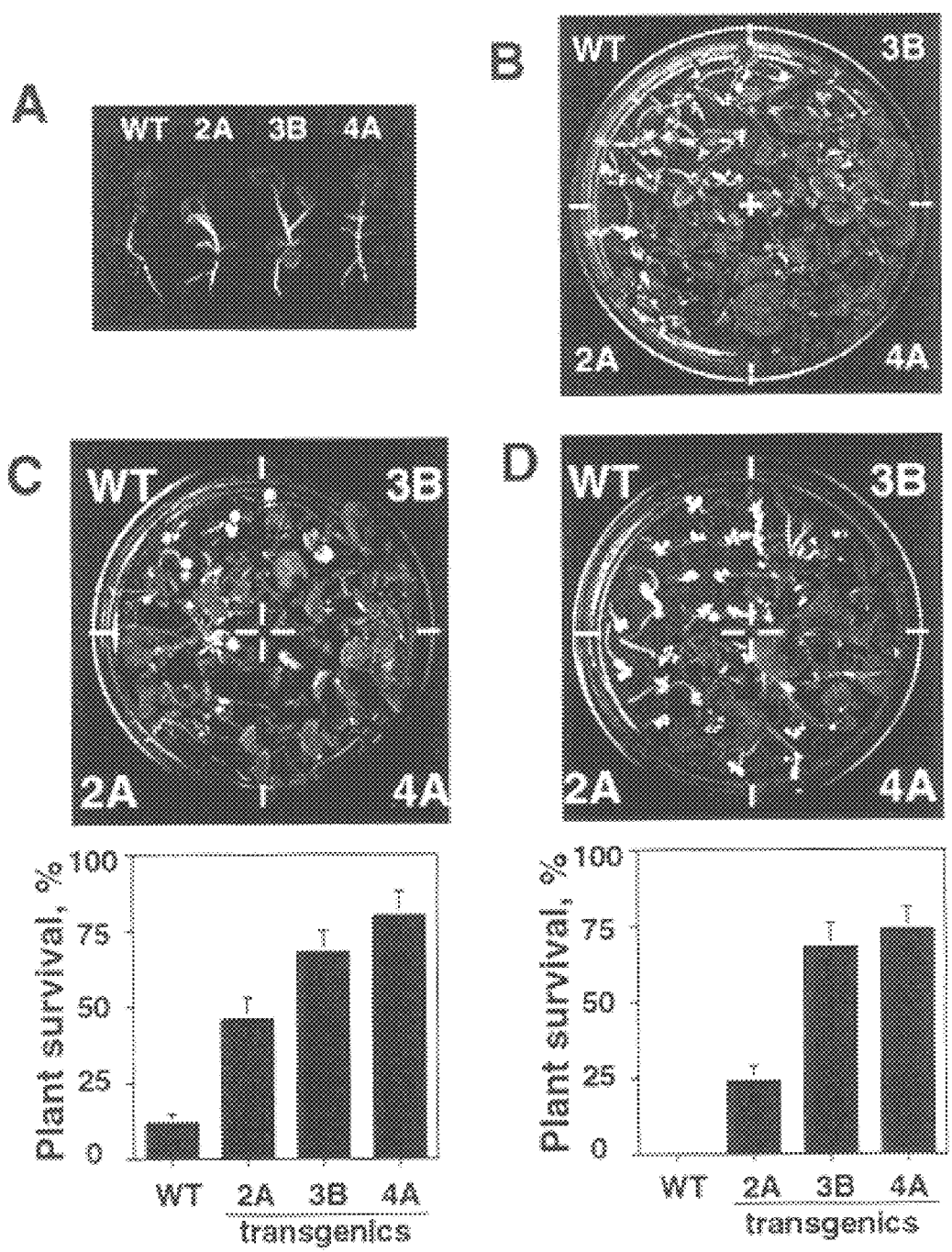

FIG. 10A is a photograph showing the stress tolerance of transgenic tobacco plants expressing NPK1. Wild type (WT) and transgenic (2A, 3B, 4A) plants were germinated and grown on a ¼ MS medium for 3 weeks.

FIG. 10B is a photograph showing the tolerance of transgenic tobacco plants expressing NPK1 to freezing temperature. Wild type (WT) and the transgenic (2A, 3B, 4A) plants were grown on plates for 10 days before freezing temperature treatment (−10° C., 3 hours). The photograph was taken 11 days after treatment.

FIG. 10C is a photograph showing salt stress tolerance of transgenic tobacco plants expressing NPK1. Wild type (WT) and transgenic plants (2A, 3B, 4A) were germinated on ¼ MS medium for 6 days, and then transferred to plates containing 300 mM of NaCl for 3 days. The photograph was taken 11 days after the plants were transferred back to the MS plates without NaCl. The graph represents data from five plates (each plate had 10 plants of each genotype).

FIG. 10D is a photograph showing the tolerance of transgenic tobacco plants expressing NPK1 to heat shock. Wild type (WT) and transgenic (2A, 3B, 4A) plants were grown on plates for 10 days before heat treatment (48° C., 45 minutes). The photograph was taken 18 days after treatment. The graph represents the data from five plates (each plate had 10 plants of each genotype).

FIG. 11 is a diagram showing the alignment of the predicted amino acid sequences of the MAPKKKs: ANP1L, ANP1S, ANP2, ANP3, and NPK1. Kinase domains of these proteins are double-underlined, and are about 268 amino acids in length. Residues that are conserved in three out of the four proteins except (ANP1S) are shown in white letters on a black background. Short conserved stretches (regions A–E) in the four proteins are underlined. Asterisks indicate the consensus sites of phosphorylation by Cdc2 kinase. Only the most carboxy-terminal five amino acid residues of ANP1S that differ from the amino-acid sequence of ANP1L are shown above it (Nishihama et al., Plant J. 12:39–48, 1997).

FIG. 12 shows the amino acid sequence and corresponding nucleotide sequence of ANP1 (SEQ ID NOS: 7 and 8).

FIG. 13 shows the amino acid sequence and corresponding nucleotide sequence of ANP2 (SEQ ID NOS: 11 and 12).

FIG. 14 shows the amino acid sequence and corresponding nucleotide sequence of ANP3 (SEQ ID NOS: 15 and 16).

FIG. 15 shows the amino acid sequence and corresponding nucleotide sequence of NPK1 (SEQ ID NOS: 19 and 20).

FIG. 16 shows the amino acid sequences of the kinase domains of ANP1 (SEQ ID NO: 9), ANP2 (SEQ ID NO: 13), ANP3 (SEQ ID NO: 15), and NPK1 (SEQ ID NO: 21), as well as their corresponding nucleotide sequences (SEQ ID NOS: 10, 14, 16, 22, respectively).

OVERVIEW

As is discussed above, the plant hormone auxin is known to activate many early response genes that are likely responsible for diverse aspects of plant growth and development (Davies, P. J., In: Plant hormones, ed., Davies, P. J., pp. 1–12, Kluwer, Dordrecht, Netherlands, 1995; Abel et al., Plant Physiol. 11 1: 9–17, 1996; Walden et al., Trends Plant Sci. 1: 335–339, 1996). Here we present surprising evidence that a plant MAPK kinase kinase (MPKKK), NPK1 (Banno et al., Mol. Cell Biol. 13: 4745–4752, 1993), which possesses similar structure to the mammalian TAK1 (Yamaguchi et al., Science 270: 2008–2011, 1995) and fly PK92B (Wassarman et al., Gene 169: 283–284, 1996), activates a MAPK cascade that leads to the repression of early auxin response gene transcription. In addition, we show that a mutation in the kinase domain abolished NPK1 activity, and the presence of the COOH-terminal domain diminished the kinase activity. Moreover, the NPK1 effects on the activation of a MAPK and the repression of early auxin response transcription were specifically eliminated by a MAPK phosphatase (Sun et al., Cell 75: 487–493, 1993). We also found that transgenic tobacco plants overexpressing constitutively active NPK1 produced seeds defective in embryo and endosperm development. These results indicated that auxin sensitivity could be balanced by antagonistical signaling pathways (Bellincampi et al., Plant Cell 8: 477–487, 1996; Coenen et al., Trends Plant Sci. 2: 351–356, 1997) that employ a distinct MAPK cascade in higher plants.

In addition, we provide results showing that constitutively active ANP kinase domains (e.g., ANP1, ANP2, and ANP3) induced the expression of a number of plant stress-inducible gene promoters. Moreover, we provide evidence that transgenic tobacco plants having constitutively active NPK1 produced seedlings that were drought-resistant, as well as resistant to the effects of salt. Such plants were also found to be resistant to other stresses such as heat shock and freezing temperatures.

The examples provided below are for the purpose of illustrating the invention, and should not be construed as limiting.

Auxin Responses in Maize Protoplasts

A transient expression system using freshly isolated maize mesophyll protoplasts has been developed to elucidate the molecular mechanisms of intracellular signal transduction and gene expression in higher plants (Sheen, Plant Cell 2: 1027–1038, 1990). This system has been used successfully to study signal transduction pathways stimulated by sugars, light, and the plant hormone abscisic acid (Sheen, EMBO J. 12: 3497–3505, 1993; Jang et al., Plant Cell 6: 1665–1679, 1994; Sheen, Science 274: 1900–1902, 1996; Sheen, Proc. Natl. Acad. Sci. USA 95: 975–980, 1998). To determine whether this system is suitable for the investigation of auxin signaling, we have tested the auxin inducibility of a well-characterized early response gene promoter, GH3 (Hagen et al., Plant Mol. Biol. 17: 567–579, 1991), in maize mesophyll protoplasts. Maize protoplasts transfected with a construct carrying the coding region of a synthetic green-fluorescent protein (sGFP) (Chiu et al., Curr. Biol. 6: 325–330, 1996) driven by the GH3 promoter ("GH3-sGFP") showed bright fluorescence upon induction with different active auxin forms, NAA (FIG. 1A) or IAA (data not shown) at 1 mM, a physiologically relevant concentration. In contrast, we observed that auxin did not affect the expression of a GFP construct ("CAB-sGFP") that was controlled by the maize chlorophyll a/b binding protein gene promoter (CAB5) (Sheen, Supra 2: 1027–1038, 1990) (FIG. 1A).

To confirm the auxin inducibility of the GH3 promoter, we also tested the effect of auxin on the promoter fused to another reporter gene encoding the E. coli β-glucuronidase (GUS) in transfected maize protoplasts. The results from these experiments showed that GUS activity that was controlled by the GH3 promoter was also induced by auxin (FIG. 1B), although the GUS reporter gene generated higher background than the GFP reporter gene in maize cells.

To support the idea that the early auxin responses are conserved in higher plants, we tested an auxin responsive DNA element, ER7 (Ulmasov et al., Science 276: 1865–1868, 1997), which has been found in the majority of early auxin response gene promoters (Abel et al., Plant Physiol. 111: 9–17, 1996; Ulmasov et al., supra, 1997). A complementary pair of synthetic oligonucleotides containing the ER7 element was fused upstream of the GUS gene driven by a 35S minimal promoter. This ER7-GUS construct showed auxin inducibility in maize protoplasts, whereas the 35S minimal promoter was found not to be induced by auxin (FIG. 1B). Moreover, when the ER7 element was mutated, it lost its auxin inducibility completely (FIG. 1B), as previously shown in transfected carrot protoplasts (Ulmasov et al., supra, 1997). These data clearly demonstrated that maize mesophyll protoplasts responded to physiological levels of auxin and that the early auxin responses are likely conserved in monocot and dicot plants.

Constitutively Active NPK1 Represses Auxin-inducible Promoters

To determine whether NPK1 (Banno et al., supra) is involved in auxin signal transduction, we tested the effect of a constitutively active NPK1 on the activity of the GH3 promoter. It has been shown that MAPKKKs consist of a well-conserved kinase domain and putative regulatory domains. Truncated or naturally occurring MAPKKKs carrying only the kinase domain have been shown to have constitutive kinase activity Banno, supra; Nishihama et al., Plant J. 12: 39–48, 1997). The structure of NPK1 is unique as a MAPKKK with the kinase domain located at the NH$_2$-terminus. A similar structure has also been found in the mammalian TAK1 involved in TGF-β signaling (Yamaguchi et al., Science 270: 2008–2011, 1995), and the fly PK92B with an unknown function (Wassarman et al., *Gene* 169: 283–284, 1996). The kinase domain of NPK1 was tagged with two copies of a hemagglutinin (DHA) epitope (Sheen, supra, 1996) and cloned into a plant expression vector with a derivative of the CaMV35S promoter (this promoter is not affected by auxin) and the nos terminator (Sheen, supra, 1993; Sheen, supra, 1996; Sheen, supra, 1998). The NPK1 construct was co-transfected with the GH3-sGFP or GH3-GUS construct into maize protoplasts. The expression of the NPK1 kinase domain in transfected maize protoplasts was confirmed by $^{35}$S-methionine labeling and immunoprecipitation with an anti-HA antibody (FIG. 2A). The kinase activity of the expressed protein was assayed using casein as a universal substrate (FIG. 2B). Surprisingly, the constitutively active NPK1 was found to block auxin activation of the GH3 promoter (FIGS. 2C and 2D).

To show that the kinase activity of NPK1 is necessary for this repression, a null mutation (K109M) was created by site-directed mutagenesis to eliminate the ATP binding site conserved among protein kinases (Sheen, supra, 1996). This mutation was found not to affect the expression of the NPK1 protein (FIG. 2A), but completely abolished the protein kinase activity (FIG. 2B) and the negative effect of NPK1 on the GH3 promoter in the presence of auxin (FIGS. 2C and 2D).

To demonstrate that the inhibitory effect was specific to NPK1, we next tested the effect of another plant MAPKKK, Arabidopsis CTR1, that has been shown to act as a negative regulator of ethylene responses (Kieber et al., *Cell* 72: 427–441, 1993). The kinase domain of CTR1 was expressed and displayed protein kinase activity in maize protoplasts (FIGS. 2A and 2B), but did not block auxin signaling (FIG. 2C). In addition, because NPK1 is a serine/threonine protein kinase, we expressed other constitutively active serine/threonine protein kinases that belong to four different classes (FIG. 2A), and tested their effect on the GH3 promoter. Unlike NPK1, none of the tested protein kinases repressed the auxin-regulated gene expression (FIG. 2C) although they all exhibited protein kinase activities in the system (FIG. 2B). Thus, the effect of NPK1 on auxin signaling was not due to non-specific phosphorylation in plant cells.

In addition to the GH3 promoter, we examined the effect of the constitutively active NPK1 on the well-established auxin responsive DNA element, ER7, that has been described by Ulmasov et al. (supra, 1997). NPK1 was found to completely suppress the auxin inducibility of the auxin responsive element (FIG. 2D). However, the activities of many auxin-insensitive promoters, including the promoters of CAB, actin, ubiquitin, and CaMV35S genes, were not affected by NPK1 (data not shown). Taken together, these results indicated that NPK1 plays an important and specific role in the negative regulation of the auxin response genes.

It remained possible that NPK1 was a positive regulator in auxin signaling and that the overexpression of NPK1 mimicked the repression of the auxin response genes by very high levels of auxin (Hagen et al., supra). To exclude this possibility, we tested the effect of different NPK1 protein levels on the GH3 promoter activity in the absence or presence of auxin. We used a heat shock promoter (Sheen et al., supra, 1995) to control the amount of the NPK1 protein produced by varying the time of heat shock. The null mutation of NPK1 served as a control for the effect of the heat shock. As is shown in FIG. 2E, the expression levels of the constitutively active NPK1 and the null mutant correlated well with the duration of heat shock. The activation of the GH3 promoter was not observed at any level of NPK1 in the absence of auxin, ruling out the possibility that NPK1 could be a positive regulator in auxin signaling. In the auxin treated protoplasts, the reverse correlation between the NPK1 protein levels and the GH3 promoter activity supports the idea that NPK1 acts as a negative regulator in auxin signal transduction (FIG. 2E).

Analysis of the Putative Regulatory Domains of NPK1

One distinct feature of NPK1 is the presence of a short $NH_2$-terminal sequence and a long COOH-terminal region outside the kinase catalytic domain (Banno et al., supra). To investigate the function of regions outside the kinase domain in the NPK1 protein, we created several NPK1 deletions (FIG. 3A) and tested their effect on the GH3 promoter activity. Various deletions of the full-length NPK1, as well as the full-length NPK1, showed similar levels of protein expression in transfected maize protoplasts (FIG. 3B). Deletion of the kinase region alone or the kinase domain plus the short $NH_2$-terminus was found to inhibit the GH3 promoter more strongly than the deletion carrying the kinase domain with the long COOH-terminus or the full-length NPK1 (FIG. 3C).

NPK1 Activates a MAPK

NPK1, as a MAPKKK, is expected to induce a protein phosphorylation cascade resulting in the activation of a MAPK. Although several plant MAPKs have been shown to be induced by stress, hormone, and elicitor signals (Hirt, *Trends Biol. Sci.* 2: 11–15, 1997; Mizoguchi et al., *Trends Biotech.* 15: 15–19, 1997), their activation by a phosphorylation cascade has never been demonstrated in plant cells. To determine whether the expression of the constitutively active NPK1 activates an endogenous MAPK in maize protoplasts, we performed a standard MAPK activity assay (Mizoguchi et al., *Plant J.* 5: 111–122, 1994; Zhang et al., *Plant Cell* 9: 809–824, 1997; Bogre et al., *Plant Cell* 9: 75–83, 1997) with extracts prepared from protoplasts transfected with NPK1 using myelin basic protein (MBP) as a substrate. As shown in FIG. 4A, protoplasts which were transfected with the constitutively active NPK1 had about eight-fold higher 44 kDa kinase activity than protoplasts transfected with the NPK1 null mutation or plasmid DNA carrying no plant genes. This result suggested that the expression of the constitutively active NPK1 resulted in activation of a MAPK. Apparently, a MAPKK was already present in maize protoplasts and sufficient to relay phosphorylation from MAPKKK (NPK1) to the 44 kDa MAPK. The expression of the full-length NPK1 increased the putative MAPK activity only three fold (FIG. 4A). These results are consistent with the observation that the full-length NPK1 has less effect and the null NPK1 protein has no effect on the repression of the GH3 promoter in the presence of auxin (FIGS. 2C, 2D, and 2E; FIG. 3C). As a control, the constitutively active CTR1 also activated an endogenous kinase (FIG. 4A), suggesting the existence of another unrelated MAPK cascade in maize protoplasts. We also observed that the constitutively active CTR1, but not NPK1, could repress ethylene responsive GCC1 enhancer activity more than ten fold in Arabidopsis protoplasts, consistent with the proposed role of CTR1 as a negative regulator in the ethylene signaling pathway (Kieber et al., *Cell* 72: 427–441, 1993; Sheen, unpublished).

To verify that NPK1 expression resulted in the activation of a MAPK, we performed kinase activity assays with the proteins immunoprecipitated with an antibody raised against two conserved domains of a mammalian MAPK. The MAPK activity of the protoplasts transfected with the constitutively active NPK1 was significantly higher than that of the cells transfected with the NPK1 null mutant (FIG. 4B). These data are consistent with the results of the MAPK in-gel assay (FIG. 4A), and demonstrate that tobacco NPK1 can induce a kinase cascade in maize protoplasts that activates an endogenous maize MAPK.

To determine whether the 44 kDa MAPK is involved in the repression of early auxin response genes, we tested the effect of a specific MAPK-phosphatase (MKP) that can inactivate MAPKs. Protein phosphatases that can specifically dephosphorylate/inactivate MAPKs have been reported in a variety of eukaryotes and are evolutionarily conserved (Tonks et al., *Cell* 87: 365–368, 1996). A mouse MKP1 (Sun et al., supra), highly specific to MAPKs, was cloned into the plant expression vector and expressed in maize protoplasts (FIG. 4C). The expression of MKP1 resulted in the complete elimination of the NPK1 effects, including the NPK1-dependent activation of a MAPK (FIG. 4C) and the repression of the auxin-inducibility of the GH3 promoter (FIG. 4D). The results suggest that the activation of the 44 kDa MAPK is necessary for the NPK1 dependent repression of transcription. As controls, the expression of other plant protein phosphatases (PP) that belong to the three serine/threonine classes, PP1, PP2A, and PP2C, did not abolish the activation of MAPK by NPK1 (FIG. 4C) or the repression of the GH3 promoter by NPK1 (FIG. 4D), despite the detection of enhanced PP activities in transfected maize protoplasts (Sheen, supra, 1993; Sheen, supra, 1998) (data not shown). The fact that MKP1 alone does not affect the GH3 promoter (data not shown) supports our current model that a signal(s), antagonizing auxin responses, induces NPK1-like MAPKKKs and leads to the repression of the auxin-inducible transcription.

Stress and Auxin Responses in Arabidopsis Protoplasts

To further elucidate the molecular basis of oxidative stress signaling in plants, we have also showed that an Arabidopsis protoplast transient expression system is useful to investigate multiple stress responses. Three Arabidopsis stress responsive promoters, glutathione S-transferase GST6 (Chen et al., *Plant J.* 10: 995–966, 1996), heat shock HSP18.2 (Takahashi and Komeda, *Mol. Gen. Genet.* 219: 365–372, 1989), and the abscisic acid (ABA) responsive promoter RD29A (Yamaguchi-Shinozaki et al., *Plant Physiol.* 101: 1119–1120, 1993; Ishitani et al., *Plant Cell* 9: 1935–1949, 1997), were fused to the luciferase (LUC) reporter and tested for their responses in transfected mesophyll protoplasts. The GST6, HSP18.2, and RD29A promoters were activated by $H_2O_2$, heat, and ABA, respectively, in protoplasts (FIG. 5A) as demonstrated previously in intact plants (Chen et al., supra; Takahashi and Komeda, supra; Yamaguchi-Shinozaki et al., supra; Ishitani et al., supra). Several GST genes, including GST6, have been shown to be induced by high and toxic concentrations of plant growth hormone auxin, as well as by physiologically inactive auxin analogs, heavy metals, and numerous stresses (Chen et al., supra; Ulmasov et al., *Plant Mol. Biol.* 26: 1055–1064, 1994; Abel and Theologis, *Plant Physiol.* 111: 9–17, 1996; Sitbon and Perrot-Rechenmann, *Physiol. Plantarum* 100: 443–445, 1997; Guilfoyle et al., *Plant Physiol.,* 118: 341–347, 1998, Marrs, *Annu. Rev. Plant Physiol. Plant Mol. Biol.* 47: 127–158, 1996). This non-specific induction of GSTs separates them from other auxin responsive genes that are only induced by low physiological levels of active auxin, and indicates that stress rather than auxin is responsible for the activation of the GST genes.

$H_2O_2$ and Heat Shock Suppress the Auxin Responsive GH3 Promoter $H_2O_2$, heat, and ABA can arrest cell cycle and plant growth (Inzé and Van Montagu, supra; Bolwell and Wojtaszek, supra; Lamb and Dixon, supra; Noctor and Foyer, supra; Leung et al., supra; Cheikh and Jones, *Plant Physiol.* 106, 45–51, 1994; Reichheld et al., *Plant J.* 17: 647–656, 1999), the processes promoted by auxin (Key, *BioEssays* 11: 52–58, 1989; Garbers and Simmons, *Trend Cell Biol.* 4: 245–250, 1994; Walker and Estelle, *Curr. Opinion Plant Biol.* 1: 434–439, 1998; Leyser, *Curr. Biol.* 8: R305–R307, 1998). This suggests a connection between stress and auxin signaling; however, a molecular basis of the crosstalk is unknown. We tested the effects of these stresses on the activity of the auxin responsive promoter, GH3 (Hagen et al., supra; Liu et al., supra). In Arabidopsis protoplasts, physiological concentrations of auxin, 1 $\mu$M NAA (FIG. 5B) or 1 $\mu$M IAA (data not shown), dramatically increased GH3 promoter activity. The kinetics and magnitude of GH3 promoter activation in Arabidopsis protoplasts were comparable to those previously reported in other systems (Hagen et al., supra; Liu et al., supra). Both $H_2O_2$ and heat, but not ABA, severely abolished the auxin response (FIG. 5B). The same stress treatments had no significant effects on the CaMV35S promoter activity as an internal control or on ubiquitin promoter UBQ10 activity as a parallel control (data not shown). The repression of the auxin early response gene promoter is therefore likely due to the activation of a specific stress signaling pathway that is common to $H_2O_2$ and heat, two representative oxidative stress signals (Inze and Van Montagu, supra; Bolwell and Wojtaszek, supra; Lamb and Dixon, supra; Noctor and Foyer, supra). In contrast, the stress hormone ABA did not appear to interfere with auxin signaling in leaf cells.

ANP1 Initiates a Stress MAPK Cascade

In many eukaryotes, the transduction of $H_2O_2$ and heat stress signals is controlled by protein phosphorylation involving MAPKs (Kyriakis and Avruch, *J. Biol. Chem.* 271: 24313–24316, 1996; Tuomainan et al., *Plant J.* 12: 1151–1162, 1997; Gustin et al., *Microbiol. Mol. Biol. Review* 62: 1264–1300, 1998; Morimoto, *Genes Develpm.* 12: 3788–3796, 1998; Morimoto and Santoro, *Nature Bio-Tech.* 16: 833–838, 1998; Schoffl et al., *Plant Physiol.* 117: 1135–1141, 1998). MAPK and immediate upstream activators, MAPKK and MAPKKK, constitute a functionally interlinked MAPK cascade (Kyriakis and Avruch, supra; Tuomainan et al., supra; Gustin et al., supra). Since the activated tobacco MAPKKK, NPK1 (Banno et al., supra), initiated a MAPK cascade that represses auxin early response gene expression (as described herein), we reasoned that this MAPK cascade could also represent a molecular link between oxidative stress and auxin signal transduction. Three Arabidopsis NPK1-like MAPKKKs, ANP1–3, share high homology in both their kinase and regulatory domains (Nishihama et al., *Plant J.* 12: 39–48,1997). The regulatory domains of MAPKKKs interact mostly with upstream regulators, whereas the kinase domain forms a complex with the substrate, a specific MAPKK (Xu et al., *Proc. Natl. Acad. Sci. USA* 92: 6808–6812, 1995; Shibuya et al., *Science* 272: 1179–1182, 1996; Clark et al., *Proc. Natl. Acad. Sci. USA* 95: 5401–5406, 1998; Ichimura et al., *Biochem. Biophys. Res. Comm.* 253: 532–543, 1998; Posas and Saito, *EMBO J.* 17: 1385–1394, 1998; Saitoh et al., *EMBO J.* 17: 2596–2606, 1998; Xia et al., *Genes Develop.* 12: 3369–3381, 1998; Yuasa et al., *J. Biol. Chem.* 273: 22681–22692, 1998). Deletions of the regulatory domains, as a result of genetic manipulations, naturally occurred alternative splicing, or proteolytic cleavage, increase MAPKKK activity (Banno et al., supra; Xu et al., supra, 1995; Shibuya et al., supra, 1996; Clark et al., supra; Ichimura et al., supra. 253: 532–543, 1998; Posas and Saito, supra; Saitoh et al., supra; Xia et al., supra; Yuasa et al., supra; Deak et al., supra).

ANPs Activate Two Endogenous MAPKs

We first verified that ANPs could activate endogenous MAPKs in Arabidopsis. Coding regions of full length (repressed), kinase domain (constitutively active), or mutated (kinase-inactive) ANPs were fused to the haemagglutinin (HA) epitope tag and expressed in Arabidopsis protoplasts (FIG. 6A).

Constitutively active ANPs activated two putative endogenous MAPKs in transfected protoplasts (FIG. 6B). Moreover, a mutation in the ATP binding site abolished, and the presence of the regulatory domains diminished, the ability of ANP1 to activate the putative MAPKs. The sizes of the ANP-activated kinases are similar to those reported for plant MAPKs (Hirt, *Trends Biol. Sci.* 2: 11–15, 1997; Machida et al., *Critic Rev. Plant Sciences* 16: 481–496, 1997; Zhang and Klessig, *Plant Cell* 9: 809–824, 1997; Mizoguchi et al., *Trends BioTech.* 15: 15–19, 1997; Jonak et al., *Cell Mol. Life Sci.* 55: 204–213,1999).

ANPs1 Induce AtMKP3 and AtMPK6 In Vivo

To identify downstream MAPKs of the ANP-mediated MAPK cascade, constitutively active ANP1 was co-transfected with one of six Arabidopsis MAPKs (AtMPKs), representing three different classes (Hirt, supra; Machida et al., supra; Zhang and Klessig, supra; Mizoguchi et al., supra; Jonak et al., supra). The active ANP1 initiated a MAPK cascade that could be assayed by measuring the activity of an individual epitope-tagged AtMPK after immunoprecipitation (FIG. 6C). Constitutively active ANP1 slightly changed the mobility of AtMPK3 and AtMPK6 detected by SDS-PAGE, suggesting phosphorylation of these MAPKs (FIG. 6C, upper panel). Notably, active ANP1 dramatically increased the activity of only these two MAPKs (FIG. 6C, lower panel). Active ANP2 and ANP3, but not another MAPKKK, CTR1 (Kieber et al., *Cell* 72: 427–441, 1993), also induced AtMPK3 and AtMPK6 activity (data not shown), indicating that CTR1 and ANPs activate different MAPK cascades. AtMPK3 and AtMPK6 belong to the class of MAPKs implicated in both stress and pathogen signal transduction in many different plant species (Hirt, supra; Machida et al., supra; Zhang and Klessig, supra; Mizoguchi et al., supra; Jonak et al., supra). The ability of ANPs to activate stress-related MAPKs indicates that ANP-mediated MAPK cascade is involved in stress signaling.

Stresses Activate AtMKP3 and ANP1

To define the stress signals that can regulate the MAPK cascade, HA epitope-tagged AtMPK3 was transfected into Arabidopsis protoplasts, and the protoplasts were then challenged with different stresses. Phosphorylation activity of AtMPK3 was measured after immunoprecipitation with an anti-HA antibody. Several stress signals, including $H_2O_2$ or heat, but not auxin, activated AtMPK3 (FIG. 6D, left). $H_2O_2$ or heat also activated AtMPK6 (data not shown). However, when the full-length ANP1 protein was ectopically expressed, only these two stresses, but not other stress stimuli, could further enhance the activation of AtMPK3 (FIG. 6D, center). The fact that $H_2O_2$ and heat each induced the full-length ANP1 activity to the level of the constitutively active ANP1 (FIG. 6D, right) indicates that ANP1 functions in mediating $H_2O_2$ and heat stress signal transduction. Induction of AtMPK3 by stimuli unrelated to oxidative stress is probably mediated by an ANP-independent pathway (FIG. 6D, left).

ANP1 Activates Stress-Inducible Promoters

To determine whether a plant MAPKKK, such as ANP1 (Nishihama et al. *Plant J.* 12: 39–48, 1997), is involved in stress signal transduction, we have tested the effect of a constitutively active ANP1 kinase domain on the activity of several different dicot promoters. This was achieved by introducing into Arabidopsis protoplasts a transgene construct consisting of the firefly luciferase coding sequence (LUC) under the control of different dicot promoters. The promoters tested were the nitrate reductase, NR2, promoter from Arabidopsis (Lin et al., *Plant Physiol.* 106: 477–484, 1994); the asparagine synthetase, AS1, promoter (Neuhaus et al., *EMBO J.* 16: 2554–2564, 1997); the RD29A Arabidopsis stress-responsive promoter (Ishitani et al., *Plant Cell* 9: 1935–1949, 1997); the Arabidopsis HSP heat shock promoter (Sheen et al., *Plant Journal* 9: 777–784, 1995; Takahashi et al., *Plant J.* 2: 751–761, 1992); the Cab2 promoter (Mitra et al. *Plant Mol. Biol.* 12: 169–179, 1989); the chalcone synthase gene promoter (Feinbaum et al., *Mol. Cell Biol.* 8: 1985–1992, 1988); and the $H_2O_2$-inducible glutathione S-transferase promoter (GST) from Arabidopsis (Chen et al., *Plant J.* 10: 955–966, 1996). The kinase domain of ANP1 was cloned into a plant expression vector with a derivative of the 35S promoter and the nos terminator (Sheen, *Science* 274: 1900–1902, 1996). The ANP1 construct was co-transfected with one of the dicot promoter reporter gene construct and assayed according to standard methods. Surprisingly, the constitutively active ANP1 kinase domain was found to activate the expression of the AS1, HSP, and GST6 promoters (FIG. 7A). Constitutive expression of either the mutated NPK1 kinase domain or the CTR1 kinase domain had no effect on the expression of the dicot reporter genes.

To provide further evidence for the involvement of ANPs in specific stress signaling, we tested the effect of the constitutively active ANP1 on the activity of the GST6, HSP18.2, and RD29A promoters. The active ANP1 could substitute for $H_2O_2$ and heat to induce the GST6 and HSP18.2 promoters respectively, but did not change the expression of the ABA, cold, or drought responsive RD29A promoter (FIG. 7B). The activation of the GST6 and HSP18.2 promoters required ANP kinase activity since a single amino acid mutation in the ATP binding site completely abolished the ANP1 effect on the promoters. However, the activation was not due to non-specific protein phosphorylation because three other Arabidopsis protein kinases, including another constitutively active MAPKKK, CTR1 (Kieber et al., supra), did not affect the promoters' activities. The tested protein kinases were expressed equally well and were at least as active as ANP-like MAPKKKs in transfected cells (as described herein). These results reinforce a role of ANP1 in $H_2O_2$ and heat signal transduction. However, since ANP1-mediated induction of the HSP18.2 promoter was lower than that obtained by heat shock (FIG. 5A), both ANP-dependent and ANP-independent pathways are probably required to fully activate the heat shock promoter. Since oxidative stress can induce heat shock responsive genes (Morimoto, supra; Morimoto and Santoro, supra; Schoffl et al., supra; Banzet et al., *Plant J.* 13: 519–527, 1998; Storozhenko et al., *Plant Physiol.* 118: 1005–1014, 1998; Zhong et al., *Mol. Cell* 2: 101–108, 1998; Landry and Huot, *Biochem Soc. Symp.* 64: 79–89, 1999), active oxygen species generated by heat shock (Inze and Van Montagu, supra; Bolwell and Wojtaszek, supra; Lamb and Dixon, supra; Noctor and Foyer, supra) might be responsible for ANP-dependent activation of the promoter.

ANPs Repress the Auxin Response

To determine whether ANPs can mimic $H_2O_2$ and heat to repress auxin signaling, we tested the effect of the kinases on GH3 promoter activity. Constitutively active ANP1, ANP2, and ANP3, but not other tested protein kinases, effectively suppressed the GH3 promoter induction by auxin (FIG. 7C). The results suggest that Arabidopsis ANPs are orthologs of the tobacco NPK1 that can suppress auxin signaling (as described herein). Thus, similar to $H_2O_2$ and heat, the constitutively active ANPs can repress the auxin inducible promoter and induce expression of the GST and HSP genes (FIGS. 5A, B and FIGS. 7B, C).

Analyses of Transgenic Tobacco Plants Expressing NPK1

To assess the function of NPK1 at a whole plant level, we generated transgenic tobacco plants ectopically overexpressing the constitutively active NPK1. It was anticipated that overexpression of NPK1, as an auxin antagonist, could be lethal. We obtained transgenic plants through three independent transformation experiments. We observed that some seeds from several independent NPK1 transgenic lines never germinated, whereas seeds from the wild type control (FIG. 8A) and many other tobacco lines carrying other transgenes (data not shown) germinated normally. In one line, designated 4A, more than 75% of the seeds did not germinate under any conditions. A closer examination revealed that some transgenic seeds exhibited underdeveloped embryo and endosperm (FIG. 8B). Importantly, the number of defective seeds in each line correlated with the level of transgene expression (FIG. 8D), suggesting that the seed phenotype was due to transgene expression. Although the majority of the transgenic seeds that survived expressed the NPK1 mRNA (FIG. 8C), they produced mostly wild-type looking plants. However, we could not detect the ectopic HA-tagged NPK1 protein in these normal-looking transgenic plants after numerous protein blot analyses, while the control transgenic line expressing the HA-tagged MEK1 showed a strong signal (FIG. 8D). We hypothesize that the truncated NPK1 protein is unstable and cannot accumulate to a level required for causing grossly abnormal growth. This is in agreement with a recent report that a mammalian MAPKKK MEKK1 is degraded rapidly after processing and activation (Widmann et al., *Mol. Cell. Biol.* 18: 2416–2429, 1998). In addition, it was reported that in tobacco cells the NPK1 protein is subjected to a fast turn-over after activation specifically at the end of M phase in the cell cycle (Machida et al., 40th NIBB Conference "Stress responses", 1998), and is detectable at low levels only in fast-growing tissues (Banno et al., supra). Thus, accumulation of NPK1 protein might be tightly regulated in plants. This likely explains why the most dramatic effect of NPK1 during embryogenesis and seed development were observed when rapid cell division occurs and more NPK1 proteins may accumulate to block cell cycle progress. The auxin requirement for embryogenesis in plants has been demonstrated (Mordhorst et al., *Genetics* 149: 549–563 1998). Similarly, ectopic activation of a MAPK cascade disrupts Xenopus embryo development by inducing mitotic arrest specifically at the M phase (Takenaka et al., *Science* 280: 599–602, 1998).

Transgenic Tobacco Plants Expressing NPK1 are Resistant to Drought and Excess Salt Transgenic tobacco plants overexpressing the constitutively active NPK1 were found to be resistant to limited water availability when compared to non-transgenic plants (FIG. 9). In addition, transgenic tobacco seeds constitutively expressing the NPK1 gene were also observed to germinate and grow under high salt conditions (150 mM NaCl), as well as to thrive after exposure to oxidative and heat stresses.

Stress Tolerance of Transgenic Tobacco Plants Ectopically Expressing Active NPK1

GSTs and HSPs encode conjugation enzymes and molecular chaperones, respectively. They play essential roles in detoxification and stabilization of damaged proteins and assisting cell recovery from stresses (Marrs, supra; Morimoto, supra; Morimoto and Santoro, supra; Schoffl et al., supra). Constitutive expression of GSTs or HSPs in transgenic tobacco and Arabidopsis can make plants more resistant to different stresses, such as salt and heat (Tarczynski et al., *Science* 259: 508–510, 1993; Kishor et al. *Plant Physiol.* 108: 1387-1394, 1995; Lee et al. *Plant J.* 8: 603–612, 1995; Ishizaki-Nishizawa et al., *Nature BioTech.* 14: 1003–1006, 1996; Roxas et al., *Nature BioTech.* 15: 988–991, 1997; Prandl et al., *Mol. Gen. Genet.* 258: 269–278, 1998; Jaglo-Ottosen et al., *Science* 280: 104–106, 1998; Liu et al. *Plant Cell* 10: 1391–1406, 1998; Pardo et al., *Proc. Natl. Acad. Sci. USA* 95: 9681–9686, 1998; Pei et al., *Science* 282: 287–290, 1998). Since constitutively active ANP1 induces expression of GST6 and HSP18.2 (FIG. 7B), it is possible that transgenic plants ectopically expressing the active ANP-like protein might be more tolerant to such stresses.

Several transgenic tobacco lines (2A, 3B, 4A), expressing different levels of the constitutively active tobacco ANP ortholog, NPK1 (as described herein), were examined. Phenotypically, the transgenic plant did not differ from wild type plants under normal growth conditions (FIG. 10A). However, transgenic plants grew more vigorously than did the wild type plants in the presence of 150 mM NaCl. In addition, only 12% of the wild type, but 46%, 68%, and 80% of 2A, 3B, and 4A plants, respectively, survived a three-day exposure to high salt (300 mM NaCl) (FIG. 10C). NPK1 Transgenic plants were also observed to be tolerant to a 3 hour freezing temperature treatment of −10° C. (FIG. 10B). We have also tested the sensitivity of NPK1 transgenic plants to heat shock. Exposure to 48° C. heat shock killed all the wild type plants, but 24% of 2A, 68% of 3B, and 74% of 4A plants survived (FIG. 10D). The stress tolerance of these NPK1 transgenic plants was proportional to the level of NPK1 transgene expression (as discussed herein). Thus, similar to tobacco and Arabidopsis overproducing GSTs and HSPs (Tarczynski et al., supra; Kishor et al. supra; Lee et al., supra; Ishizaki-Nishizawa et al., supra; Roxas et al., supra; Prandl et al., supra; Jaglo-Ottosen et al., supra; Liu et al., supra; Pardo et al., supra; Pei et al., supra), the NPK1 transgenic plants were more tolerant to salt and heat than were wild type plants. Although some of the NPK1 transgenic seeds are defective during embryogenesis (as discussed herein) when auxin signaling plays a crucial role (Michalczuk et al., *Phytochem.* 31: 1097–1103, 1992; Ribnicky et al., *Plant Physiol.* 112: 549–558, 1996; Hardtke and Berleth, *EMBO J.* 17: 1405–1411, 1998; Mordhorst et al., *Genetics* 149: 549, 1998; McGovern et al., 9th Arabidopsis Converence, Madison, USA 1998), the absence of obvious growth defects in post-embryonic development of the transgenic plants suggests that the level of NPK1 expression achieved is not deleterious, but rather beneficial in vegetative tissues. The manipulation of this oxidative stress signaling regulator can protect plant cells from diverse environmental stresses, such as heat and high salt. This approach may even be applied for protection from other environmental stresses, such as UV-B, ozone, photooxidation, herbicide, pathogen, drought, and chilling that also involve oxidative stress damage (Green and Fluhr, *Plant Cell* 7: 203–212, 1995; Prasad, *Plant J.* 10: 1017–1026, 1996; Willekens et al., *EMBO J.* 16: 4806–4816, 1997; Chamnongpol et al., *Proc. Natl. Acad. Sci USA* 95: 5818–5823, 1998; Schraudner et al., *Plant J.* 16: 235–245, 1998; Karpinski et al., *Science* 284: 654–657,1999). Thus, modulation of MAPKKK activity, such as ANP activity, in vegetative tissues provides a novel strategy for cross protection from multiple stresses in agriculturally important plants.

Role of MAPKKKs

Recently, the analysis of auxin resistant mutants in Arabidopsis suggested a crucial role of protein degradation in auxin signaling and cell cycle control. For example, several auxin resistant mutants (axr1, tir1) seemed to be caused by defects in protein degradation processes (Leyser, Curr. Biol. 8: R305–R307, 1998). Many auxin-inducible proteins, e.g. SAUR, Aux/IAA, are highly unstable, and some of them function as negative regulators of auxin mediated transcription (Abel et al., Plant Physiol. 111: 9-17, 1996; Guilfoyle, Trends Plant Sci. 3: 205–207, 1998; Ulmasov et al., Plant Cell 9: 1963–1971, 1997). The experiments described herein provide another indication that cell cycle, protein turn-over, and auxin signaling are interconnected.

It has been shown that conserved MAPK cascades mediate numerous vital functions in mammals and yeast, e.g., cell proliferation, cell death, stress responses, through the regulation of gene expression (Herskowitz, Cell 80: 187–197, 1995; Kyriakis et al., J. Biol.Chem. 271: 24313–24316, 1996). Here, we have presented the first demonstration that, in plant cells, a MAPKKK can activate a MAPK cascade involved in specific regulation of gene expression, and act as a negative regulator in the auxin signal transduction pathway. The recent finding of three NPK1-like protein kinases in Arabidopsis (ANPs) (Nishihama et al., Plant J. 12: 39–48, 1997) suggests that this distinct MAPKKK is likely conserved in higher plants. In fact, like NPK1, we have found that the kinase domain of ANP1 specifically suppressed the auxin-inducible GH3 promoter in both maize and Arabidopsis protoplasts.

Moreover, we have presented evidence indicating that ANP-like MPKKKs mediate oxidative stress signal transduction in plants. For example, oxidative stress signals, $H_2O_2$ or heat, can activate the MAPKKK. The active ANPs mimic the oxidative stress signals in inducing stress MAPKs and stress response genes, as well as repressing auxin responsive promoter. Therefore, ANP-mediated MAPK cascade links stress and auxin signaling. The activated cascade might help stressed plants to limit auxin-dependent cell division and cell expansion in order to concentrate on survival needs. ANP proteins are found at high levels in meristematic cells and thought to be involved in cell cycle control (Banno et al., supra; Nishihama et al., supra; Nakashima et al., Plant Cell Physiol. 39: 690–700, 1998; Machida et al., 40th NIBB Conference "Stress responses", 1998). Since activation of the stress-induced MAPK cascades usually leads to stress tolerance, a physiological significance of the ANP-related MAPKKKs might be to protect young dividing cells from harsh environmental conditions that plants face during their lifespan. The protection of dividing tissue from stress damage is crucial for survival because continuous organogenesis from the meristems allows reestablishment of plant life.

Materials and Methods

The above-described results were obtained using the following methods.

Reporter Constructs

The 749 bp soybean GH3 promoter (Hagen et al., Plant Mol. Biol. 17: 567–579, 1991) was fused to a synthetic gene encoding green-fluorescent protein (sGFP) (Chiu et al., Curr. Biol. 6: 325–330, 1996) to visualize the promoter activity. Synthetic ER7 element, TTGTCTCCCAAAGG-GAGACAA (SEQ ID NO: 1), or mutated ER7, TTGTCTC-CCAAAGGGAGAtAA (SEQ ID NO:2) (Ulmasov et al., Science 276: 1865–1868 1997), was inserted in front of the CaMV 35S minimal promoter (–72) (Sheen, EMBO J. 12: 3497–3505, 1993). The synthetic promoters were fused to a GUS-nos gene to create ER7-GUS and mER7-GUS reporter constructs. Three clones of each construct were tested for auxin induction and gave identical results.

Arabidopsis MAPKKKs (ANP1, ANP2, ANP3, and CTR1), MAPKs (AtMPK2 to 7), and serine-threonine protein kinases, ASK1 and CK1-1, were obtained by PCR from an Arabidopsis cDNA library. The kinase-inactive ANP1 mutant (K98M) was generated by PCR using the following primers: TCTCGCCGTCAtgCAGGTTCTGATTGC (SEQ ID NO:3) and GCAATCAGAACCTGcaTGACGGC-GAGAAG (SEQ ID NO:4). The mutation was confirmed by DNA sequencing. All PCR products were tagged with two copies of the hemagglutinin (DHA) epitope, and inserted into a plant expression vector containing the 35SC4PPDK promoter and the nos terminator (as described herein). Three to four independent effector clones were tested and gave identical results.

Effector Constructs

NPK1 and CTR1 were obtained by PCR from tobacco cDNA and an Arabidopsis cDNA library, respectively. NPK1 deletions were generated by PCR. The null NPK1 mutant (K109M) was generated by PCR using the following primers: TACTCGCTATAAtGGAGGTTTCGAT (SEQ ID NO:5) and CGCAATCGAAACCTCCaTTATAGCGAGTA (SEQ ID NO:6). The mutation was confirmed by DNA sequencing. The PCR products, the coding regions of the constitutively active protein kinases from Arabidopsis (CDPK, APK2, ASK2 (Sheen, Science 274: 1900–1902, 1996), CK1-1 (Klimczal et al., Plant Physiol. 109: 687–696, 1995)), and the coding regions of protein phosphatases (mouse MKP1 (Sun et al., Cell 75: 487–493, 1993), maize PP1 (Smith et al., Plant Physiol. 97: 677–683, 1991), maize PP2A (Sheen, EMBO J. 12: 3497–3505, 1993), and Arabidopsis PP2C (Sheen, Proc. Natl. Acad. Sci. USA 95: 975–980, 1998)) were inserted into a plant expression vector containing the 35SC4PPDK promoter, nos terminator, and DHA tag (Sheen, Science 274: 1900–1902, 1996; Sheen, Proc. Natl. Acad. Sci. USA 95: 975–980, 1998). Three to four independent clones were tested in co-transfection experiments with identical results.

Arabidopsis GST6 (Chen et al., supra), HSP18.2 (Takahashi and Komeda, supra), and RD29A (Yamaguchi-Shinozaki and Shinozaki, supra; Ishitani et al., supra), as well as soybean GH3 (Key, supra; Garbers and Simmons, supra; Walker and Estelle, supra; Leyser, supra) promoters were fused to the luciferase gene to create GST6-LUC, HSP18.2-LUC, RD29-LUC, and GH3-LUC reporter constructs, respectively.

Protoplast Transient Expression

The preparation, electroporation, and incubation of etiolated maize mesophyll protoplasts were as described previously (Sheen, Plant Cell 2: 1027–1038, 1990; Sheen, EMBO J. 12: 3497–3505, 1993). In each electroporation, $2 \times 10^5$ protoplasts were transfected with 30 mg of plasmid DNA carrying a reporter construct alone or with 30 mg of plasmid DNA carrying an effector construct or a vector DNA control. The transfected protoplasts were incubated in medium ($5 \times 10^4$/ml) without (–auxin) or with (+auxin) 1 mM NAA for 14 hours in the dark. GFP fluorescence was observed using UV light as described previously (Sheen et al., Plant J. 8: 777–784, 1995). The GUS (Sheen, Plant Cell 2: 1027–1038, 1990) and luciferase (Sheen, Science 274: 1900–1902, 1996) assays were carried out with cell lysates from $10^4$ protoplasts.

Arabidopsis thaliana, ecotype Bensheim, was grown on B5 medium for 4 weeks. The third pair of leaves were cut into 1.0 mm strips and digested overnight in 1% Cellulase R-10, 0.25% Macerozyme R-10, 0.5 M mannitol, 10 mM CaCl$_2$, 20 mM KCl, 10 mM MES, pH 5.7, and 0.1% BSA. Protoplasts were released by gentle shaking, filtered through a 75 μm Nylon mesh, collected by centrifugation, and resuspended in W5 solution (Damm et al., *Mol Gen. Genet.* 217:6, 1989; Abel and Theologis, supra). Before transfection, protoplasts were resuspended in 0.4 M Mannitol, 15 mM MgCl$_2$ and 4 mM MES, pH 5.7, to a density of 10$^6$ protoplasts/ml. Typically 0.2 ml of the protoplast suspension was mixed with 30 to 50 μg of plasmid DNA containing reporter and effector constructs and equal volume of 40% PEG solution (Damm et al., *Mol. Gen. Genet.* 217:6, 1989; Abel and Theologis, supra). The transfected protoplasts were diluted with W5 solution, collected by centrifugation, and resuspended in the incubation solution (0.5 M Mannitol, 20 mM KCl, 4 mM MES, pH 5.7).

Determination of Effector Expression

Transfected maize protoplasts (10$^5$) were incubated for 5 hours with [$^{35}$S]-methionine (200 mCi/ml) before harvesting. The NPK1 protein was less stable than other expressed proteins after long incubation (data not shown). Immunoprecipitation with an anti-HA antibody was performed as described previously (Sheen, *Science* 274: 1900–1902, 1996). The proteins were separated by SDS-PAGE (10%) and visualized by fluorography.

In-Gel Kinase Activity Assay

The transfected protoplasts (10$^5$) were incubated for 5 hours before harvesting. The kinase in-gel assay was performed as described previously (Zhang et al., *Plant Cell* 9: 809–824, 1997).

Immunoprecipitation Kinase Activity Assay

Cell lysates from 10$^5$ transfected protoplasts were used for immunoprecipitation with an anti-ERK (PAC) antibody (Transduction Laboratory) (Sheen, *Science* 274: 1900–1902, 1996). The immunoprecipitated proteins were assayed for MAPK activity using MBP as substrate (Bogre et al., *Plant Cell* 9: 75–83, 1997). The [$^{32}$P]-MBP was separated by SDS-PAGE (15%) and visualized by autoradiography.

Protein Kinase and Phosphatase Activity Assays

Cell lysates from 10$^5$ transfected protoplasts were used for immunoprecipitation with an anti-HA antibody (Sheen, *Science* 274: 1900–1902, 1996) to bring down the HA-tagged protein kinases. The immunoprecipitated proteins were assayed using casein as substrate. The [$^{32}$P]-casein was separated by SDS-PAGE (10%) and visualized by autoradiography. PP1, PP2A, and PP2C activity assays using transfected maize cell extracts were described previously (Sheen, *EMBO J.* 12: 3497–3505, 1993; Sheen, *Proc. Natl. Acad. Sci. USA* 95: 975–980, 1998).

Transgenic Plants

A construct including the 35SC4PPDK promoter (Sheen, *EMBO J.* 12: 3497–3505, 1993; Sheen, *Science* 274: 1900–1902, 1996; Sheen, *Proc. Natl. Acad. Sci. USA* 95: 975–980, 1998), kinase domain of NPK1, DHA tag, and nos terminator was inserted into pART27 binary vector (Gleave, *Plant Mol. Biol.* 20: 1203–1207, 1992). The resulting plasmid was introduced into *Agrobacterium tumefaciens* EHA105, and the transformation was performed with *Nicotiana tabacum* SR1 leaf discs (Chiu et al., *Curr. Biol.* 6: 325–330, 1996). Several kanamycin-resistant plants were selected from three independent transformation experiments. The kanamycin resistance of T1 progeny plants revealed that the three analyzed independent parental transformants contained more than one copy of the transgene. The seeds were examined under a light microscope. RNA blot and protein blot analyses were performed as described previously (Jang et al., *Plant Cell* 9: 5–19, 1997).

Isolation of Sequences Encoding MAPKKK Kinase Domains

The isolation of additional MAPKKK coding sequences, as well as MAPKKK kinase domains, having the ability to regulate auxin responses (or activate stress responses, or alter seed development) in plants is accomplished using standard strategies and techniques that are well known in the art.

In one particular example, the tobacco NPK1 sequences (or Arabidopsis ANP1, ANP2, or ANP3 sequences) described herein may be used, together with conventional screening methods of nucleic acid hybridization screening, to isolate additional sequences encoding MAPKKK polypeptides (or kinase domain-containing fragements thereof), as well as kinase domains of MAPKKK (FIGS. 11, 12, 13, 14, 15, and 16; SEQ ID NOS: 7–22). Such hybridization techniques and screening procedures are well known to those skilled in the art and are described, for example, in Benton and Davis, *Science* 196: 180, 1977; Grunstein and Hogness, *Proc. Natl. Acad. Sci., USA* 72: 3961, 1975; Ausubel et al. *Current Protocols in Molecular Biology*, Wiley Interscience, New York; Berger and Kimmel, *Guide to Molecular Cloning Techniques*, 1987, Academic Press, New York.; and Sambrook et al., *Molecular Cloning: A Laboratory Manual*, Cold Spring Harbor Laboratory Press, New York. In one particular example, all or part of the NPK1 gene (described herein) may be used as a probe to screen a recombinant plant DNA library for genes having sequence identity or similarity to the NPK1 gene or its kinase domain (FIGS. 11, 15, and 16). Hybridizing sequences are detected by plaque or colony hybridization according to the methods described below.

Alternatively, using all or a portion of the amino acid sequence of the kinase domain, one may readily design kinase domain-specific oligonucleotide probes, including kinase domain degenerate oligonucleotide probes (i.e., a mixture of all possible coding sequences for a given amino acid sequence). These oligonucleotides may be based upon the sequence of either DNA strand and any appropriate portion of the kinase domain sequence. General methods for designing and preparing such probes are provided, for example, in Ausubel et al., *Current Protocols in Molecular Biology*, Wiley Interscience, New York; and Berger and Kimmel, *Guide to Molecular Cloning Techniques*, 1987, Academic Press, New York. These oligonucleotides are useful for kinase domain sequence isolation, either through their use as probes capable of hybridizing to kinase complementary sequences or as primers for various amplification techniques, for example, polymerase chain reaction (PCR) cloning strategies. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

As discussed above, kinase domain-specific oligonucleotides may also be used as primers in amplification cloning strategies, for example, using PCR. PCR methods are well known in the art and are described, for example, in *PCR Technology*, Erlich, ed., Stockton Press, London, 1989; *PCR Protocols: A Guide to Methods and Applications*, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, kinase domain sequences may be isolated using the PCR "RACE" technique, or Rapid Amplification of cDNA Ends (see, e.g., Innis et al. (supra)). By this method, oligonucleotide primers based on an kinase domain sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., Proc. Natl. Acad. Sci. USA 85: 8998, 1988.

Confirmation of a sequence's relatedness to the kinase domains of the NPK and ANP MAPKKKs may be accomplished by a variety of conventional methods including, but not limited to, sequence comparison of the gene and its expressed product. In addition, the activity of the gene product may be evaluated according to any of the techniques described.

Once a MAPKKK gene or its kinase domain is identified, it is cloned according to standard methods and used for the construction of plant expression vectors as described below.

Expression Constructs

Those skilled in the field of molecular biology will understand that any of a wide variety of expression systems may be used to provide the recombinant protein. The precise host cell used is not critical to the invention. A MAPKKK polypeptide or its kinase domain may be produced in a prokaryotic host, for example, E. coli, or in a eukaryotic host, for example, Saccharomyces cerevisiae, mammalian cells (for example, COS 1 or NIH 3T3 cells), or any of a number of plant hosts including, without limitation, algae, tree species, ornamental species, temperate fruit species, tropical fruit species, vegetable species, legume species, crucifer species, monocots, dicots, or in any plant of commercial or agricultural significance. Particular examples of suitable plant hosts include, but are not limited to, Conifers, Petunia, Tomato, Potato, Tobacco, Arabidopsis, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Grape, Asparagus, Rice, Maize, Millet, Onion, Barley, Orchard grass, Oat, Rye, and Wheat. In addition, as is discussed below, expression constructs may be expressed in a transgenic plant to turn on the stress signal transduction pathway to enhance plant tolerance to multiple stress conditions.

Materials for expressing these genes are available from a wide range of sources including the American Type Culture Collection (Rockland, Md.); or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I.K., Cell Culture and Somatic Cell Genetics of Plants, Vol I, II, III Laboratory Procedures and Their Applications Academic Press, New York, 1984; Dixon, R. A., Plant Cell Culture-A Practical Approach, IRL Press, Oxford University, 1985; Green et al., Plant Tissue and Cell Culture, Academic Press, New York, 1987; and Gasser and Fraley, Science 244: 1293, 1989.

The method of transformation or transfection and the choice of vehicle for expression of the MAPKKK polypeptide or its kinase domain will depend on the host system selected. Transformation and transfection methods are described, e.g., in Ausubel et al. (supra); Weissbach and Weissbach, Methods for Plant Molecular Biology, Academic Press, 1989; Gelvin et al., Plant Molecular Biology Manual, Kluwer Academic Publishers, 1990; Kindle, K., Proc. Natl. Acad. Sci., U.S.A 87: 1228, 1990; Potrykus, I., Annu. Rev. Plant Physiol. Plant Mol. Biology 42: 205, 1991; and BioRad (Hercules, Calif.) Technical Bulletin #1687 (Biolistic Particle Delivery Systems). Expression vehicles may be chosen from those provided, e.g., in Cloning Vectors: A Laboratory Manual (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above. Other expression constructs are described by Fraley et al. (U.S. Pat. No. 5,352,605).

Most preferably, a MAPKKK polypeptide or its kinase domain is produced by a stably-transfected plant cell line, a transiently-transfected plant cell line, or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned plant gene under the transcriptional control of 5' and 3' regulatory sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Once the desired nucleic acid sequence encoding a MAPKKK polypeptide or its kinase domain is obtained as described above, it may be manipulated in a variety of ways known in the art. For example, where the sequence involves non-coding flanking regions, the flanking regions may be subjected to mutagenesis.

The kinase domain sequence (or a MAPKKK polypeptide or kinase domain-containing fragment thereof), if desired, may be combined with other DNA sequences in a variety of ways. Such a sequence may be employed with all or part of the gene sequences normally associated with itself. In its component parts, a DNA sequence encoding a MAPKKK polypeptide or its kinase domain is combined in a DNA construct having a transcription initiation control region capable of promoting transcription and translation in a host cell.

In general, the constructs will involve regulatory regions functional in plants which provide for modified production of the regulator protein as discussed herein. The open reading frame coding for the regulator protein or functional fragment thereof will be joined at its 5' end to a transcription initiation regulatory region such as the sequence naturally found in the 5' upstream region of the MAPKKK polypeptide or its kinase domain. Numerous other transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, or leaf development.

Regulatory transcript termination regions may also be provided in DNA constructs of this invention as well.

Transcript termination regions may be provided by th DNA sequence encoding the MAPKKK polypeptide or any convenient transcription termination region derived from a different gene source. The transcript termination region will contain preferably at least 1–3 kb of sequence 3' to the structural gene from which the termination region is derived. Plant expression constructs having, for example, a MAPKKK protein kinase domain (e.g., the NPK1 kinase domain) as the DNA sequence of interest for expression may be employed with a wide variety of plant life. Such genetically-engineered plants are useful for a variety of industrial and agricultural applications as discussed herein. Importantly, this invention is applicable to dicotyledons and monocotyledons, and will be readily applicable to any new or improved transformation or regeneration method.

An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., Nature 313: 810, 1985). The CaMV promoter is also highly active in monocots (see, e.g., Dekeyser et al., Plant Cell 2: 591, 1990; Terada and Shimamoto, *Mol. Gen. Genet.* 220: 389, 1990). Moreover, activity of this promoter can be further increased (i.e., between 2–10 fold) by duplication of the CaMV 35S promoter (see e.g., Kay et al., *Science* 236: 1299, 1987; Ow et al., *Proc. Natl. Acad. Sci., U.S.A.* 84: 4870, 1987; and Fang et al., *Plant Cell* 1: 141, 1989). In addition, the a minimal 35S promoter may also be used as is described herein.

Other useful plant promoters include, without limitation, the nopaline synthase promoter (An et al., *Plant Physiol.* 88: 547, 1988) and the octopine synthase promoter (Fromm et al., *Plant Cell* 1: 977, 1989).

For certain applications, it may be desirable to produce the MAPKKK polypeptide or its kinase domain in an appropriate tissue, at an appropriate level, or at an appropriate developmental time. For this purpose, there are an assortment of gene promoters, each with its own distinct characteristics embodied in its regulatory sequences, shown to be regulated in response to the environment, hormones, and/or developmental cues. These include gene promoters that are responsible for heat-regulated gene expression (see, e.g., Callis et al., *Plant Physiol.* 88: 965, 1988; Takahashi and Komeda, *Mol. Gen. Genet.* 219: 365, 1989; and Takahashi et al., *Plant J.* 2: 751, 1992), light-regulated gene expression (e.g., the Arabidopisis Cab2 photosynthetic, leaf specific promoter described by Mitra at el., *Plant Mol. Biol.* 12: 169–179, 1989; the pea rbcS-3A described by Kuhlemeier et al., *Plant Cell* 1: 471, 1989; the maize rbcS promoter described by Schäffner and Sheen, *Plant Cell* 3: 997, 1991; or the cholorphyll a/b-binding protein gene found in pea described by Simpson et al., *EMBO J.* 4: 2723, 1985), hormone-regulated gene expression (for example, the abscisic acid (ABA) responsive sequences from the Em gene of wheat described by Marcotte et al., *Plant Cell* 1: 969, 1989; the ABA-inducible HVA1 and HVA22, and rd29A promoters described for barley and Arabidopsis by Straub et al., *Plant Cell* 6: 617, 1994, Shen et al., Plant Cell 7: 295, 1995; and wound-induced gene expression (for example, of wunI described by Siebertz et al., *Plant Cell* 1: 961, 1989), organ-specific gene expression (for example, of the tuber-specific storage protein gene described by Roshal et al., *EMBO J.* 6: 1155, 1987; the 23-kDa zein gene from maize described by Schernthaner et al., *EMBO J.* 7: 1249, 1988; or the French bean β-phaseolin gene described by Bustos et al., *Plant Cell* 1: 839, 1989; the vegetative storage protein promoter (soybean vspB) described by Sadka et al (*Plant Cell* 6: 737–749, 1994)), cycling promoters (e.g., the Arabidopsis cdc2a promoter described by Hemerly et al., *Proc Natl Acad Sci USA* 89: 3295–3299, 1992), senescence-specific promoters (e.g., the Arabidopsis SAG12 promoter described by Gan et al, *Science:* 270, 1986–1988, 1995), seed-specific promoters (for example, endosperm-specific or embryo-specific promoters), or pathogen-inducible promoters (for example, PR-1 or β-1,3 glucanase promoters).

Plant expression vectors may also optionally include RNA processing signals, e.g, introns, which have been shown to be important for efficient RNA synthesis and accumulation (Callis et al., *Genes and Dev.* 1: 1183, 1987). The location of the RNA splice sequences can dramatically influence the level of transgene expression in plants. In view of this fact, an intron may be positioned upstream or downstream of a MAPKKK polypeptide or its kinase-domain encoding sequence in the transgene to modulate levels of gene expression.

In addition to the aforementioned 5' regulatory control sequences, the expression vectors may also include regulatory control regions which are generally present in the 3' regions of plant genes (Thornburg et al., *Proc. Natl. Acad. Sci. U.S.A.* 84: 744, 1987; An et al., *Plant Cell* 1: 115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 µg/mL (kanamycin), 20–50 µg/mL (hygromycin), or 5–10 µg/mL (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) Agrobacterium-mediated transformation (*A. tumefaciens* or *A. rhizogenes*) (see, e.g., Lichtenstein and Fuller, In: Genetic Engineering, vol 6, P W J Rigby, ed, London, Academic Press, 1987; and Lichtenstein, C. P., and Draper, J., In: *DNA Cloning*, Vol II, D. M. Glover, ed, Oxford, IRI Press, 1985)), (2) the particle delivery system (see, e.g., Gordon-Kamm et al., *Plant Cell* 2: 603, 1990); or BioRad Technical Bulletin 1687, supra), (3) microinjection protocols (see, e.g., Green et al., supra), (4) polyethylene glycol (PEG) procedures (see, e.g., Draper et al., *Plant Cell* Physiol. 23: 451, 1982; or e.g., Zhang and Wu, *Theor. Appl. Genet.* 76: 835, 1988), (5) liposome-mediated DNA uptake (see, e.g., Freeman et al., *Plant Cell Physiol.* 25: 1353, 1984), (6) electroporation protocols (see, e.g., Gelvin et al., supra; Dekeyser et al., supra; Fromm et al., *Nature* 319: 791, 1986; Sheen, Plant Cell 2: 1027, 1990; or Jang and Sheen, *Plant Cell* 6: 1665, 1994), and (7) the vortexing method (see, e.g., Kindle supra). The method of transformation is not critical to the invention. Any method which provides for efficient transformation may be employed. As newer methods are available to transform crops or other host cells, they may be directly applied.

The following is an example outlining one particular technique, an Agrobacterium-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of Agrobacterium, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned kinase domain of a MAPKKK (or a MAPKKK polypeptide or a kinase-containing fragment thereof) construct under the control of the nos promoter and the nopaline synthase terminator and carrying a selectable marker (for example, kanamycin resistance) is transformed into Agrobacterium. Transformation of leaf discs (for example, of tobacco or potato leaf discs), with vector-containing Agrobacterium is carried out as described by Horsch et al. (*Science* 227: 1229, 1985). Putative transformants are selected after a few weeks (for example, 3 to 5 weeks) on plant tissue culture media containing kanamycin (e.g. 100 µg/mL). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less medium and grown in a greenhouse. Kanamycin-resistant progeny are selected by sowing surfaced sterilized seeds on hormone-free kanamycin-containing media. Analysis for the integration of the transgene is accomplished by standard techniques (see, for example, Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

In addition, if desired, once the recombinant MAPKKK polypeptide or its kinase domain is expressed in any cell or in a transgenic plant (for example, as described above), it may be isolated, e.g., using affinity chromatography. In one example, an anti-MAPKKK polypeptide antibody (e.g., produced as described in Ausubel et al., supra, or by any standard technique) may be attached to a column and used to isolate the polypeptide. Lysis and fractionation of MAPKKK-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, Laboratory Techniques In Biochemistry And Molecular Biology, eds., Work and Burdon, Elsevier, 1980).

Engineering Stress-Protected Transgenic Plants

As discussed above, because constitutive MAPKKK activity has been found to activate stress-inducible gene promoters such as GST6 (Chen et al., *Plant J.* 10: 955–966, 1996), HSP 18.2 (Sheen et al., *Plant Journal* 9: 777–784, 1995; Takahashi et al., *Plant J.* 2: 751–761, 1992), and AS1 (Neuhaus et al., *EMBO J.* 16: 2554–2564, 1997), constructs designed for the expression of a kinase domain of a MAPKKK are useful for generating transgenic plants having an increased level of tolerance to environmental stress. To achieve such tolerance, it is important to express a kinase domain at an effective level. For example, the Cab and RbcS gene promoters are especially useful for the expression of a kinase domain in leaves; and the 35S CaMV(–90) promoter is useful for the expression of the kinase domain in the roots of a plant. Evaluation of the level of stress protection conferred to a plant by expression of a DNA sequence expressing a kinase domain of a MAPKKK polypeptide is determined according to conventional methods and assays, for example, as described below.

Salt or Osmotic Stresses

In one working example, tissue-specific expression of a kinase domain of a MAPKKK, for example, the NPK1 kinase domain gene, is used in tomato to enhance salt stress tolerance. For example, a plant expression vector is constructed that contains an NPK1 protein kinase domain sequence expressed under the control of a root specific promoter (for example, the 35S CaMV minimal promoter). This expression vector is then used to transform tomato according to standard methods (for example, those described herein). To assess salt tolerance, transformed tomato plants and appropriate controls are evaluated according to methods described in Lilus et al. (*BioTechnology* 14: 177, 1996) and Tarczynski et al. (*Science* 259: 508, 1993). Transgenic seeds containing the gene are germinated in the presence of various salt or osmotically active solutions to determine whether transgenic seeds demonstrate increased tolerance or resistance to salt stress. Seedlings can also be grown in hydroponic systems and challenged with salt or agents of differing osmotic potentials at different, or all, developmental stages in order to assess the response of a MAPKKK kinase domain-expressing plants to these stresses. Growth and physiological measurements are used to document the differences. Transformed tomato plants having an increased level of salt tolerance relative to control plants are taken as being useful in the invention.

Drought

Transgenic plants expressing a recombinant MAPKKK kinase domain are also assayed for tolerance to drought. Such analyses are preferably done in artificial environments to simulate drought or limited water conditions. In addition, transgenic seeds may be planted outside during times when the natural environment would impose the stress.

Cold

To demonstrate whether kinase domain expression can confer increased germination ability under cool conditions, transgenic seeds expressing a recombinant kinase domain of a MAPKKK polypeptide are germinated under conditions similar to the standard cold germination tests used in the seed industry. Alternatively, transgenic seeds expressing such a kinase domain are planted under cool seed bed conditions made cool by artificial environments or naturally cool seed beds in the field. Additionally, plants expressing the kinase domain are challenged during the seed development period for cool night time temperatures to demonstrate decreased inhibition of leaf or canopy activity as a result of cold stress during this time of crop development. Young transgenic seedlings are grown at low temperature, such as about 15° C., during the light and dark period. The expression of a recombinant kinase domain in these seedlings not only allows for increased growth, but also allows the seedlings to become photosynthetic under such conditions, as well as to survive and grow.

Frost or Freeze

Transgenic plants expressing a recombinant MAPKKK kinase domain are also assayed for increased freezing tolerance at the seedling stage as well as late season periods. These assays are preferably done in artificial environments to simulate frost or freeze events. In addition, transgenic seeds may be planted outside during times when the natural environment would impose the stress, e.g., at times when frost is present.

High Heat

Transgenic plants expressing a recombinant MAPKKK kinase domain are also assayed in artificial environments or in the field in order to demonstrate that the transgene confers resistance or tolerance to heat.

Oxidative Stress

Oxidative stress is a major cause of damage in plants exposed to stressful environmental conditions. Oxidative stress results from the cellular damage caused by reactive oxygen species that are generated in cells. These reactive oxygen molecules can damage membranes, proteins, and nucleic acids. Transgenic plants that express a recombinant kinase domain of a MAPKKK are analyzed for the ability to improve resistance to oxidative stress.

Chemical Stress

Transgenic plants expressing a recombinant kinase domain of a MAPKKK are assayed in artificial environments or in the field to demonstrate that the transgene confers resistance or tolerance to chemicals (e.g., herbicides, ozone, or pollutants) or metals (e.g., copper or zinc). Transgenic plants having an increased ability to grow in the presence of higher concentrations of the toxic compound, as compared to non-transgenic plants, are useful in the invention.

Engineering Transgenic Plants Having Increased Yield/Productivity

To test the ability of the genes and domains described herein to improve crop yield or productivity, seeds of transgenic plants expressing a recombinant kinase domain of a MAPKKK are planted in test plots, and their agronomic performance is compared to standard plants using techniques familiar to those of skill in the art. Optionally included in this comparison are plants of similar genetic background without the transgene. A yield benefit is observed and plants exhibiting the increased yield are advanced for commercialization.

In addition, transgenic plants expressing a recombinant kinase domain are field tested for agronomic performance under conditions, including, but not limited to, limited or inadequate water availability. When compared to nontransgenic plants, transgenic plants expressing the kinase domain exhibit higher yield than their nontransgenic counterparts under non-optimal growing conditions.

Engineering Transgenic Plants Having Altered Seed Development

Constitutive expression of a recombinant kinase domain of a MAPKKK is useful for the production of seedless fruits and vegetables (e.g. watermelon, grape, tomato, and eggplant). Alternatively, by using a cycling promoter (e.g., a cyclin A or cyclin D promoter), expression of a recombinant MAPKKK or its kinase domain can be used to promote cell division resulting in the production of larger seeds. Furthermore, expression of a kinase domain under the control of an embryo- or endosperm-specific promoter can be used to control embryo or endosperm development (for example, the production of more endosperm and little or no embryo; or for the production of a larger embryo, but little or no endosperm).

Use

The invention described herein is useful for a variety of agricultural and commercial purposes including, but not limited to, improving resistance or tolerance to stress, increasing crop yields, improving crop and ornamental quality, and reducing agricultural production costs. In particular, ectopic expression of a kinase domain of a MAPKKK polypeptide (or a MAPKKK polypeptide or a kinase domain-containing fragment thereof (FIGS. 11, 12, 13, 14, 15, and 16; SEQ ID NOS: 7–22) in a plant cell provides resistance to environmental stress and can be used to protect plants from adverse conditions that reduces plant productivity and viability. The invention therefore provides resistance to a variety of adverse environmental stresses to plants, especially crop plants, most especially crop plants such as tomato, potato, cotton, pepper, maize, wheat, rice, and legumes such as soybean, or any crop plant that is susceptible to an adverse stress. For example, transgenic maize and soybean may be genetically engineered to express a kinase domain of a MAPKKK (e.g., NPK1 or an ANP such as ANP1, ANP2, or ANP3) according to standard methods, such as those described in Adams et al. (U.S. Pat. No. 5,550,318) and Collins et al. (U.S. Pat. No. 5,024,944). Methods for transforming wheat with such genes are described in Fry et al. (U.S. Pat. No. 5,631,152).

OTHER EMBODIMENTS

The invention further includes the use of analogs of any naturally-occurring MAPKKK polypeptide. Analogs can differ from the naturally-occurring kinase domain by amino acid sequence differences, by post-translational modifications, or by both. Analogs of the invention will generally exhibit at least 40%, more preferably 50%, and most preferably 60% or even having 70%, 80%, or 90% identity with all or part of a naturally-occurring kinase domain amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring kinase domain polypeptide by alterations in primary sequence. These include genetic variants, both natural and induced (for example, resulting from random mutagenesis by irradiation or exposure to ethyl methylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., $\beta$ or $\gamma$ amino acids.

In addition, the invention also includes kinase domain fragments. As used herein, the term "fragment," means at least 50 contiguous amino acids, preferably at least 130 contiguous amino acids, more preferably at least 160 contiguous amino acids, and most preferably at least 190 to 230 or more contiguous amino acids. Fragments of kinase domain polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events). In preferred embodiments, a kinase domain fragment (e.g., a fragment of NPK1, ANP1, ANP2, or ANP3) is capable of activating the transcription of a stress protective gene, repressing the transcription of an early auxin response gene transcription, or altering seed development. Methods for evaluating such activity are described herein.

All publications and patent applications mentioned in this specification are herein incorporated by reference to the same extent as if each independent publication or patent application was specifically and individually indicated to be incorporated by reference.

What is claimed is:

1. A method for increasing stress resistance or tolerance in a plant, said method comprising the steps of:
   (a) introducing into plant cells a DNA construct comprising a DNA sequence encoding a constitutively active mitogen-activated protein kinase kinase kinase (MAPKKK), wherein said DNA sequence is operably linked to a promoter functional in plant cells to yield transformed plant cells, and wherein the DNA sequence encoding the constitutively active MAPKKK is selected from the group consisting of
      (I) a DNA sequence encoding a polypeptide of SEQ ID NO:7, 11, 15, or 19, and
      (ii) a DNA sequence encoding a polypeptide having at least 90% sequence identity to the polypeptide of (i), wherein said polypeptide retains the MAPKKK activity; and
   (b) regenerating a transgenic plant from said transformed plant cells, wherein said constitutively active MAPKKK is expressed in the cells of said transgenic plant at levels sufficient to induce stress resistance or tolerance in said transgenic plant.

2. The method of claim 1, wherein the expression of said DNA encoding said constitutively active MAPKKK activates the expression of a stress-inducible gene.

3. The method of claim 2, wherein the stress-inducible gene comprises a glutathione S-transferase promoter, an ASI promoter, or a heat shock promoter.

4. The method of claim 1, wherein said plant further exhibits increased resistance or tolerance to a pathogen.

5. The method of claim 1, wherein said stress comprises exposure of said transgenic plant to drought conditions, salt stress conditions, freezing temperatures, heat stress conditions or an oxidative stress conditions.

6. The method of claim 1, wherein said plant is protected against multiple stress conditions.

7. The method of claim 1, wherein said DNA encoding said constitutively active MAPKKK is constitutively expressed.

8. The method of claim 1, wherein said DNA encoding said constitutively active MAPKKK is inducibly expressed.

9. The method of claim 1, wherein said DNA encoding said constitutively active MAPKKK is expressed in a cell-specific, tissue-specific, or organ-specific manner.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 1
ttgtctccca aagggagaca a                                         21

<210> SEQ ID NO 2
<211> LENGTH: 21
```

```
<212> TYPE: DNA
<213> ORGANISM: Artificial Sequence
<220> FEATURE:
<223> OTHER INFORMATION: Oligonucleotide primer

<400> SEQUENCE: 2
ttgtctccca aagggagata a                                              21

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 3
tctcgccgtc atgcaggttc tgattgc                                        27

<210> SEQ ID NO 4
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 4
gcaatcagaa cctgcatgac ggcgagaag                                      29

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 5
tactcgctat aatggaggtt tcgat                                          25

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 6
cgcaatcgaa acctccatta tagcgagta                                      29

<210> SEQ ID NO 7
<211> LENGTH: 661
<212> TYPE: PRT
<213> ORGANISM: Arabidopsis thaliana

<400> SEQUENCE: 7

Gly Ser Val Arg Arg Ser Leu Val Phe Arg Pro Ser Ser Asp Asp Asp
 1               5                  10                  15

Asn Gln Glu Asn Gln Pro Pro Phe Pro Gly Val Leu Ala Asp Lys Ile
            20                  25                  30

Thr Ser Cys Ile Arg Lys Ser Lys Ile Phe Ile Lys Pro Ser Phe Ser
        35                  40                  45

Pro Pro Pro Pro Ala Asn Thr Val Asp Met Ala Pro Pro Ile Ser Trp
    50                  55                  60

Arg Lys Gly Gln Leu Ile Gly Arg Gly Ala Phe Gly Thr Val Tyr Met
65                  70                  75                  80
```

```
Gly Met Asn Leu Asp Ser Gly Glu Leu Leu Ala Val Lys Gln Val Leu
                 85                  90                  95

Ile Ala Ala Asn Phe Ala Ser Lys Glu Lys Thr Gln Ala His Ile Gln
            100                 105                 110

Glu Leu Glu Glu Glu Val Lys Leu Leu Lys Asn Leu Ser His Pro Asn
        115                 120                 125

Ile Val Arg Tyr Leu Gly Thr Val Arg Glu Asp Asp Thr Leu Asn Ile
    130                 135                 140

Leu Leu Glu Phe Val Pro Gly Gly Ser Ile Ser Ser Leu Leu Glu Lys
145                 150                 155                 160

Phe Gly Pro Phe Pro Glu Ser Val Val Arg Thr Tyr Thr Arg Gln Leu
                165                 170                 175

Leu Leu Gly Leu Glu Tyr Leu His Asn His Ala Ile Met His Arg Asp
            180                 185                 190

Ile Lys Gly Ala Asn Ile Leu Val Asp Asn Lys Gly Cys Ile Lys Leu
        195                 200                 205

Ala Asp Phe Gly Ala Ser Lys Gln Val Ala Glu Leu Ala Thr Met Thr
    210                 215                 220

Gly Ala Lys Ser Met Lys Gly Thr Pro Tyr Trp Met Ala Pro Glu Val
225                 230                 235                 240

Ile Leu Gln Thr Gly His Ser Phe Ser Ala Asp Ile Trp Ser Val Gly
                245                 250                 255

Cys Thr Val Ile Glu Met Val Thr Gly Lys Ala Pro Trp Ser Gln Gln
            260                 265                 270

Tyr Lys Glu Val Ala Ala Ile Phe Phe Ile Gly Thr Thr Lys Ser His
        275                 280                 285

Pro Pro Ile Pro Asp Thr Leu Ser Ser Asp Ala Lys Asp Phe Leu Leu
    290                 295                 300

Lys Cys Leu Gln Glu Val Pro Asn Leu Arg Pro Thr Ala Ser Glu Leu
305                 310                 315                 320

Leu Lys His Pro Phe Val Met Gly Lys His Lys Glu Ser Ala Ser Thr
                325                 330                 335

Asp Leu Gly Ser Val Leu Asn Asn Leu Ser Thr Pro Leu Pro Leu Gln
            340                 345                 350

Ile Asn Asn Thr Lys Ser Thr Pro Asp Ser Thr Cys Asp Asp Val Gly
        355                 360                 365

Asp Met Cys Asn Phe Gly Ser Leu Asn Tyr Ser Leu Val Asp Pro Val
    370                 375                 380

Lys Ser Ile Gln Asn Lys Asn Leu Trp Gln Gln Asn Asp Asn Gly Gly
385                 390                 395                 400

Asp Glu Asp Asp Met Cys Leu Ile Asp Glu Asn Phe Leu Thr Phe
                405                 410                 415

Asp Gly Glu Met Ser Ser Thr Leu Glu Lys Asp Cys His Leu Lys Lys
                420                 425                 430

Ser Cys Asp Asp Ile Ser Asp Met Ser Ile Ala Leu Lys Ser Lys Phe
            435                 440                 445

Asp Glu Ser Pro Gly Asn Gly Glu Lys Glu Ser Thr Met Ser Met Glu
        450                 455                 460

Cys Asp Gln Pro Ser Tyr Ser Glu Asp Asp Glu Leu Thr Glu Ser
465                 470                 475                 480

Lys Ile Lys Ala Phe Leu Asp Glu Lys Ala Ala Asp Leu Lys Lys Leu
                485                 490                 495
```

```
Gln Thr Pro Leu Tyr Glu Glu Phe Tyr Asn Ser Leu Ile Thr Phe Ser
            500                 505                 510

Pro Ser Cys Met Glu Ser Asn Leu Ser Asn Ser Lys Arg Glu Asp Thr
        515                 520                 525

Ala Arg Gly Phe Leu Lys Leu Pro Pro Lys Ser Arg Ser Pro Ser Arg
    530                 535                 540

Gly Pro Leu Gly Gly Ser Pro Ser Arg Ala Thr Asp Ala Thr Ser Cys
545                 550                 555                 560

Ser Lys Ser Pro Gly Ser Gly Ser Arg Glu Leu Asn Ile Asn Asn
                565                 570                 575

Gly Gly Asp Glu Ala Ser Gln Asp Gly Val Ser Ala Arg Val Thr Asp
            580                 585                 590

Trp Arg Gly Leu Val Val Asp Thr Lys Gln Glu Leu Ser Gln Cys Val
            595                 600                 605

Ala Leu Ser Glu Ile Glu Lys Lys Trp Lys Glu Leu Asp Gln Glu
        610                 615                 620

Leu Glu Arg Lys Arg Gln Glu Ile Met Arg Gln Ala Gly Leu Gly Ser
625                 630                 635                 640

Ser Pro Arg Asp Arg Gly Met Ser Arg Gln Arg Glu Lys Ser Arg Phe
                645                 650                 655

Ala Ser Pro Gly Lys
            660

<210> SEQ ID NO 8
<211> LENGTH: 2155
<212> TYPE: DNA
<213> ORGANISM: Arabidopsis thaliana

<400> SEQUENCE: 8
cggctccgtt cgtcgatcgc ttgttttccg tccttcttcc gacgacgata accaggagaa      60
ccagcctccg tttccggtg ttctcgccga taagatcacc tcttgcatcc gcaaatcgaa      120
gatttttatc aaaccctcct ctcgcctcc tcctcctgct aacactgtag acatggcacc      180
tccgatttcg tggaggaaag gtcagttaat tggtcgcggc gcgtttggta cggtgtacat      240
gggtatgaat cttgactccg gggagcttct cgccgtcaaa caggttctga ttgcagccaa      300
ttttgcttcc aaggaaaaga ctcaggctca tattcaggag cttgaagaag aagttaagct      360
tcttaaaaat ctctcccatc ctaatatagt tagatatttg ggtacagtga gggaagatga      420
taccctgaat atccttctcg agtttgttcc cggtggatcg atatcatcgc tcttggagaa      480
atttggacct tttcctgaat cagttgtccg gacatacaca aggcaactgc ttttagggtt      540
ggagtacctg cacaatcatg caattatgca cagagacatt aagggggcta atatccttgt      600
ggataataaa ggatgcatta agcttgctga ttttggtgca tccaaacaag tagctgagtt      660
ggctacgatg actggtgcaa atctatgaa agggacacca tattggatgg ctccggaagt      720
tatccttcaa actggacata gcttctctgc tgacatatgg agcgtcggct gtacagttat      780
tgaaatggtg actgggaagg ctccttggag tcagcagtat aaagaggttg ctgctatctt      840
cttcatagga acaacaaaat cacatcctcc aatacctgat actctctcct ctgatgcaaa      900
agattttctg ctcaagtgtc tgcaggaggt accaaatctg cggccaaccg catctgagct      960
actaaagcat ccttttgtta tggggaaaca caaggagtct gcttctactg atcttggttc     1020
tgtcctgaac aatcttagca ctccactacc gttacagata aataacacca agagcactcc     1080
agattctact tgcgacgatg taggtgacat gtgtaacttt ggcagtttga attattcact     1140
```

-continued

```
tgtagatcct gtgaaatcaa tccaaaacaa aaatttatgg caacaaaatg ataatggagg    1200
tgatgaagac gatatgtgtt tgatagatga tgagaatttc ttgacatttg acggagaaat    1260
gagttctacc cttgaaaaag attgtcatct gaagaagagc tgtgatgaca taagtgatat    1320
gtccattgct ttgaagtcca aatttgacga aagtcctggt aatggagaga aagagtctac    1380
aatgagcatg gaatgtgacc aaccttcata ctcagaggat gatgatgagc tgaccgagtc    1440
aaaaattaaa gctttcttag atgagaaggc tgcagatcta aagaagttac agactcctct    1500
ctatgaagaa ttctacaata gtttgatcac attctctccc agttgtatgg agagtaattt    1560
aagtaacagt aaaagagagg acactgctcg tggtttcctg aaactgcctc caaaaagcag    1620
gtcaccgagt cggggccctc ttggtggttc accttcaaga gcaacagacg caactagttg    1680
ttccaagagc ccaggaagtg gaggtagtcg tgaattgaat attaacaatg gaggtgatga    1740
agcttcacag gatggtgtat cagcacgggt cacagactgg aggggcctcg ttgttgacac    1800
taagcaggaa ttaagccagt gtgttgcttt gtcagagata gagaagaagt ggaaggaaga    1860
gcttgatcaa gaactggaaa gaaagcgaca agaaatcatg cgccaagcag ggttgggatc    1920
atccccaaga gacagaggca tgagccgaca gagagagaag tcgaggtttg catcaccagg    1980
aaaatgactt gcacaaaaag tctccggctt tttgattttt gattgctcaa ctagtatata    2040
tatctgtaac tcttatctcg ctgtgatgaa aagtagacac gaggtttggt ctgaatatat    2100
gattctgaac tggttgttga aggtattaga tgtgtgtaat gtgagtgtcg ggtgc         2155
```

<210> SEQ ID NO 9
<211> LENGTH: 268
<212> TYPE: PRT
<213> ORGANISM: Arabidopsis thaliana

<400> SEQUENCE: 9

```
Pro Pro Ile Ser Trp Arg Lys Gly Gln Leu Ile Gly Arg Gly Ala Phe
  1               5                  10                  15

Gly Thr Val Tyr Met Gly Met Asn Leu Asp Ser Gly Glu Leu Leu Ala
                 20                  25                  30

Val Lys Gln Val Leu Ile Ala Ala Asn Phe Ala Ser Lys Glu Lys Thr
             35                  40                  45

Gln Ala His Ile Gln Glu Leu Glu Glu Val Lys Leu Leu Lys Asn
         50                  55                  60

Leu Ser His Pro Asn Ile Val Arg Tyr Leu Gly Thr Val Arg Glu Asp
 65                  70                  75                  80

Asp Thr Leu Asn Ile Leu Leu Glu Phe Val Pro Gly Gly Ser Ile Ser
                 85                  90                  95

Ser Leu Leu Glu Lys Phe Gly Pro Phe Pro Glu Ser Val Val Arg Thr
            100                 105                 110

Tyr Thr Arg Gln Leu Leu Leu Gly Leu Glu Tyr Leu His Asn His Ala
            115                 120                 125

Ile Met His Arg Asp Ile Lys Gly Ala Asn Ile Leu Val Asp Asn Lys
        130                 135                 140

Gly Cys Ile Lys Leu Ala Asp Phe Gly Ala Ser Lys Gln Val Ala Glu
145                 150                 155                 160

Leu Ala Thr Met Thr Gly Ala Lys Ser Met Lys Gly Thr Pro Tyr Trp
                165                 170                 175

Met Ala Pro Glu Val Ile Leu Gln Thr Gly His Ser Phe Ser Ala Asp
            180                 185                 190

Ile Trp Ser Val Gly Cys Thr Val Ile Glu Met Val Thr Gly Lys Ala
```

-continued

```
                    195                 200                 205
            Pro Trp Ser Gln Gln Tyr Lys Glu Val Ala Ala Ile Phe Phe Ile Gly
                210                 215                 220
            Thr Thr Lys Ser His Pro Pro Ile Pro Asp Thr Leu Ser Ser Asp Ala
            225                 230                 235                 240
            Lys Asp Phe Leu Leu Lys Cys Leu Gln Glu Val Pro Asn Leu Arg Pro
                            245                 250                 255
            Thr Ala Ser Glu Leu Leu Lys His Pro Phe Val Met
                        260                 265
```

<210> SEQ ID NO 10
<211> LENGTH: 802
<212> TYPE: DNA
<213> ORGANISM: Arabidopsis thaliana

<400> SEQUENCE: 10

```
tccgatttcg tggaggaaag gtcagttaat tggtcgcggc gcgtttggta cggtgtacat      60
gggtatgaat cttgactccg gggagcttct cgccgtcaaa caggttctga ttgcagccaa     120
ttttgcttcc aaggaaaaga ctcaggctca tattcaggag cttgaagaag aagttaagct     180
tcttaaaaat ctctcccatc ctaatatagt tagatatttg ggtacagtga gggaagatga     240
taccctgaat atccttctcg agtttgttcc cggtggatcg atatcatcgc tcttggagaa     300
atttggacct tttcctgaat cagttgtccg gacatacaca aggcaactgc ttttagggtt     360
ggagtacctg cacaatcatg caattatgca cagagacatt aagggggcta atatccttgt     420
ggataataaa ggatgcatta agcttgctga ttttggtgca tccaaacaag tagctgagtt     480
ggctacgatg actggtgcaa aatctatgaa agggacacca tattggatgg ctccggaagt     540
tatccttcaa actggacata gcttctctgc tgacatatgg agcgtcggct gtacagttat     600
tgaaatggtg actgggaagg ctccttggag tcagcagtat aaagaggttg ctgctatctt     660
cttcatagga acaacaaaat cacatcctcc aatacctgat actctctcct ctgatgcaaa     720
agattttctg ctcaagtgtc tgcaggaggt accaaatctg cggccaaccg catctgagct     780
actaaagcat ccttttgtta tg                                              802
```

<210> SEQ ID NO 11
<211> LENGTH: 642
<212> TYPE: PRT
<213> ORGANISM: Arabidopsis thaliana

<400> SEQUENCE: 11

```
Arg Ser Leu Val Phe Arg Ser Thr Thr Asp Asp Glu Asn Gln Glu Asn
  1               5                  10                  15
His Pro Pro Pro Phe Pro Ser Leu Leu Ala Asp Lys Ile Thr Ser Cys
                 20                  25                  30
Ile Arg Lys Ser Met Val Phe Ala Lys Ser Gln Ser Pro Asn Asn
             35                  40                  45
Ser Thr Val Gln Ile Lys Pro Pro Ile Arg Trp Arg Lys Gly Gln Leu
         50                  55                  60
Ile Gly Arg Gly Ala Phe Gly Thr Val Tyr Met Gly Met Asn Leu Asp
 65                  70                  75                  80
Ser Gly Glu Leu Leu Ala Val Lys Gln Ala Leu Ile Thr Ser Asn Cys
                 85                  90                  95
Ala Ser Lys Glu Lys Thr Gln Ala His Ile Gln Glu Leu Glu Glu Glu
            100                 105                 110
```

```
Val Lys Leu Leu Lys Asn Leu Ser His Pro Asn Ile Val Arg Tyr Leu
        115                 120                 125

Gly Thr Val Arg Glu Asp Glu Thr Leu Asn Ile Leu Leu Glu Phe Val
130                 135                 140

Pro Gly Gly Ser Ile Ser Ser Leu Leu Glu Lys Phe Gly Ala Phe Pro
145                 150                 155                 160

Glu Ser Val Val Arg Thr Tyr Thr Asn Gln Leu Leu Leu Gly Leu Glu
                165                 170                 175

Tyr Leu His Asn His Ala Ile Met His Arg Asp Ile Lys Gly Ala Asn
            180                 185                 190

Ile Leu Val Asp Asn Gln Gly Cys Ile Lys Leu Ala Asp Phe Gly Ala
        195                 200                 205

Ser Lys Gln Val Ala Glu Leu Ala Thr Ile Ser Gly Ala Lys Ser Met
    210                 215                 220

Lys Gly Thr Pro Tyr Trp Met Ala Pro Glu Val Ile Leu Gln Thr Gly
225                 230                 235                 240

His Ser Phe Ser Ala Asp Ile Trp Ser Val Gly Cys Thr Val Ile Glu
                245                 250                 255

Met Val Thr Gly Lys Ala Pro Trp Ser Gln Gln Tyr Lys Glu Ile Ala
            260                 265                 270

Ala Ile Phe His Ile Gly Thr Thr Lys Ser His Pro Pro Ile Pro Asp
        275                 280                 285

Asn Ile Ser Ser Asp Ala Asn Asp Phe Leu Leu Lys Cys Leu Gln Gln
290                 295                 300

Glu Pro Asn Leu Arg Pro Thr Ala Ser Glu Leu Leu Lys His Pro Phe
305                 310                 315                 320

Val Thr Gly Lys Gln Lys Glu Ser Ala Ser Lys Asp Leu Thr Ser Phe
                325                 330                 335

Met Asp Asn Ser Cys Ser Pro Leu Pro Ser Glu Leu Thr Asn Ile Thr
            340                 345                 350

Ser Tyr Gln Thr Ser Thr Ser Asp Asp Val Gly Asp Ile Cys Asn Leu
        355                 360                 365

Gly Ser Leu Thr Cys Thr Leu Ala Phe Pro Glu Lys Ser Ile Gln Asn
    370                 375                 380

Asn Ser Leu Cys Leu Lys Ser Asn Asn Gly Tyr Asp Asp Asp Asp Asp
385                 390                 395                 400

Asn Asp Met Cys Leu Ile Asp Asp Glu Asn Phe Leu Thr Tyr Asn Gly
                405                 410                 415

Glu Thr Gly Pro Ser Leu Asp Asn Asn Thr Asp Ala Lys Lys Ser Cys
            420                 425                 430

Asp Thr Met Ser Glu Ile Ser Asp Ile Leu Lys Cys Lys Phe Asp Glu
        435                 440                 445

Asn Ser Gly Asn Gly Glu Thr Glu Thr Lys Val Ser Met Glu Val Asp
    450                 455                 460

His Pro Ser Tyr Ser Glu Asp Glu Asn Glu Leu Thr Glu Ser Lys Ile
465                 470                 475                 480

Lys Ala Phe Leu Asp Asp Lys Ala Ala Glu Leu Lys Lys Leu Gln Thr
                485                 490                 495

Pro Leu Tyr Glu Glu Phe Tyr Asn Gly Met Ile Thr Cys Ser Pro Ile
            500                 505                 510

Cys Met Glu Ser Asn Ile Asn Asn Asn Lys Arg Glu Glu Ala Pro Arg
        515                 520                 525

Gly Phe Leu Lys Leu Pro Pro Lys Ser Arg Ser Pro Ser Gln Gly His
```

|  | | | | | | 530 | | | | | 535 | | | | | 540 | | |
|---|---|---|---|---|---|---|---|---|---|---|---|---|---|---|---|---|---|---|

Ile Gly Arg Ser Pro Ser Arg Ala Thr Asp Ala Ala Cys Cys Ser Lys
545                 550                 555                 560

Ser Pro Glu Ser Gly Asn Ser Gly Ala Pro Lys Asn Ser Asn Ala
            565                 570                 575

Ser Ala Gly Ala Glu Gln Glu Ser Asn Ser Gln Ser Val Ala Leu Ser
            580                 585                 590

Glu Ile Glu Arg Lys Trp Lys Glu Glu Leu Asp Gln Glu Leu Glu Arg
            595                 600                 605

Lys Arg Arg Glu Ile Thr Arg Gln Ala Gly Met Gly Ser Ser Pro Arg
    610                 615                 620

Asp Arg Ser Leu Ser Arg His Arg Glu Lys Ser Arg Phe Ala Ser Pro
625                 630                 635                 640

Gly Lys

<210> SEQ ID NO 12
<211> LENGTH: 2193
<212> TYPE: DNA
<213> ORGANISM: Arabidopsis thaliana

<400> SEQUENCE: 12

```
cgctcacttg tcttccgttc taccaccgac gatgagaatc aagagaatca tcctcctccg    60
tttccttctc tcctcgccga taaaatcact tcctgtatcc gcaaatcaat ggttttcgcc   120
aaatcccagt cacctccgaa taactccacc gtacaaatca aacctccgat tcggtggcgg   180
aaaggtcagt taattggccg tggcgctttt ggtactgtgt atatgggtat gaatctcgat   240
tccggtgagc ttctcgccgt taaacaggct ctgattacat ctaattgtgc atccaaggaa   300
aaaactcagg ctcatattca ggagcttgaa gaggaagtga agctactcaa gaatctctct   360
catccaaata tagttagata tttgggtacg gtgagggaag atgaaacttt gaatatcttg   420
cttgaatttg ttcctggtgg atctatatct tcactcttgg agaaatttgg agcctttcct   480
gaatctgttt tcggacata cacgaaccaa ctgcttttgg gattgagta ccttcataat   540
catgccatta tgcaccgtga cattaagggt gctaatatcc ttgtggataa tcaaggatgc   600
attaaacttc tgattttggg tcgtccaaa caggtagcgg agttggctac tatttcgggt   660
gccaaatcta tgaaaggaac tccctattgg atggctccag aagttattct tcaaaccggg   720
catagctttt ctgctgatat ttggagtgta ggatgcacag tgattgaaat ggtgactgga   780
aaagctcctt ggagccagca atataaagag attgctgcta ttttccacat tggaacgacg   840
aaatcgcatc ctccaatccc tgacaatatc tcctctgacg caaatgattt tttgctcaag   900
tgtctgcagc aggaaccaaa tctgcggcca accgcttctg agctgctaaa gcatccattt   960
gttacgggca aacagaagga atctgcgtct aaagatctta cttcatttat ggacaattca  1020
tgcagtcctt taccatcaga gttgactaac attacgagct atcaaacatc tacgagtgac  1080
gatgtaggag acatctgtaa cttgggtagt ctgacttgta cacttgcttt ccctgagaaa  1140
tcaatccaaa ataacagttt gtgtctgaaa agtaataacg ggtatgatga cgatgatgat  1200
aatgatatgt gtttgattga cgatgagaat tccttgacat ataatggaga gactggccct  1260
agtcttgaca ataatactga tgccaagaag agctgtgata ccatgagtga gatctctgat  1320
attttgaagt gcaaatttga cgaaaattct ggaaacggag aaacagagac gaaagttagt  1380
atggaagttg accatccatc atactcggag gatgaaaatg agctgactga gtcgaaaatc  1440
aaagctttct tagatgacaa ggctgcagag ttaaagaagt tacagacgcc tctgtacgaa  1500
```

-continued

```
gaattctaca acggtatgat cacatgctcc cccatctgca tggagagtaa catcaataac    1560
aataaacgag aggaggcacc tcgtggtttc ttgaaactgc ctccaaaaag tcggtctccg    1620
agtcagggcc atattggtcg atcaccttct agagcaacag atgcagcctg ttgttccaag    1680
agtccagaaa gtggtaatag ctctggtgcc ccgaagaata gcaatgcaag tgctggtgct    1740
gaacaagaat caaacagtca aagtgtcgcg ctgtcggaga tagagaggaa gtggaaggaa    1800
gagcttgatc aagaacttga agaaagcga agagagatta cacggcaagc agggatggga    1860
tcatccccga gagatagaag cttgagccga catagagaga agtcaagatt tgcatctcca    1920
ggcaaatgat ctgtacaaaa gaaaagcagc caattttgca cttttgtctg taaggcttgt    1980
attgcttttg atctttcgat ttgctcatct agtatatatg atatagacat aaaattgtgc    2040
caacttaaag tttgaatata tatagatagc taaactattt gcttaagtag ggtgtgatgt    2100
gagaatgttg gtgcatattg agtgttaagc caaccacaga acaaatattt tcgagaaatt    2160
atcgaaagct ttgtttactt tcggtccggt ccg                                  2193
```

<210> SEQ ID NO 13
<211> LENGTH: 268
<212> TYPE: PRT
<213> ORGANISM: Arabidopsis thaliana

<400> SEQUENCE: 13

| Pro | Pro | Ile | Arg | Trp | Arg | Lys | Gly | Gln | Leu | Ile | Gly | Arg | Gly | Ala | Phe |
|---|---|---|---|---|---|---|---|---|---|---|---|---|---|---|---|
| 1 | | | | 5 | | | | | 10 | | | | | 15 | |

| Gly | Thr | Val | Tyr | Met | Gly | Met | Asn | Leu | Asp | Ser | Gly | Glu | Leu | Leu | Ala |
| | | | 20 | | | | | 25 | | | | | 30 | | |

| Val | Lys | Gln | Ala | Leu | Ile | Thr | Ser | Asn | Cys | Ala | Ser | Lys | Glu | Lys | Thr |
| | | 35 | | | | | 40 | | | | | 45 | | | |

| Gln | Ala | His | Ile | Gln | Glu | Leu | Glu | Glu | Glu | Val | Lys | Leu | Leu | Lys | Asn |
| | 50 | | | | | 55 | | | | | 60 | | | | |

| Leu | Ser | His | Pro | Asn | Ile | Val | Arg | Tyr | Leu | Gly | Thr | Val | Arg | Glu | Asp |
| 65 | | | | | 70 | | | | | 75 | | | | | 80 |

| Glu | Thr | Leu | Asn | Ile | Leu | Leu | Glu | Phe | Val | Pro | Gly | Gly | Ser | Ile | Ser |
| | | | | 85 | | | | | 90 | | | | | 95 | |

| Ser | Leu | Leu | Glu | Lys | Phe | Gly | Ala | Phe | Pro | Glu | Ser | Val | Val | Arg | Thr |
| | | | 100 | | | | | 105 | | | | | 110 | | |

| Tyr | Thr | Asn | Gln | Leu | Leu | Leu | Gly | Leu | Glu | Tyr | Leu | His | Asn | His | Ala |
| | | | 115 | | | | | 120 | | | | | 125 | | |

| Ile | Met | His | Arg | Asp | Ile | Lys | Gly | Ala | Asn | Ile | Leu | Val | Asp | Asn | Gln |
| | 130 | | | | | 135 | | | | | 140 | | | | |

| Gly | Cys | Ile | Lys | Leu | Ala | Asp | Phe | Gly | Ala | Ser | Lys | Gln | Val | Ala | Glu |
| 145 | | | | | 150 | | | | | 155 | | | | | 160 |

| Leu | Ala | Thr | Ile | Ser | Gly | Ala | Lys | Ser | Met | Lys | Gly | Thr | Pro | Tyr | Trp |
| | | | | 165 | | | | | 170 | | | | | 175 | |

| Met | Ala | Pro | Glu | Val | Ile | Leu | Gln | Thr | Gly | His | Ser | Phe | Ser | Ala | Asp |
| | | | 180 | | | | | 185 | | | | | 190 | | |

| Ile | Trp | Ser | Val | Gly | Cys | Thr | Val | Ile | Glu | Met | Val | Thr | Gly | Lys | Ala |
| | | | 195 | | | | | 200 | | | | | 205 | | |

| Pro | Trp | Ser | Gln | Gln | Tyr | Lys | Glu | Ile | Ala | Ala | Ile | Phe | His | Ile | Gly |
| | | 210 | | | | | 215 | | | | | 220 | | | |

| Thr | Thr | Lys | Ser | His | Pro | Pro | Ile | Pro | Asp | Asn | Ile | Ser | Ser | Asp | Ala |
| 225 | | | | | 230 | | | | | 235 | | | | | 240 |

| Asn | Asp | Phe | Leu | Leu | Lys | Cys | Leu | Gln | Gln | Glu | Pro | Asn | Leu | Arg | Pro |

245                 250                 255
Thr Ala Ser Glu Leu Leu Lys His Pro Phe Val Thr
            260                 265

<210> SEQ ID NO 14
<211> LENGTH: 804
<212> TYPE: DNA
<213> ORGANISM: Arabidopsis thaliana

<400> SEQUENCE: 14
cctccgattc ggtggcggaa aggtcagtta attggccgtg gcgcttttgg tactgtgtat      60
atgggtatga atctcgattc cggtgagctt ctcgccgtta acaggctct gattacatct     120
aattgtgcat ccaaggaaaa aactcaggct catattcagg agcttgaaga ggaagtgaag     180
ctactcaaga atctctctca tccaaatata gttagatatt tgggtacggt gagggaagat     240
gaaactttga atatcttgct tgaatttgtt cctggtggat ctatatcttc actcttggag     300
aaatttggag cctttcctga atctgttgtt cggacataca cgaaccaact gcttttggga     360
ttggagtacc ttcataatca tgccattatg caccgtgaca ttaagggtgc taatatcctt     420
gtggataatc aaggatgcat taaacttgct gattttggtg cgtccaaaca ggtagcggag     480
ttggctacta tttcgggtgc caaatctatg aaaggaactc cctattggat ggctccagaa     540
gttattcttc aaaccgggca tagctttct gctgatattt ggagtgtagg atgcacagtg     600
attgaaatgg tgactggaaa agctccttgg agccagcaat ataaagagat tgctgctatt     660
ttccacattg gaacgacgaa atcgcatcct ccaatccctg acaatatctc ctctgacgca     720
aatgatttt tgctcaagtg tctgcagcag gaaccaaatc tgcggccaac cgcttctgag     780
ctgctaaagc atccatttgt tacg                                            804

<210> SEQ ID NO 15
<211> LENGTH: 651
<212> TYPE: PRT
<213> ORGANISM: Arabidopsis thaliana

<400> SEQUENCE: 15

Met Gln Asp Ile Leu Gly Ser Val Arg Arg Ser Leu Val Phe Arg Ser
 1               5                  10                  15

Ser Leu Ala Gly Asp Asp Gly Thr Ser Gly Gly Gly Leu Ser Gly Phe
            20                  25                  30

Val Gly Lys Ile Asn Ser Ser Ile Arg Ser Ser Arg Ile Gly Leu Phe
        35                  40                  45

Ser Lys Pro Pro Pro Gly Leu Pro Ala Pro Arg Lys Glu Glu Ala Pro
    50                  55                  60

Ser Ile Arg Trp Arg Lys Gly Glu Leu Ile Gly Cys Gly Ala Phe Gly
65                  70                  75                  80

Arg Val Tyr Met Gly Met Asn Leu Asp Ser Gly Glu Leu Leu Ala Ile
                85                  90                  95

Lys Gln Val Leu Ile Ala Pro Ser Ser Ala Ser Lys Glu Lys Thr Gln
            100                 105                 110

Gly His Ile Arg Glu Leu Glu Glu Val Gln Leu Leu Lys Asn Leu
        115                 120                 125

Ser His Pro Asn Ile Val Arg Tyr Leu Gly Thr Val Arg Glu Ser Asp
    130                 135                 140

Ser Leu Asn Ile Leu Met Glu Phe Val Pro Gly Gly Ser Ile Ser Ser
145                 150                 155                 160

```
Leu Leu Glu Lys Phe Gly Ser Phe Pro Glu Pro Val Ile Ile Met Tyr
                165                 170                 175

Thr Lys Gln Leu Leu Gly Leu Glu Tyr Leu His Asn Asn Gly Ile
            180                 185                 190

Met His Arg Asp Ile Lys Gly Ala Asn Ile Leu Val Asp Asn Lys Gly
        195                 200                 205

Cys Ile Arg Leu Ala Asp Phe Gly Ala Ser Lys Val Val Glu Leu
210                 215                 220

Ala Thr Val Asn Gly Ala Lys Ser Met Lys Gly Thr Pro Tyr Trp Met
225                 230                 235                 240

Ala Pro Glu Val Ile Leu Gln Thr Gly His Ser Phe Ser Ala Asp Ile
                245                 250                 255

Trp Ser Val Gly Cys Thr Val Ile Glu Met Ala Thr Gly Lys Pro Pro
            260                 265                 270

Trp Ser Glu Gln Tyr Gln Gln Phe Ala Ala Val Leu His Ile Gly Arg
            275                 280                 285

Thr Lys Ala His Pro Pro Ile Pro Glu Asp Leu Ser Pro Glu Ala Lys
        290                 295                 300

Asp Phe Leu Met Lys Cys Leu His Lys Glu Pro Ser Leu Arg Leu Ser
305                 310                 315                 320

Ala Thr Glu Leu Leu Gln His Pro Phe Val Thr Gly Lys Arg Gln Glu
                325                 330                 335

Pro Tyr Pro Ala Tyr Arg Asn Ser Leu Thr Glu Cys Gly Asn Pro Ile
            340                 345                 350

Thr Thr Gln Gly Met Asn Val Arg Ser Ser Ile Asn Ser Leu Ile Arg
            355                 360                 365

Arg Ser Thr Cys Ser Gly Leu Lys Asp Val Cys Glu Leu Gly Ser Leu
        370                 375                 380

Arg Ser Ser Ile Ile Tyr Pro Gln Lys Ser Asn Asn Ser Gly Phe Gly
385                 390                 395                 400

Trp Arg Asp Gly Asp Ser Asp Asp Leu Cys Gln Thr Asp Met Asp Asp
                405                 410                 415

Leu Cys Asn Ile Glu Ser Val Arg Asn Asn Val Leu Ser Gln Ser Thr
            420                 425                 430

Asp Leu Asn Lys Ser Phe Asn Pro Met Cys Asp Ser Thr Asp Asn Trp
        435                 440                 445

Ser Cys Lys Phe Asp Glu Ser Pro Lys Val Met Lys Ser Lys Ser Asn
450                 455                 460

Leu Leu Ser Tyr Gln Ala Ser Gln Leu Gln Thr Gly Val Pro Cys Asp
465                 470                 475                 480

Glu Glu Thr Ser Leu Thr Phe Ala Gly Gly Ser Ser Val Ala Glu Asp
                485                 490                 495

Asp Tyr Lys Gly Thr Glu Leu Lys Ile Lys Ser Phe Leu Asp Glu Lys
            500                 505                 510

Ala Gln Asp Leu Lys Arg Leu Gln Thr Pro Leu Leu Glu Glu Phe His
        515                 520                 525

Asn Ala Met Asn Pro Gly Ile Pro Gln Gly Ala Leu Gly Asp Thr Asn
        530                 535                 540

Ile Tyr Asn Leu Pro Asn Leu Pro Ser Ile Ser Lys Thr Pro Lys Arg
545                 550                 555                 560

Leu Pro Ser Arg Arg Leu Ser Ala Ile Ser Asp Ala Met Pro Ser Pro
                565                 570                 575

Leu Lys Ser Ser Lys Arg Thr Leu Asn Thr Ser Arg Val Met Gln Ser
```

-continued

```
                580                 585                 590
Gly Thr Glu Pro Thr Gln Val Asn Glu Ser Thr Lys Lys Gly Val Asn
                595                 600                 605

Asn Ser Arg Cys Phe Ser Glu Ile Arg Arg Lys Trp Glu Glu Leu
        610                 615                 620

Tyr Glu Glu Leu Glu Arg His Arg Glu Asn Leu Arg His Ala Gly Ala
625                 630                 635                 640

Gly Gly Lys Thr Pro Leu Ser Gly His Lys Gly
                645                 650
```

<210> SEQ ID NO 16
<211> LENGTH: 2157
<212> TYPE: DNA
<213> ORGANISM: Arabidopsis thaliana

<400> SEQUENCE: 16

| | | | | | |
|---|---|---|---|---|---|
| tcttcactga | tctctctaca | cattcaccgt | cggcttctca | aatgcaggat | attctcggat | 60 |
| cggttcgccg | atccttggtt | ttccggtcgt | ctttggccgg | agacgatggt | actagcggcg | 120 |
| gaggtcttag | cggattcgtc | gggaagatta | actctagtat | ccgtagctct | cgaattgggc | 180 |
| tcttttctaa | gccgcctcca | gggcttcctg | ctcctagaaa | agaagaagcg | ccgtcgattc | 240 |
| ggtggaggaa | aggggaatta | atcggttgcg | gtgcttttgg | aagagtttac | atgggaatga | 300 |
| acctcgattc | cggcgagctt | cttgcaatta | aacaggtttt | aatcgctcca | agcagtgctt | 360 |
| caaaggagaa | gactcagggt | cacatccgag | agcttgagga | agaagtacaa | cttcttaaga | 420 |
| atctttcaca | tccgaacatc | gttagatact | tgggtactgt | aagagagagt | gattcgttga | 480 |
| atattttgat | ggagtttgtt | cctggtggat | caatatcatc | tttgttggag | aagtttggat | 540 |
| cttttcctga | gcctgtgatt | attatgtaca | caaagcaact | tctgcttggg | ctggaatatc | 600 |
| ttcacaacaa | tgggatcatg | catcgagata | ttaaggggc | aaatattttg | gtcgataaca | 660 |
| aaggttgcat | cagactcgca | gattttggtg | cttccaagaa | agttgtagag | ctagctactg | 720 |
| taaatggtgc | caaatctatg | aaggggacgc | ttattggat | ggctcctgaa | gtcattctcc | 780 |
| agactggtca | tagcttctct | gctgatatat | ggagtgttgg | gtgcactgtg | attgagatgg | 840 |
| ctacggggaa | gcctccctgg | agcgagcagt | atcagcagtt | tgctgctgtc | cttcatattg | 900 |
| gtagaacaaa | agctcatcct | ccaattccag | aagacctctc | accagaggct | aaagactttc | 960 |
| taatgaaatg | cttacacaaa | gaaccaagct | tgagactctc | tgcaaccgaa | ttgcttcagc | 1020 |
| acccgtttgt | cactggaaag | cgccaggaac | cttatccagc | ttaccgtaat | tctcttacgg | 1080 |
| aatgtggaaa | cccaataact | actcaaggaa | tgaatgttcg | gagttcaata | aattcgttga | 1140 |
| tcaggaggtc | gacatgttca | ggcttgaagg | atgtctgtga | actgggaagc | ttgaggagtt | 1200 |
| ccattatata | cccacagaag | tcaaataact | caggatttgg | ttggcgagat | ggagactctg | 1260 |
| atgacctttg | tcagaccgat | atggatgatc | tctgcaacat | tgaatcagtc | agaaacaatg | 1320 |
| ttttgtcaca | gtccaccgat | ttaaacaaga | gttttaatcc | catgtgtgat | tccacggata | 1380 |
| actggtcttg | caagtttgat | gaaagcccaa | aagtgatgaa | aagcaaatct | aacctgcttt | 1440 |
| cttaccaagc | ttctcaactc | caaactggag | ttccatgtga | tgaggaaacc | agcttaacat | 1500 |
| tgctggtgg | ctcttccgtt | gcagaggatg | attataaagg | cacagagttg | aaaataaaat | 1560 |
| cattttggga | tgagaaggct | caggatttga | aaaggttgca | gaccccctctg | cttgaagaat | 1620 |
| tccacaatgc | tatgaatcca | ggaatacccc | aagtgcact | tggagacacc | aatatctaca | 1680 |
| atttaccaaa | cttaccaagt | ataagcaaga | cacctaaacg | acttccgagt | agacgactct | 1740 |

-continued

```
cagcaatcag tgatgctatg cccagcccac tcaaaagctc caaacgtaca ctgaacacaa    1800
gcagagtgat gcagtcagga actgaaccaa ctcaagtcaa cgagtcgacc aagaagggag    1860
taaataatag ccgttgtttc tcagagatac gtcggaagtg ggaagaagaa ctctatgaag    1920
agcttgagag gcatcgagag aatctgcgac acgctggtgc aggagggaag actccattat    1980
caggccacaa aggatagtga acggctaaag agaaactgta tgtttctttc ttatgtttca    2040
aaattacttc ttcgtatttt tttttgttgg tggggtaatt tcatgagcta gtatgatata    2100
tgtagatagt tcttcaacgg ttacatagta ttattattta ttattaattt aattgcc       2157
```

<210> SEQ ID NO 17
<211> LENGTH: 268
<212> TYPE: PRT
<213> ORGANISM: Arabidopsis thaliana

<400> SEQUENCE: 17

```
Pro Ser Ile Arg Trp Arg Lys Gly Glu Leu Ile Gly Cys Gly Ala Phe
 1               5                  10                  15

Gly Arg Val Tyr Met Gly Met Asn Leu Asp Ser Gly Glu Leu Leu Ala
            20                  25                  30

Ile Lys Gln Val Leu Ile Ala Pro Ser Ser Ala Ser Lys Glu Lys Thr
        35                  40                  45

Gln Gly His Ile Arg Glu Leu Glu Glu Glu Val Gln Leu Leu Lys Asn
    50                  55                  60

Leu Ser His Pro Asn Ile Val Arg Tyr Leu Gly Thr Val Arg Glu Ser
65                  70                  75                  80

Asp Ser Leu Asn Ile Leu Met Glu Phe Val Pro Gly Gly Ser Ile Ser
                85                  90                  95

Ser Leu Leu Glu Lys Phe Gly Ser Phe Pro Glu Pro Val Ile Ile Met
            100                 105                 110

Tyr Thr Lys Gln Leu Leu Leu Gly Leu Glu Tyr Leu His Asn Asn Gly
        115                 120                 125

Ile Met His Arg Asp Ile Lys Gly Ala Asn Ile Leu Val Asp Asn Lys
    130                 135                 140

Gly Cys Ile Arg Leu Ala Asp Phe Gly Ala Ser Lys Lys Val Val Glu
145                 150                 155                 160

Leu Ala Thr Val Asn Gly Ala Lys Ser Met Lys Gly Thr Pro Tyr Trp
                165                 170                 175

Met Ala Pro Glu Val Ile Leu Gln Thr Gly His Ser Phe Ser Ala Asp
            180                 185                 190

Ile Trp Ser Val Gly Cys Thr Val Ile Glu Met Ala Thr Gly Lys Pro
        195                 200                 205

Pro Trp Ser Glu Gln Tyr Gln Gln Phe Ala Ala Val Leu His Ile Gly
    210                 215                 220

Arg Thr Lys Ala His Pro Pro Ile Pro Glu Asp Leu Ser Pro Glu Ala
225                 230                 235                 240

Lys Asp Phe Leu Met Lys Cys Leu His Lys Glu Pro Ser Leu Arg Leu
                245                 250                 255

Ser Ala Thr Glu Leu Leu Gln His Pro Phe Val Thr
            260                 265
```

<210> SEQ ID NO 18
<211> LENGTH: 804
<212> TYPE: DNA
<213> ORGANISM: Arabidopsis thaliana -continued

<400> SEQUENCE: 18

```
ccgtcgattc ggtggaggaa agggaatta atcggttgcg gtgcttttgg aagagtttac      60
atgggaatga acctcgattc cggcgagctt cttgcaatta acaggtttt aatcgctcca     120
agcagtgctt caaaggagaa gactcagggt cacatccgag agcttgagga agaagtacaa    180
cttcttaaga atctttcaca tccgaacatc gttagatact tgggtactgt aagagagagt   240
gattcgttga atattttgat ggagtttgtt cctggtggat caatatcatc tttgttggag   300
aagtttggat cttttcctga gcctgtgatt attatgtaca caaagcaact tctgcttggg  360
ctggaatatc ttcacaacaa tgggatcatg catcgagata ttaagggggc aaatatttg   420
gtcgataaca aaggttgcat cagactcgca gattttggtg cttccaagaa agttgtagag  480
ctagctactg taaatggtgc caaatctatg aaggggacgc cttattggat ggctcctgaa  540
gtcattctcc agactggtca tagcttctct gctgatatat ggagtgttgg gtgcactgtg  600
attgagatgg ctacggggaa gcctccctgg agcgagcagt atcagcagtt tgctgctgtc  660
cttcatattg gtagaacaaa agctcatcct ccaattccag aagacctctc accagaggct  720
aaagactttc taatgaaatg cttacacaaa gaaccaagct tgagactctc tgcaaccgaa  780
ttgcttcagc acccgtttgt cact                                          804
```

<210> SEQ ID NO 19
<211> LENGTH: 690
<212> TYPE: PRT
<213> ORGANISM: Nicotiana tabacum

<400> SEQUENCE: 19

```
Met Gln Asp Phe Ile Gly Ser Val Arg Arg Ser Leu Val Phe Lys Gln
  1               5                  10                  15

Ser Gly Asp Phe Asp Thr Gly Ala Ala Gly Val Gly Ser Gly Phe Gly
                 20                  25                  30

Gly Phe Val Glu Lys Leu Gly Ser Ser Ile Arg Lys Ser Ser Ile Gly
         35                  40                  45

Ile Phe Ser Lys Ala His Val Pro Ala Leu Pro Ser Ile Ser Lys Ala
     50                  55                  60

Glu Leu Pro Ala Lys Ala Arg Lys Asp Asp Thr Pro Pro Ile Arg Trp
 65                  70                  75                  80

Arg Lys Gly Glu Met Ile Gly Cys Gly Ala Phe Gly Arg Val Tyr Met
                 85                  90                  95

Gly Met Asn Val Asp Ser Gly Glu Leu Leu Ala Ile Lys Glu Val Ser
                100                 105                 110

Ile Ala Met Asn Gly Ala Ser Arg Glu Arg Ala Gln Ala His Val Arg
         115                 120                 125

Glu Leu Glu Glu Glu Val Asn Leu Leu Lys Asn Leu Ser His Pro Asn
     130                 135                 140

Ile Val Arg Tyr Leu Gly Thr Ala Arg Glu Ala Gly Ser Leu Asn Ile
145                 150                 155                 160

Leu Leu Glu Phe Val Pro Gly Gly Ser Ile Ser Ser Leu Leu Gly Lys
                165                 170                 175

Phe Gly Ser Phe Pro Glu Ser Val Ile Arg Met Tyr Thr Lys Gln Leu
                180                 185                 190

Leu Leu Gly Leu Glu Tyr Leu His Lys Asn Gly Ile Met His Arg Asp
         195                 200                 205

Ile Lys Gly Ala Asn Ile Leu Val Asp Asn Lys Gly Cys Ile Lys Leu
```

-continued

```
            210                 215                 220
Ala Asp Phe Gly Ala Ser Lys Lys Val Val Glu Leu Ala Thr Met Thr
225                 230                 235                 240

Gly Ala Lys Ser Met Lys Gly Thr Pro Tyr Trp Met Ala Pro Glu Val
                245                 250                 255

Ile Leu Gln Thr Gly His Ser Phe Ser Ala Asp Ile Trp Ser Val Gly
                260                 265                 270

Cys Thr Ile Ile Glu Met Ala Thr Gly Lys Pro Pro Trp Ser Gln Gln
                275                 280                 285

Tyr Gln Glu Val Ala Ala Leu Phe His Ile Gly Thr Thr Lys Ser His
        290                 295                 300

Pro Pro Ile Pro Glu His Leu Ser Ala Glu Ser Lys Asp Phe Leu Leu
305                 310                 315                 320

Lys Cys Leu Gln Lys Glu Pro His Leu Arg His Ser Ala Ser Asn Leu
                325                 330                 335

Leu Gln His Pro Phe Val Thr Ala Glu His Gln Glu Ala Arg Pro Phe
                340                 345                 350

Leu Arg Ser Ser Phe Met Gly Asn Pro Glu Asn Met Ala Ala Gln Arg
        355                 360                 365

Met Asp Val Arg Thr Ser Ile Ile Pro Asp Met Arg Ala Ser Cys Asn
370                 375                 380

Gly Leu Lys Asp Val Cys Gly Val Ser Ala Val Arg Cys Ser Thr Val
385                 390                 395                 400

Tyr Pro Glu Asn Ser Leu Gly Lys Glu Ser Leu Trp Lys Leu Gly Asn
                405                 410                 415

Ser Asp Asp Asp Met Cys Gln Met Asp Asn Asp Asp Phe Met Phe Gly
                420                 425                 430

Ala Ser Val Lys Cys Ser Ser Asp Leu His Ser Pro Ala Asn Tyr Lys
        435                 440                 445

Ser Phe Asn Pro Met Cys Glu Pro Asp Asn Asp Trp Pro Cys Lys Phe
        450                 455                 460

Asp Glu Ser Pro Glu Leu Thr Lys Ser Gln Ala Asn Leu His Tyr Asp
465                 470                 475                 480

Gln Ala Thr Ile Lys Pro Thr Asn Asn Pro Ile Met Ser Tyr Lys Glu
                485                 490                 495

Asp Leu Ala Phe Thr Phe Pro Ser Gly Gln Ser Ala Ala Glu Asp Asp
                500                 505                 510

Asp Glu Leu Thr Glu Ser Lys Ile Arg Ala Phe Leu Asp Glu Lys Ala
        515                 520                 525

Met Asp Leu Lys Lys Leu Gln Thr Pro Leu Tyr Glu Gly Phe Tyr Asn
        530                 535                 540

Ser Leu Asn Val Ser Ser Thr Pro Ser Pro Val Gly Thr Gly Asn Lys
545                 550                 555                 560

Glu Asn Val Pro Ser Asn Ile Asn Leu Pro Pro Lys Ser Arg Ser Pro
                565                 570                 575

Lys Arg Met Leu Ser Arg Arg Leu Ser Thr Ala Ile Glu Gly Ala Cys
                580                 585                 590

Ala Pro Ser Pro Val Thr His Ser Lys Arg Ile Ser Asn Ile Gly Gly
                595                 600                 605

Leu Asn Gly Glu Ala Ile Gln Glu Ala Gln Leu Pro Arg His Asn Glu
        610                 615                 620

Trp Lys Asp Leu Leu Gly Ser Gln Arg Glu Ala Val Asn Ser Ser Phe
625                 630                 635                 640
```

Ser Glu Arg Gln Arg Arg Trp Lys Glu Glu Leu Asp Glu Glu Leu Gln
                645                 650                 655

Arg Lys Arg Glu Ile Met Arg Gln Ala Val Asn Leu Ser Pro Pro Lys
            660                 665                 670

Asp Pro Ile Leu Asn Arg Cys Arg Ser Lys Ser Arg Phe Ala Ser Pro
        675                 680                 685

Gly Arg
    690

<210> SEQ ID NO 20
<211> LENGTH: 2527
<212> TYPE: DNA
<213> ORGANISM: Nicotiana tabacum

<400> SEQUENCE: 20

| | | | | |
|---|---|---|---|---|
| ctgaacccta | acgcacacaa | cttcactctt | tgctcctcca | aatctctctc caatgcagga | 60 |
| tttcatcggc | tccgttcgcc | gatctctggt | tttcaagcag | tccggagact tcgataccgg | 120 |
| cgctgccggt | gtcggcagcg | gattcggagg | cttcgttgag | aaactaggtt cgagcattcg | 180 |
| caaatcgagt | attggaatct | tctcgaaagc | tcatgttcct | gctcttccgt ctatttctaa | 240 |
| agctgagctg | cccgcgaagg | ctcggaaaga | tgacactccg | ccaatccggt ggaggaaagg | 300 |
| tgaaatgatt | ggatgtggtg | cttttggtag | ggtttatatg | gggatgaatg ttgattctgg | 360 |
| agagttactc | gctataaagg | aggtttcgat | tgcgatgaat | ggtgcttcga gagagcgagc | 420 |
| acaagctcat | gttagagagc | ttgaggaaga | agtgaatcta | ttgaagaatc tctcccatcc | 480 |
| caacatagtg | agatatttgg | gaactgcaag | agaggcagga | tcattaaata tattgttgga | 540 |
| atttgttcct | ggtggctcaa | tctcgtcact | tttgggaaaa | tttggatcct tccctgaatc | 600 |
| tgttataaga | atgtacacca | agcaattgtt | attaggggttg | gaatacttgc ataagaatgg | 660 |
| gattatgcac | agagatatta | agggagcaaa | catacttgtt | gacaataaag gttgcattaa | 720 |
| acttgctgat | ttcggtgcat | ccaagaaggt | tgttgaattg | ctactatga ctggtgccaa | 780 |
| gtcaatgaag | ggtactccat | actggatggc | tcccgaagtc | attctgcaga ctggccatag | 840 |
| cttctctgct | gacatatgga | gtgtcggatg | cactattatc | gaaatggcta caggaaaacc | 900 |
| tccttggagc | cagcagtatc | aggaggttgc | tgctctcttc | catataggga caaccaaatc | 960 |
| ccatcccccc | atcccagagc | atctttctgc | tgaatcaaag | gacttcctat taaaatgttt | 1020 |
| gcagaaggaa | ccgcacctga | ggcattctgc | atcaaatttg | cttcagcatc catttgttac | 1080 |
| agcagaacat | caggaagctc | gcccttttct | tcgctcatcc | tttatgggaa accccgaaaa | 1140 |
| catggcggcg | caaaggatgg | atgttaggac | ctcaatcatt | cctgatatga gagcttcctg | 1200 |
| caatggtttg | aaagatgttt | gtggtgttag | cgctgtgagg | tgctccactg tatatcccga | 1260 |
| gaattcctta | gggaaagagt | cactctggaa | actaggaaac | tctgatgatg acatgtgcca | 1320 |
| gatggataat | gatgatttta | tgtttggtgc | atctgtgaaa | tgcagttcag atttgcattc | 1380 |
| tcctgctaat | tataagagtt | ttaatccttat | gtgtgaacct | gataacgatt ggccatgcaa | 1440 |
| atttgatgaa | agtcccgagt | tgacgaaaag | tcaagcaaac | ctgcattatg atcaagcaac | 1500 |
| tattaagccc | actaataacc | ccatcatgtc | atacaaggag | gatcttgctt tcacatttcc | 1560 |
| aagtgggcaa | tctgcagccg | aggatgatga | tgaattgaca | gagtctaaaa ttagggcatt | 1620 |
| ccttgatgaa | aaggcaatgg | acttgaagaa | gctgcaaaca | ccactatatg aaggattcta | 1680 |
| caattccttg | aatgtttcca | gcacaccgag | tcccgttggc | actgggaaca aggaaaatgt | 1740 |

-continued

```
tccaagtaac ataaacttac caccaaaaag caggtcacca aaacgtatgc ttagcagaag   1800
gctctctact gccattgaag gtgcttgtgc tcccagccca gtgactcatt ccaagcgaat   1860
atcaaatatt ggtggcctaa atggtgaagc tattcaggaa gctcagttgc cgaggcataa   1920
tgaatggaaa gatcttcttg gttctcaacg tgaagcagtt aattcaagct ctctctgagag  1980 gcaaagaagg tggaaagaag agcttgatga agagttgcaa aggaaacgag agattatgcg   2040
tcaggcagtc aacttatcac caccaaagga tccaattcta aatcgatgta gaagtaaatc   2100
aaggtttgca tctcctggaa gataaatgta tgtacttgtg tccctaaact aaagtcagtt   2160
tgaagaatat aattaatgat cctgcaaccc agaacagag agttagatgt cttgagcagg    2220
tatacgaacg tgaggttttc ttgacccgtt actacaggaa tcagcgcct tgtcagatag    2280 agtgagctgt tactacagga atatctgtca acctgttaat catattataa aatgccaata   2340
atttgcgttg tattcgtttt gatcattctc ctgagagcat tgtaagaaaa atgcaggcct   2400
ttttataacc tatataagtg ctctctcatg gtagttgcca atattaaaac gcagagaaaa   2460
gtcgagttct catctgctga attgtttgta aaatgtgata tattaatgta tttaccgtct   2520
tacaacc                                                             2527
```

<210> SEQ ID NO 21
<211> LENGTH: 268
<212> TYPE: PRT
<213> ORGANISM: Nicotiana tabacum

<400> SEQUENCE: 21

```
Pro Pro Ile Arg Trp Arg Lys Gly Glu Met Ile Gly Cys Gly Ala Phe
 1               5                  10                  15

Gly Arg Val Tyr Met Gly Met Asn Val Asp Ser Gly Glu Leu Leu Ala
            20                  25                  30

Ile Lys Glu Val Ser Ile Ala Met Asn Gly Ala Ser Arg Glu Arg Ala
        35                  40                  45

Gln Ala His Val Arg Glu Leu Glu Glu Glu Val Asn Leu Leu Lys Asn
    50                  55                  60

Leu Ser His Pro Asn Ile Val Arg Tyr Leu Gly Thr Ala Arg Glu Ala
65                  70                  75                  80

Gly Ser Leu Asn Ile Leu Leu Glu Phe Val Pro Gly Gly Ser Ile Ser
                85                  90                  95

Ser Leu Leu Gly Lys Phe Gly Ser Phe Pro Glu Ser Val Ile Arg Met
            100                 105                 110

Tyr Thr Lys Gln Leu Leu Leu Gly Leu Glu Tyr Leu His Lys Asn Gly
        115                 120                 125

Ile Met His Arg Asp Ile Lys Gly Ala Asn Ile Leu Val Asp Asn Lys
    130                 135                 140

Gly Cys Ile Lys Leu Ala Asp Phe Gly Ala Ser Lys Lys Val Val Glu
145                 150                 155                 160

Leu Ala Thr Met Thr Gly Ala Lys Ser Met Lys Gly Thr Pro Tyr Trp
                165                 170                 175

Met Ala Pro Glu Val Ile Leu Gln Thr Gly His Ser Phe Ser Ala Asp
            180                 185                 190

Ile Trp Ser Val Gly Cys Thr Ile Ile Glu Met Ala Thr Gly Lys Pro
        195                 200                 205

Pro Trp Ser Gln Gln Tyr Gln Glu Val Ala Ala Leu Phe His Ile Gly
    210                 215                 220

Thr Thr Lys Ser His Pro Pro Ile Pro Glu His Leu Ser Ala Glu Ser
```

```
225                 230                 235                 240
Lys Asp Phe Leu Leu Lys Cys Leu Gln Lys Glu Pro His Leu Arg His
                245                 250                 255
Ser Ala Ser Asn Leu Leu Gln His Pro Phe Val Thr
                260                 265
```

<210> SEQ ID NO 22
<211> LENGTH: 804
<212> TYPE: DNA
<213> ORGANISM: Nicotiana tabacum

<400> SEQUENCE: 22

```
ccgccaatcc ggtggaggaa aggtgaaatg attggatgtg gtgcttttgg tagggtttat      60
atggggatga atgttgattc tggagagtta ctcgctataa aggaggtttc gattgcgatg     120
aatggtgctt cgagagagcg agcacaagct catgttagag agcttgagga agaagtgaat     180
ctattgaaga atctctccca tcccaacata gtgagatatt tgggaactgc aagagaggca     240
ggatcattaa atatattgtt ggaatttgtt cctggtggct caatctcgtc acttttggga     300
aaatttggat ccttccctga atctgttata agaatgtaca ccaagcaatt gttattaggg     360
ttggaatact tgcataagaa tgggattatg cacagagata ttaagggagc aaacatactt     420
gttgacaata aaggttgcat taaacttgct gatttcggtg catccaagaa ggttgttgaa     480
ttggctacta tgactggtgc caagtcaatg aagggtactc catactggat ggctcccgaa     540
gtcattctgc agactggcca tagcttctct gctgacatat ggagtgtcgg atgcactatt     600
atcgaaatgg ctacaggaaa acctccttgg agccagcagt atcaggaggt tgctgctctc     660
ttccatatag ggacaaccaa atcccatccc cccatcccag agcatctttc tgctgaatca     720
aaggacttcc tattaaaatg tttgcagaag gaaccgcacc tgaggcattc tgcatcaaat     780
ttgcttcagc atccatttgt taca                                             804
```